(12) United States Patent
Chen Zeltsburg et al.

(10) Patent No.: US 11,814,657 B2
(45) Date of Patent: *Nov. 14, 2023

(54) MODIFIED DNASE AND USES THEREOF

(71) Applicant: Protalix Ltd., Carmiel (IL)

(72) Inventors: Lilach Chen Zeltsburg, Nahariya (IL); Ilya Ruderfer, Carmiel (IL); Avidor Shulman, Rakefet (IL); Liat Fux, Kiryat-Motzkin (IL); Yulia Ugortsev, Nesher (IL); Hagit Neta, Haifa (IL); Sivan Gelley, Kfar-Saba (IL); Elad Lavee Laviad, Kfar Neter (IL); Yoseph Shaaltiel, Timrat (IL)

(73) Assignee: Protalix Ltd., Carmiel (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/555,557

(22) Filed: Dec. 20, 2021

(65) Prior Publication Data

US 2022/0106578 A1  Apr. 7, 2022

Related U.S. Application Data

(63) Continuation of application No. 15/540,264, filed as application No. PCT/IL2016/050003 on Jan. 4, 2016, now Pat. No. 11,225,648.

(60) Provisional application No. 62/247,856, filed on Oct. 29, 2015, provisional application No. 62/169,724, filed on Jun. 2, 2015, provisional application No. 62/163,497, filed on May 19, 2015, provisional application No. 62/099,565, filed on Jan. 4, 2015, provisional application No. 62/099,560, filed on Jan. 4, 2015.

(51) Int. Cl.
| | |
|---|---|
| *C12N 9/22* | (2006.01) |
| *C12N 9/16* | (2006.01) |
| *A61K 38/46* | (2006.01) |
| *A61P 43/00* | (2006.01) |
| *A61P 11/00* | (2006.01) |
| *A61K 38/00* | (2006.01) |

(52) U.S. Cl.
CPC .............. *C12N 9/22* (2013.01); *A61K 38/465* (2013.01); *A61P 11/00* (2018.01); *A61P 43/00* (2018.01); *C12N 9/16* (2013.01); *A61K 38/00* (2013.01)

(58) Field of Classification Search
CPC ........................................................ C12N 9/22
See application file for complete search history.

(56) References Cited

U.S. PATENT DOCUMENTS

| | | | |
|---|---|---|---|
| 7,612,032 B2 | 11/2009 | Genkin et al. | |
| 8,431,123 B2 | 4/2013 | Genkin et al. | |
| 8,871,200 B2 | 10/2014 | Genkin et al. | |
| 8,916,151 B2 | 12/2014 | Genkin et al. | |
| 9,770,492 B2 | 9/2017 | Genkin et al. | |
| 11,225,648 B2 * | 1/2022 | Chen Zeltsburg | ... A61K 38/465 |
| 2001/0041360 A1 | 11/2001 | Lazarus et al. | |
| 2003/0044403 A1 | 3/2003 | Shak | |
| 2003/0044493 A1 | 3/2003 | Rettey et al. | |
| 2003/0054532 A1 | 3/2003 | Chan et al. | |
| 2007/0259367 A1 | 11/2007 | Ax et al. | |
| 2018/0112201 A1 | 4/2018 | Chen Zeltsburg et al. | |
| 2022/0106578 A1 * | 4/2022 | Chen Zeltsburg | ....... C12N 9/16 |

FOREIGN PATENT DOCUMENTS

| | | |
|---|---|---|
| WO | WO 90/07572 | 7/1990 |
| WO | WO 96/26279 | 8/1996 |
| WO | WO 97/47751 | 12/1997 |
| WO | WO 2013/114374 | 8/2013 |
| WO | WO 2016/108244 | 7/2016 |

OTHER PUBLICATIONS

The Merck Index (1983) Tenth Edition, p. 549. Windholz M. (eds.) Merck & Co., Inc., Rahway, NJ (Year: 1983).*
Examination Report dated Apr. 12, 2022 From the New Zealand Intellectual Property Office Re. Application No. 733912. (5 Pages).
Communication Pursuant to Article 94(3) EPC dated Dec. 15, 2021 From the European Patent Office Re. Application No. 16706685.1. (5 Pages).
Communication Pursuant to Article 94(3) EPC dated Dec. 17, 2019 From the European Patent Office Re. Application No. 16706685.1. (5 Pages).
Decision of Rejection dated Jun. 25, 2021 From the State Intellectual Property Office of the People's Republic of China Re. Application No. 201680012991.2. (4 Pages).
Examination Report dated Oct. 12, 2020 From the Institute Mexicano de la Propiedad Industrial, IMPI, Secretaria de Economia, Direccion Divisional de Patentes Re. Application No. MX/a/2017/008567. (6 Pages).
Examination Report dated May 18, 2021 From the Institute Mexicano de la Propiedad Industrial, Direccion Divisional de Patentes Re. Application No. 2017/008567. (4 Pages).
International Preliminary Report on Patentability dated Jul. 13, 2017 From the International Bureau of WIPO Re. Application No. PCT/IL2016/050003. (7 Pages).
International Search Report and the Written Opinion dated May 9, 2016 From the International Searching Authority Re. Application No. PCT/IL2016/050003.
Notification of Office Action and Search Report dated Feb. 24, 2021 From the State Intellectual Property Office of the People's Republic of China Re. Application No. 201680012991.2. (8 Pages).

(Continued)

*Primary Examiner* — Tekchand Saidha

(57) ABSTRACT

Modified DNase I protein in which one or more amino acids of a DNase I protein are modified non-cellularly, are provided. The modified DNase I protein exhibits a DNA hydrolytic activity in the presence of actin and an improved DNA hydrolytic activity compared to a homologous non-modified DNase I protein. Processes of preparing the modified DNase I protein and uses thereof in, for example, reducing a DNA content in sputum and/or in treating a disease or condition associated with excess extracellular DNA in a fluid, secretion or tissue of a subject, are also provided.

19 Claims, 39 Drawing Sheets

Specification includes a Sequence Listing.

(56) References Cited

OTHER PUBLICATIONS

Office Action dated Feb. 11, 2019 From the Israel Patent Office Re. Application No. 253208 and Its Translation Into English. (6 Pages).
Office Action dated Feb. 23, 2020 From the Israel Patent Office Re. Application No. 253208. (4 Pages).
Office Action dated May 30, 2021 From the Israel Patent Office Re. Application No. 253208 and Its Translation Into English. (6 Pages).
Patent Examination Report dated Mar. 17, 2021 From the Australian Government, IP Australia Re. Application No. 2016204793. (4 Pages).
Requisition bv the Examiner dated Dec. 16, 2021 From the Innovation, Science and Economic Development Canada, Canadian Intellectual Property Office Re. Application No. 2,970,216, (13 Pages).
Summary of Translation Dated Jul. 5, 2021 of Decision of Rejection dated Jun. 25, 2021 From the State Intellectual Property Office of the People's Republic of China Re. Application No. 201680012991.2. (6 Pages).
Translation Dated Jul. 2, 2021 of Mexican OA dated Jun. 16, 2021 From the Institute Mexicano de la Propiedad Industrial, Direccion Divisional de Patentes Re. Application No. 2017/008567. (4 Pages).
Translation Dated Dec. 11, 2020 of Examination Report dated Oct. 12, 2020 From the Institute Mexicano de la Propiedad Industrial, IMPI, Secretaria de Economia, Direccion Divisional de Patentes Re. Application No. MX/a/2017/008567. (6 Pages).
Translation Dated Mar. 16, 2021 of Notification of Office Action dated Feb. 24, 2021 From the State Intellectual Property Office of the People's Republic of China Re. Application No. 201680012991.2. (13 Pages).
Translation Dated Apr. 28, 2020 of Office Action dated Feb. 23, 2020 From the Israel Patent Office Re. Application No. 253208. (3 Pages).

Bucki et al. "Enhancement of Pulmozyme Activity in Purulent Sputum by Combination With Poly-Aspartic Acid or Gelsolin", Journal of Cystic Fibrosis, 14(5): 587-593, Available Online Feb. 13, 2015.
Lazarides et al. "Actin Is the Naturally Occurring Inhibitor of Deoxyribonuclease I", Proc. Natl. Acad. Sci. USA, 71(12): 4742-4746, Dec. 1974.
Mannherz et al. "The Interaction of Bovine Pancreatic Deoxyribonuclease I and Skeletal Muscle Actin", European Journal of Biochemistry, 104: 367-379, 1980.
Pan et al. "Hyperactivity of Human DNase I Variants. Dependence on the Number of Positively Charged Residues and Concentration, Length, and Environment of DNA", The Journal of Biological Chemistiy, 273(19): 11701-11708, May 8, 1998.
Pan et al. "Improved Potency of Hyperactive and Actin-Resistant Human DNase I Variants for Treatment of Cystic Fibrosis and Systemic Lupus Erythematosus", The Journal of Biological Chemistry, 273(29): 18374-18381, Jul. 17, 1998.
Shak et al. "Recombinant Human DNase I Reduces the Viscosity of Cystic Fibrosis Sputum", Proc. Natl. Acad. Sci. USA, 87: 9188-9192, Dece. 1990.
Tawfik "Amidation of Carboxyl Groups", The Protein Protocols Handbook, 2nd Edition, pp. 477-478, 2002.
Examination Report dated Feb. 1, 2022 From the Instituto Mexicano de la Propiedad Industrial, IMPI, Secretaria de Economia, Direccion Divisional de Patentes Re. Application No. MX/a/2017/008567 together with English Summary. (7 Pages).
Requisition by the Examiner dated Nov. 15, 2022 From the Innovation, Science and Economic Development Canada, Canadian Intellectual Property Office Re. Application No. 2,970,216. (10 Pages).

* cited by examiner

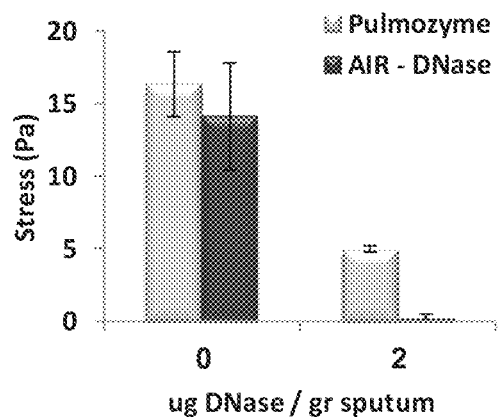
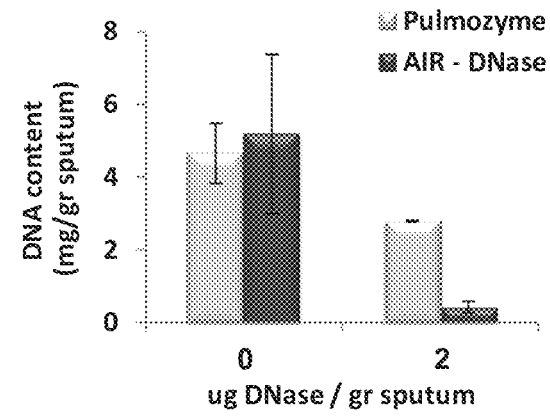
FIG. 41A  FIG. 41B
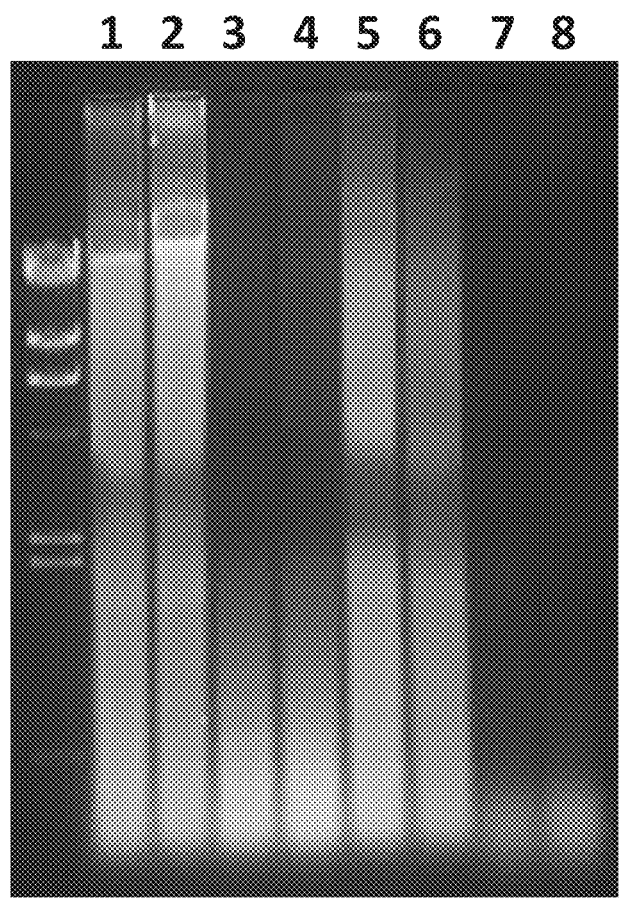
FIG. 41C

| Glycan | | Relative amount |
|---|---|---|
| formula | structure | |
| A1X | | minor |
| Fc(3)M3X/M4X | | minor |
| Fc(3)XA1 | | major |
| Fc(3)XA2 | | major |

MODIFIED DNASE AND USES THEREOF

RELATED APPLICATIONS

This application is a continuation of U.S. patent application Ser. No. 15/540,264 filed on Jun. 28, 2017, which is a National Phase of PCT Patent Application No. PCT/IL2016/050003 having International Filing Date of Jan. 4, 2016, which claims the benefit of priority under 35 USC § 119(e) of U.S. Provisional Patent Applications Nos. 62/247,856 filed on Oct. 29, 2015, 62/169,724 filed on Jun. 2, 2015, 62/163,497 filed on May 19, 2015, 62/099,560 and 62/099,565 both filed on Jan. 4, 2015. The contents of the above applications are all incorporated by reference as if fully set forth herein in their entirety.

SEQUENCE LISTING STATEMENT

The ASCII file, entitled 90204SequenceListing.txt, created on Dec. 20, 2021, comprising 14,952 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to therapy, and more particularly, but not exclusively, to non-cellularly modified DNase I protein, to processes of preparing same, and to therapeutic uses thereof.

Based on their biochemical properties and enzymatic activities deoxyribonuclease (DNase) proteins have been classified as two types, DNase I and DNase II. DNase I proteins have a pH optimum near neutrality, and produce 5'-phosphate nucleotides upon hydrolysis of DNA.

Human DNase I is a member of the mammalian DNase I family (EC 3.1.21.1). DNase I belongs to the class of $Mg^{2+}$ and $Ca^{2+}$ dependent endonucleases, whose hydrolytic activity depends on the presence of divalent cations. $Mg^{2+}$ ion is involved in electrophilic catalysis of the phosphodiester bond cleavage, whereas $Ca^{2+}$ maintains optimal enzyme conformation. DNase I cleaves DNA preferentially at phosphodiester linkages adjacent to a pyrimidine nucleotide, yielding 5'-phosphate-terminated polynucleotides with a free hydroxyl group on position 3', on average producing tetranucleotides. It acts on single-stranded DNA, double-stranded DNA, and chromatin.

The principal therapeutic use of human DNase has been to reduce the viscoelasticity of pulmonary secretions (including mucus) in diseases such as pneumonia and cystic fibrosis (CF), by hydrolyzing high molecular weight DNA that is present in such secretions, thereby aiding in the clearing of respiratory airways [Shak et al., PNAS 87:9188-9192 (1990)]. Mucus also contributes to the morbidity of chronic bronchitis, asthmatic bronchitis, bronchiectasis, emphysema, acute and chronic sinusitis, and even the common cold. The pulmonary secretions of persons having such diseases are complex materials that include mucus glycoproteins, mucopolysaccharides, proteases, actin, and DNA. DNase has also been proposed for non-pulmonary disorders, for example, treatment of male infertility and uterine disorders (see U.S. Patent Application Publication No. 2007/0259367), inhibition of metastatic growth (see U.S. Pat. No. 7,612,032) and topical application for viral conditions.

Dornase alfa is a recombinant human DNase (rhDNase) expressed in Chinese hamster ovary (CHO) cells, used in the treatment of cystic fibrosis, and marketed under the trade name Pulmozyme®.

International Patent Application Publication WO 2013/114374 describes plant-expressed human recombinant DNase I proteins, and uses thereof for treating pulmonary and/or respiratory conditions by inhalation of the DNase I.

The DNA-hydrolytic activity of DNase I in pulmonary secretions may be reduced as a result of the interaction of the DNase I with actin [Lazarides et al., PNAS 71:4742-4746 (1974); Mannherz et al., Eur J Biochem 104:367-379 (1980)].

International Patent Application Publication WO 96/26279 describes amino acid sequence variants of human DNase I having reduced binding affinity to actin, and uses thereof for reducing viscosity of mucus. The actin-resistant DNase variants A114R and A114F have been reported to be more effective than wild-type DNase at reducing viscosity and increasing cough transport of airway secretions of cystic fibrosis patients [Zahm et al., Am J Respir Crit Care Med 163:1153-1157 (2001); Pan et al., J Biol Chem 273:18374-18381 (1998)].

Introduction of additional positively charged amino acids into the DNase I sequence results in a more active DNase I variant. The number of additional positively charged amino groups which results in the greatest enhancement of activity depends on concentrations of DNA and ions [Pan & Lazarus, J Biol Chem 273:11701-11708 (1998); Pan et al., J Biol Chem 273:18374-18381 (1998)].

DNase I variants comprising both additional positively charged amino acids for enhancing activity and the actin-resistant mutation A114F were reported to be more potent at degrading DNA in sputum of cystic fibrosis than variants characterized by additional positively charged amino acids alone or the actin-resistant mutation alone [Pan et al., J Biol Chem 273:18374-18381 (1998)].

Polyaspartic acid and the actin severing protein gelsolin have been reported to enhance the ability of DNase I (dornase alfa) to fluidize sputum of cystic fibrosis patients [Bucki et al., J Cystic Fibrosis 2015, 14:587-593].

SUMMARY OF THE INVENTION

According to an aspect of some embodiments of the present invention there is provided a modified DNase I protein.

According to some embodiments of the present invention, the modified DNase I protein comprises an amino acid sequence of a DNase I protein (e.g., a DNase I protein that is inhibited by actin, as defined herein), and is modified such that at least one amino acid residue in the DNase I protein is a non-cellularly modified amino acid residue.

According to some embodiments of the present invention, the modified DNase I protein as described in any one of the embodiments herein, and any combination thereof, is characterized by, or exhibits, at least one property selected from the group consisting of:

a) a DNA hydrolytic activity in the presence of 5 µg/ml human non-muscle actin which is at least 50% of a DNA hydrolytic activity of the modified DNase I protein in the absence of human non-muscle actin, at a modified DNase I concentration of 45 ng/ml;

b) a DNA hydrolytic activity in the presence of 50 µg/ml human non-muscle actin which is at least 20% of a DNA hydrolytic activity of the modified DNase I protein in the absence of human non-muscle actin, at a DNase I concentration of 45 ng/ml;

c) a DNA hydrolytic activity in the presence of 5 μg/ml human non-muscle actin which is at least 150% of a DNA hydrolytic activity of a non-modified DNase I protein in the presence of 5 μg/ml human non-muscle actin, at a DNase I concentration of 45 ng/ml;

d) a DNA hydrolytic activity in the presence of 50 μg/ml human non-muscle actin which is at least 150% of a DNA hydrolytic activity of a non-modified DNase I protein in the presence of 50 μg/ml human non-muscle actin, at a DNase I concentration of 45 ng/ml; and e) an $IC_{50}$ with respect to DNA hydrolytic activity in the presence of human non-muscle actin which is at least twice an $IC_{50}$ of a non-modified DNase I protein with respect to DNA hydrolytic activity in the presence of human non-muscle actin.

According to some of any of the embodiments of the present invention, the modified DNase I protein is characterized by a DNA hydrolytic activity in the presence of 1 μg/ml human non-muscle actin which is at least 80% of a DNA hydrolytic activity of the modified DNase I protein in the absence of human non-muscle actin, at a DNase I concentration of 45 ng/ml.

According to some of any of the embodiments of the present invention, the modified DNase I protein is characterized by a DNA hydrolytic activity in the presence of 5 μg/ml human non-muscle actin which is at least 70% of a DNA hydrolytic activity of the modified DNase I protein in the absence of human non-muscle actin, at a DNase I concentration of 45 ng/ml.

According to some of any of the embodiments of the present invention, the modified DNase I protein is characterized by a DNA hydrolytic activity in the presence of 50 μg/ml human non-muscle actin which is at least 50% of a DNA hydrolytic activity of the modified DNase I protein in the absence of human non-muscle actin, at a DNase I concentration of 45 ng/ml.

According to some of any of the embodiments of the present invention, the modified DNase I protein is characterized by a DNA hydrolytic activity in the presence of 5 μg/ml human non-muscle actin which is at least 200% of a DNA hydrolytic activity of a non-modified DNase I protein in the presence of 5 μg/ml human non-muscle actin, at a DNase I concentration of 45 ng/ml.

According to some of any of the embodiments of the present invention, the modified DNase I protein is characterized by a DNA hydrolytic activity in the presence of 50 μg/ml human non-muscle actin which is at least 200% of a DNA hydrolytic activity of a non-modified DNase I protein in the presence of 50 μg/ml human non-muscle actin, at a DNase I concentration of 45 ng/ml.

According to some of any of the embodiments of the present invention, the modified DNase I protein is characterized by an $IC_{50}$ with respect to DNA hydrolytic activity in the presence of human non-muscle actin which is at least 3-fold an $IC_{50}$ of a non-modified DNase I protein with respect to DNA hydrolytic activity in the presence of human non-muscle actin.

According to some of any of the embodiments of the present invention, the modified DNase I protein is such that at least two, or at least five amino acid residues are the non-cellularly modified amino acid residues as described herein.

According to some of any of the embodiments of the present invention, the modified DNase I protein is such that at least one carboxylic acid group of the (non-modified) DNase I protein is replaced by an amide group of the formula:

—C(=O)—NR'R"

wherein each of R' and R" is independently selected from the group consisting of hydrogen, and a saturated or unsaturated, substituted or non-substituted hydrocarbon moiety, optionally interrupted by one or more heteroatoms.

According to some embodiments of the present invention, at least one of R' and R" of the formula above is the saturated or unsaturated, substituted or non-substituted hydrocarbon moiety, optionally interrupted by one or more heteroatoms.

According to an aspect of some embodiments of the present invention there is provided a modified DNase I protein comprising an amino acid sequence of a DNase I protein, in which at least one carboxylic acid group in the DNase I protein is replaced by an amide group of the formula:

—C(=O)—NR'R"

wherein each of R' and R" is independently selected from the group consisting of hydrogen, and a saturated or unsaturated, substituted or non-substituted hydrocarbon moiety, optionally interrupted by one or more heteroatoms.

According to some embodiments of the present invention, at least one of R' and R" is the saturated or unsaturated, substituted or non-substituted hydrocarbon moiety, optionally interrupted by one or more heteroatoms.

According to some of any of the embodiments of the present invention, the hydrocarbon is selected from the group consisting of alkyl, alkenyl, alkynyl, cycloalkyl, aryl, heteroalicyclic and heteroaryl, each being substituted or non-substituted.

According to some of these embodiments of the present invention, the modified DNase I protein is characterized by at least one property selected from the group consisting of:

a) a DNA hydrolytic activity in the presence of 5 μg/ml human non-muscle actin which is at least 50% of a DNA hydrolytic activity of the modified DNase I protein in the absence of human non-muscle actin, at a modified DNase I concentration of 45 ng/ml;

b) a DNA hydrolytic activity in the presence of 50 μg/ml human non-muscle actin which is at least 20% of a DNA hydrolytic activity of the modified DNase I protein in the absence of human non-muscle actin, at a DNase I concentration of 45 ng/ml;

c) a DNA hydrolytic activity in the presence of 5 μg/ml human non-muscle actin which is at least 150% of a DNA hydrolytic activity of a non-modified DNase I protein in the presence of 5 μg/ml human non-muscle actin, at a DNase I concentration of 45 ng/ml;

d) a DNA hydrolytic activity in the presence of 50 μg/ml human non-muscle actin which is at least 150% of a DNA hydrolytic activity of a non-modified DNase I protein in the presence of 50 μg/ml human non-muscle actin, at a DNase I concentration of 45 ng/ml; and e) an $IC_{50}$ with respect to DNA hydrolytic activity in the presence of human non-muscle actin which is at least twice an $IC_{50}$ of a non-modified DNase I protein with respect to DNA hydrolytic activity in the presence of human non-muscle actin, as these properties are described herein, in any of the respective embodiments and any combination thereof.

According to some of any of the embodiments of the present invention, the amide group has the general formula:

—C(=O)—NH—R' wherein R' is selected from the group consisting of alkyl, alkenyl and alkynyl, each being non-substituted or substituted with one or more substituents selected from the group consisting of hydroxy and amino.

According to some of any of the embodiments of the present invention, R' comprises from 1 to 10 carbon atoms.

According to some of any of the embodiments of the present invention, R' comprises from 2 to 6 carbon atoms.

According to some of any of the embodiments of the present invention, the alkyl, the alkenyl or the alkynyl is substituted with one or more hydroxy group.

According to some of any of the embodiments of the present invention, R' is tris(hydroxymethyl)methyl.

According to some of any of the embodiments of the present invention, the alkyl, the alkenyl or the alkynyl is substituted with one or more amino group.

According to some of any of the embodiments of the present invention, R' is 2-aminoethyl.

According to some of any of the embodiments of the present invention, the at least one carboxylic acid group (which is replaced by an amide) is selected from the group consisting of a carboxylic group within a side chain of an amino acid residue and a C-terminal carboxylic acid group.

According to some of any of the embodiments of the present invention, the side chain of an amino acid residue is a side chain of an amino acid residue selected from the group consisting of a glutamic acid residue, an aspartic acid residue, an N-methyl-glutamic acid residue, an N-methyl-aspartic acid residue, an α-methylglutamic acid residue, an α-methylaspartic acid residue, a γ-carboxyglutamic acid residue, an N-(carboxymethyl)glycine residue, an N-(2-carboxyethyl)glycine residue and an α-aminoadipic acid residue.

According to some of any of the embodiments of the present invention, at least two of the carboxylic acid groups of the DNase I protein are replaced by the amide group.

According to some of any of the embodiments of the present invention, at least 5 of the carboxylic acid groups of the DNase I protein are replaced by the amide group.

According to some of any of the embodiments of the present invention, the modified DNase I protein is characterized by a Michaelis constant with respect to DNA hydrolytic activity which is lower than a Michaelis constant of a non-modified DNase I protein with respect to DNA hydrolytic activity.

According to some of any of the embodiments of the present invention, the modified DNase I protein is characterized by a Michaelis constant with respect to DNA hydrolytic activity which is no more than 20 µg/ml DNA.

According to some of any of the embodiments of the present invention, the modified DNase I protein is characterized by a specific activity with respect to DNA hydrolytic activity which is at least 70% of a specific activity of a non-modified DNase I protein with respect to DNA hydrolytic activity.

According to some of any of the embodiments of the present invention, the modified DNase I protein is characterized by a catalytic efficiency with respect to DNA hydrolytic activity which is greater than a catalytic efficiency of a non-modified DNase I protein with respect to DNA hydrolytic activity.

According to some of any of the embodiments of the present invention, the modified DNase I protein is such that less than 10 weight percent of the modified DNase I is in a multimeric form.

According to some of any of the embodiments of the present invention, the (non-modified) DNase I protein is a recombinant protein.

According to some of any of the embodiments of the present invention, the (non-modified) DNase I protein is a plant-recombinant protein.

According to some of any of the embodiments of the present invention, the (non-modified) DNase I protein has at least 80% homology to a human DNase I protein.

According to some of any of the embodiments of the present invention, the (non-modified) DNase I protein comprises an N-terminal glycine residue.

According to some of any of the embodiments of the present invention, the (non-modified) DNase I protein comprises or has the amino acid sequence as set forth in SEQ ID NO: 2.

According to some of any of the embodiments of the present invention, the (non-modified) DNase I protein comprises or has the amino acid sequence as set forth in SEQ ID NO: 1.

According to some of any of the embodiments of the present invention, the (non-modified) DNase I protein has at least one core xylose and at least one core α-(1,3) fucose.

According to an aspect of some embodiments of the present invention there is provided a process of preparing the modified DNase I protein as described in any one of the embodiments herein, and any combination thereof, the process comprising reacting the (non-modified) DNase I protein with an amine-containing compound of the formula:

HNR'R"

in the presence of a coupling agent,
wherein each of R' and R" is a saturated or unsaturated, substituted or non-substituted hydrocarbon moiety, optionally interrupted by one or more heteroatoms independently selected from the group consisting of hydrogen, and a substituted or non-substituted alkyl, alkenyl, alkynyl, cycloalkyl, aryl, heteroalicyclic and heteroaryl, as described herein.

According to some embodiments of the present invention, at least one of R' and R" is the hydrocarbon moiety, as described herein.

According to some embodiments of the present invention, the amine-containing compound has the general formula:

H$_2$N—R' wherein R' is a saturated or unsaturated alkyl group, being non-substituted or substituted with one or more substituents selected from the group consisting of hydroxy and amino.

According to some of any of the embodiments of the present invention, the coupling agent is a carbodiimide.

According to some of any of the embodiments of the present invention, the carbodiimide is CMC (N-cyclohexyl-N'-(2-morpholinoethyl)carbodiimide metho-p-toluenesulfonate).

According to an aspect of some embodiments of the present invention there is provided a pharmaceutical composition comprising, as an active ingredient, the modified DNase I protein as described in any one of the embodiments herein, and any combination thereof, and a pharmaceutically acceptable carrier.

According to some of any of the embodiments of the present invention, the pharmaceutical composition further comprises, as an active ingredient, a calcium salt.

According to some of any of the embodiments of the present invention, a concentration of calcium in the composition is in a range of from 5 to 15 mM of calcium.

According to some of any of the embodiments of the present invention, the pharmaceutical composition further comprises polysorbate 80.

According to some of any of the embodiments of the present invention, the pharmaceutical composition comprises about 10 mM $CaCl_2$, about 0.01% polysorbate 80, about 140 mM NaCl, and about 5 mg/ml of the modified DNase I protein.

According to some of any of the embodiments of the present invention, pharmaceutical composition is formulated for delivery via nebulizer.

According to some of any of the embodiments of the present invention, the modified DNase I protein is at least 90% pure DNase I protein.

According to some of any of the embodiments of the present invention, the pharmaceutical composition or the modified DNase I protein as described in any one of the respective embodiments and any combination thereof, is for use in reducing the viscosity of sputum.

According to some of any of the embodiments of the present invention, the pharmaceutical composition or the modified DNase I protein as described in any one of the respective embodiments and any combination thereof, is for use in reducing a DNA content in sputum.

According to some of any of the embodiments of the present invention, the pharmaceutical composition or the modified DNase I protein as described in any one of the respective embodiments and any combination thereof, is for use in treating a disease or condition associated with excess extracellular DNA in a fluid, secretion or tissue of a subject in need thereof.

According to some embodiments of the present invention, the disease or condition is a pulmonary disease or condition.

According to some of any of the embodiments of the present invention, the pulmonary disease or condition is selected from the group consisting of acute or chronic bronchopulmonary disease and atelectasis.

According to some of any of the embodiments of the present invention, the acute or chronic bronchopulmonary disease is selected from the group consisting of pneumonia, bronchitis or tracheobronchitis, bronchiectasis, cystic fibrosis, asthma, tuberculosis and fungal infections.

According to some of any of the embodiments of the present invention, the pharmaceutical composition or the modified DNase I protein as described in any one of the respective embodiments and any combination thereof, is for use in treating cystic fibrosis in a subject in need thereof.

According to some of any of the embodiments of the present invention, the pharmaceutical composition or the modified DNase I protein as described in any one of the respective embodiments and any combination thereof, is for use in treating a disease or condition selected from the group consisting of bronchitis, non-cystic fibrosis bronchiectasis, chronic obstructive pulmonary disease (COPD), lupus erythematosus, lupus nephritis, Cockayne syndrome, Angelman syndrome, male infertility, metastatic cancer, a viral, bacterial, fungal or protozoan infection sepsis, myocardial infarction, atherosclerosis, diabetes, delayed type hypersensitivity and a uterine disorder.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced. In the drawings.

Figure 9:
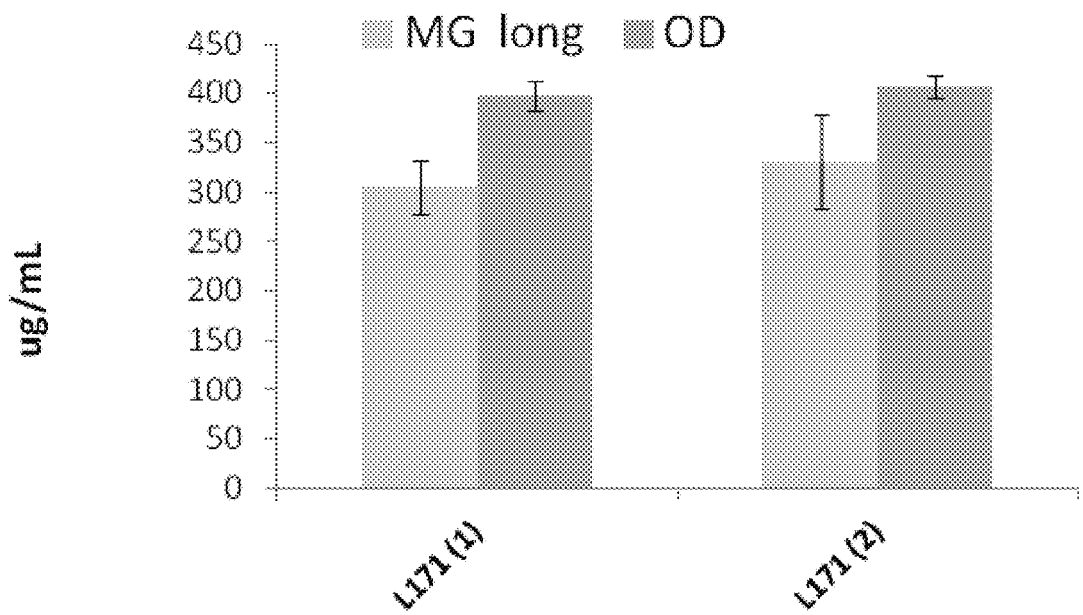
Figure 10:
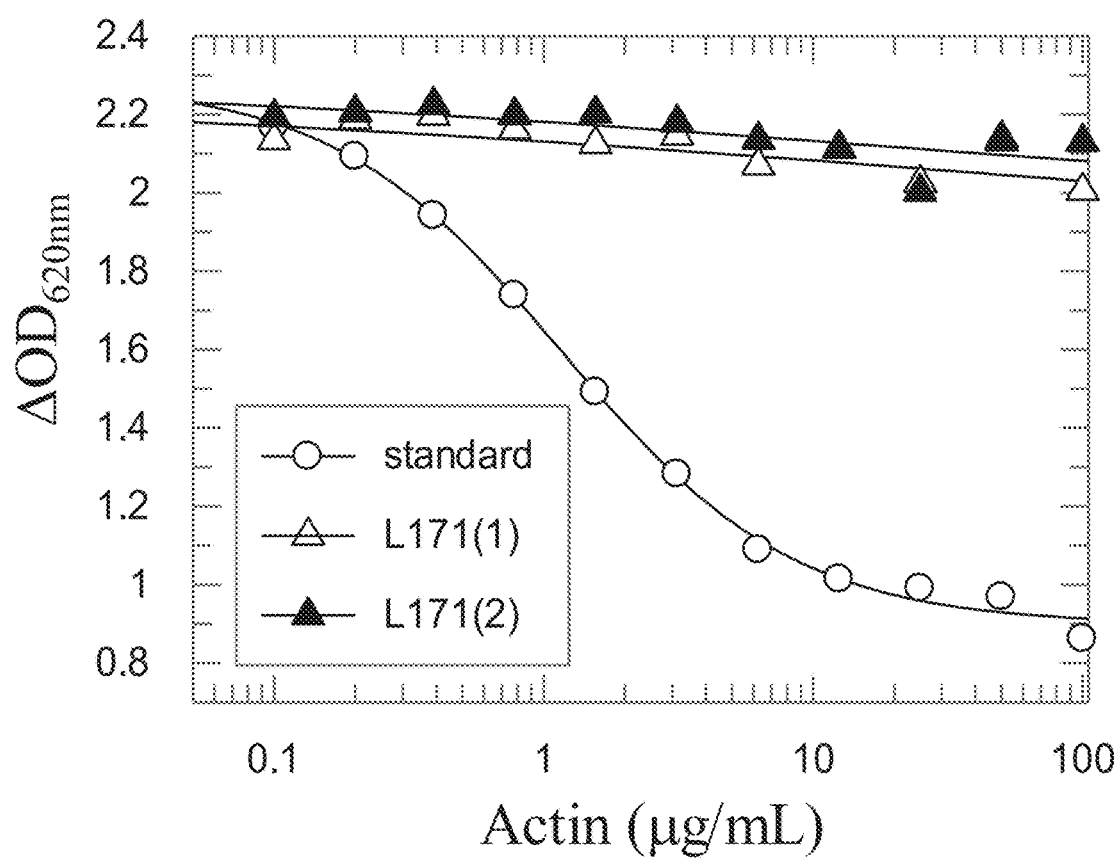
Figure 11:
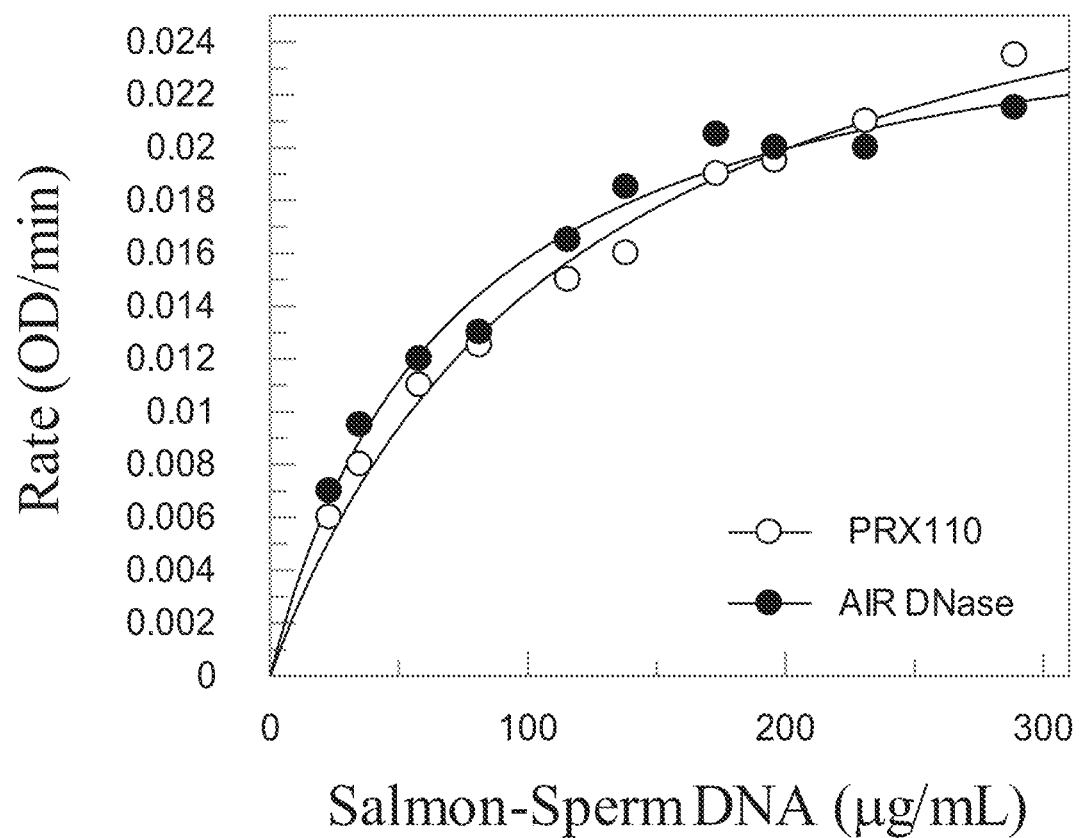
Figure 12A:
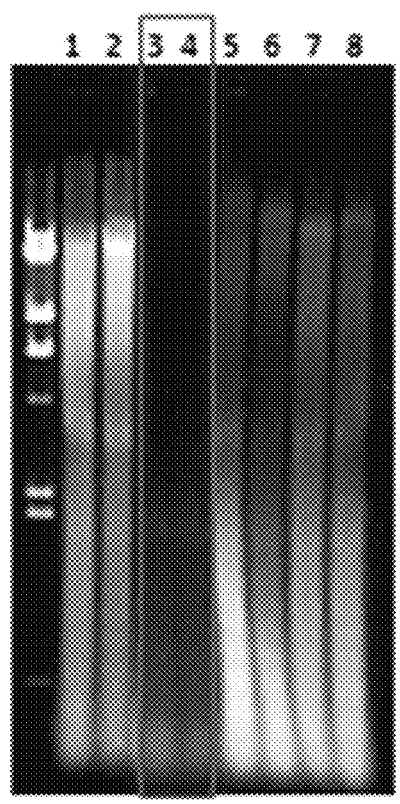
Figure 12B:
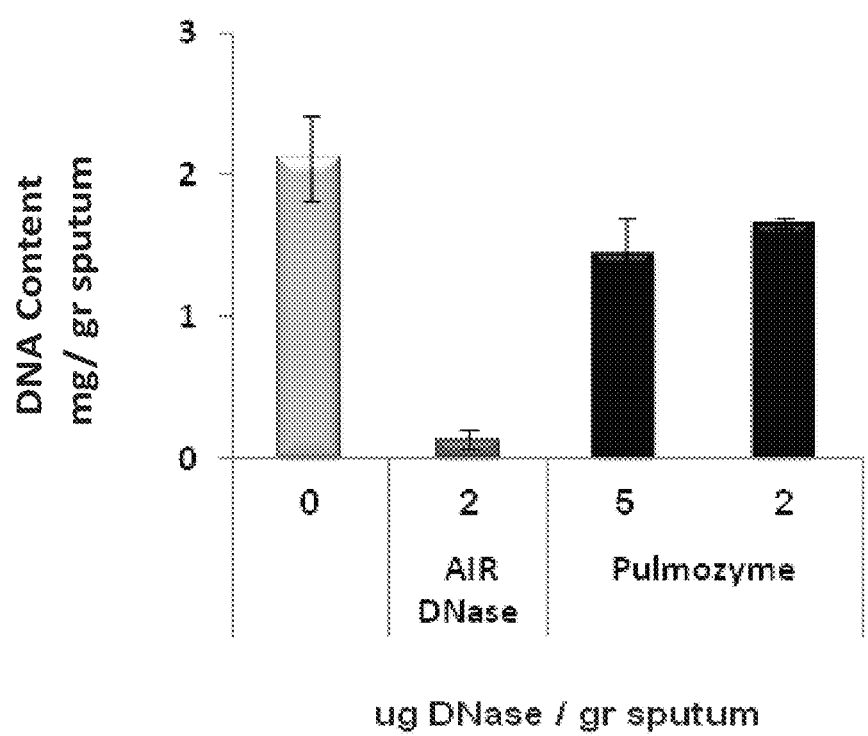
Figure 13:
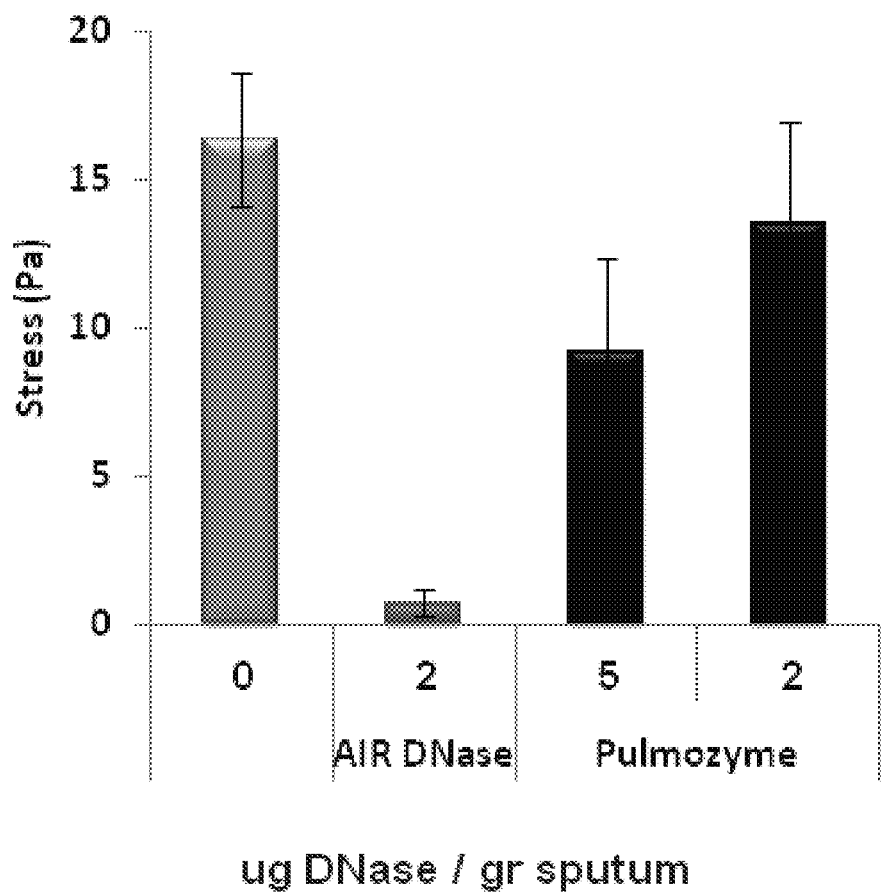
Figure 14:
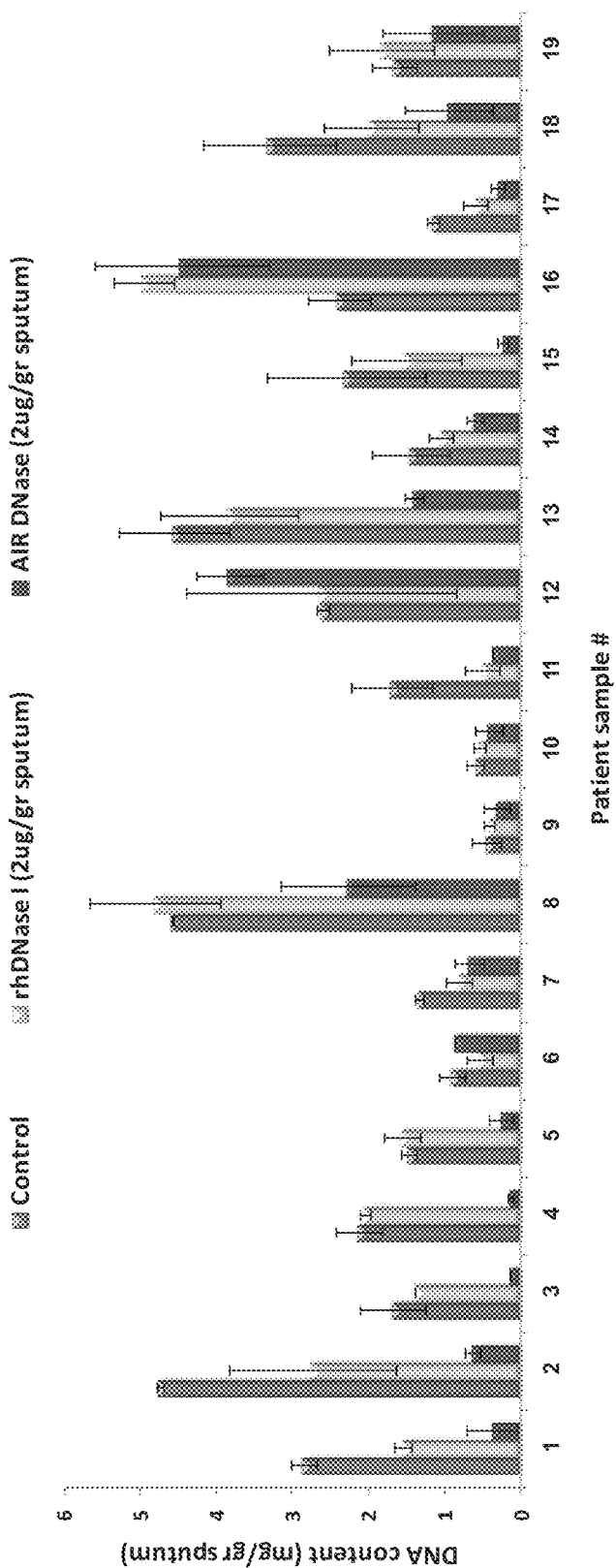
Figure 15:
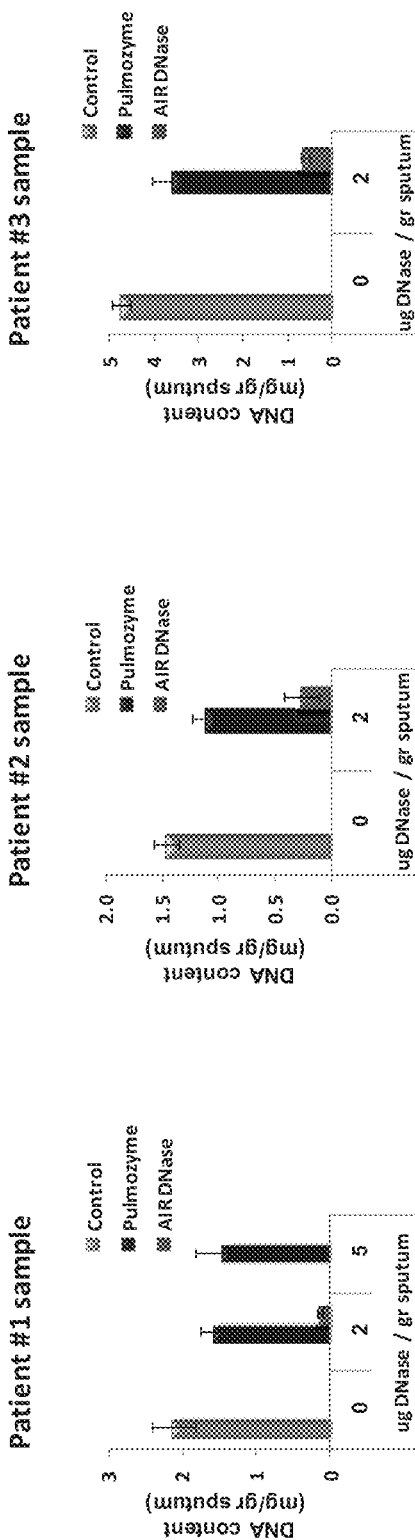
Figure 16A:
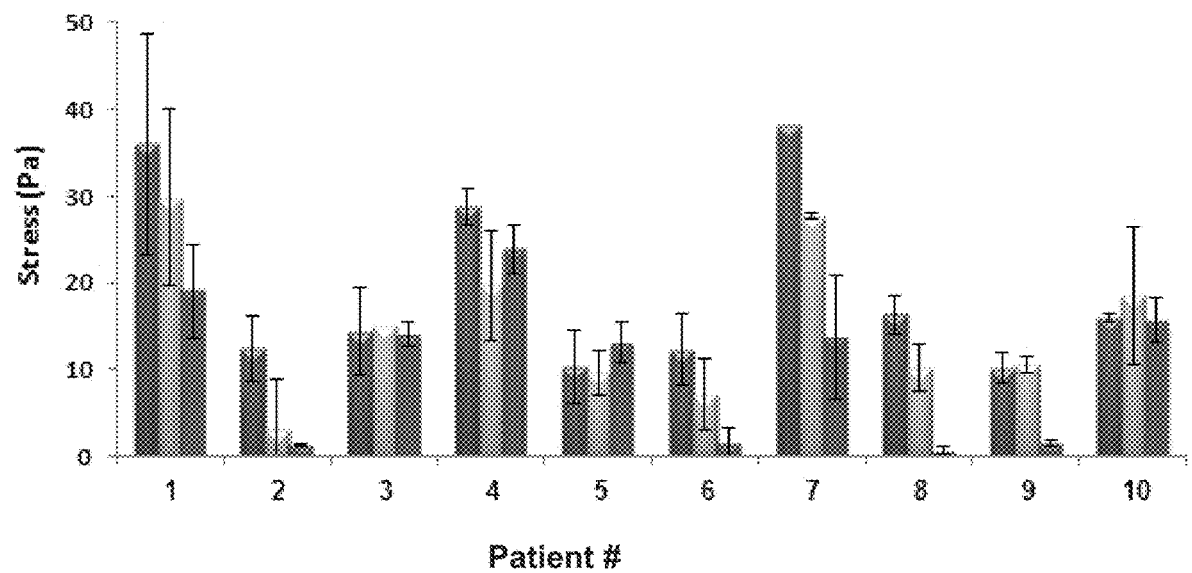
Figure 16B:
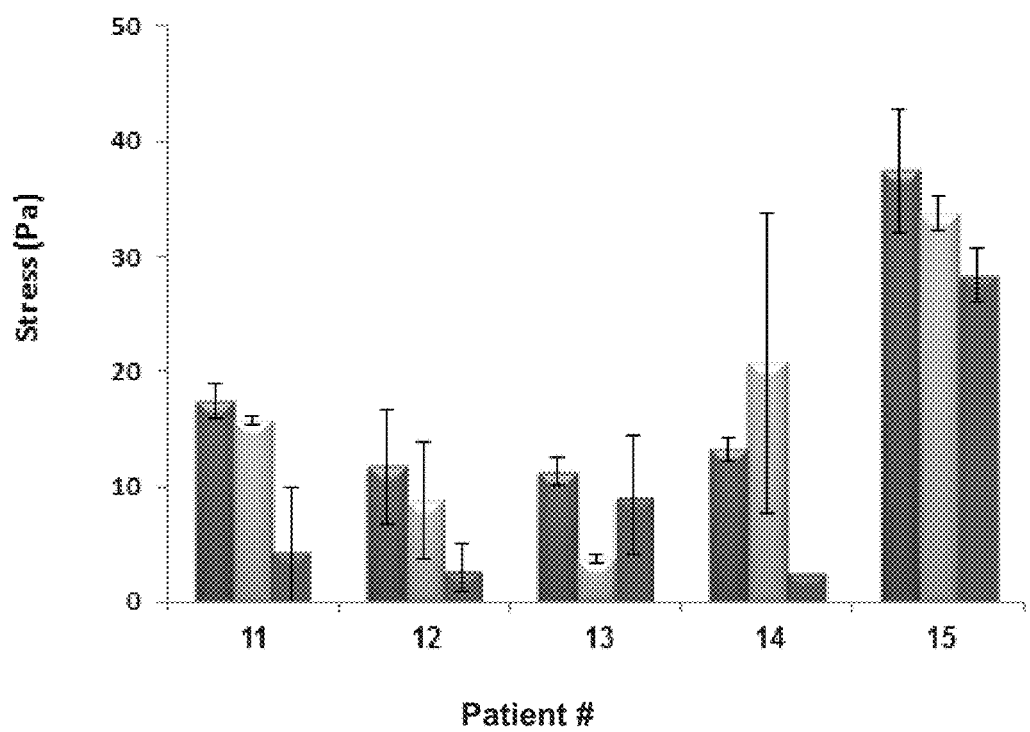
Figure 16C:
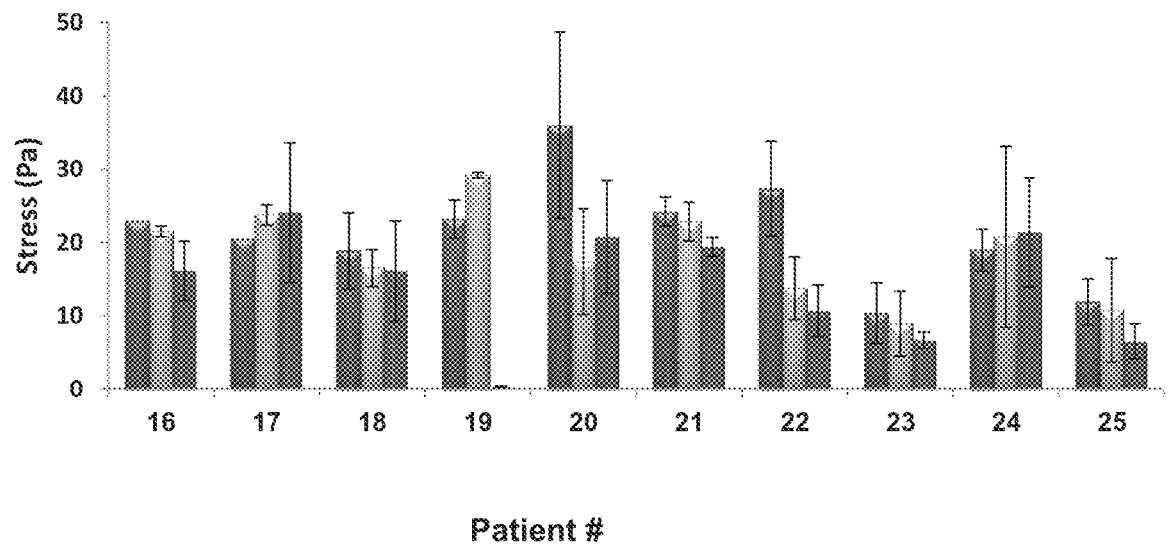
Figure 16D:
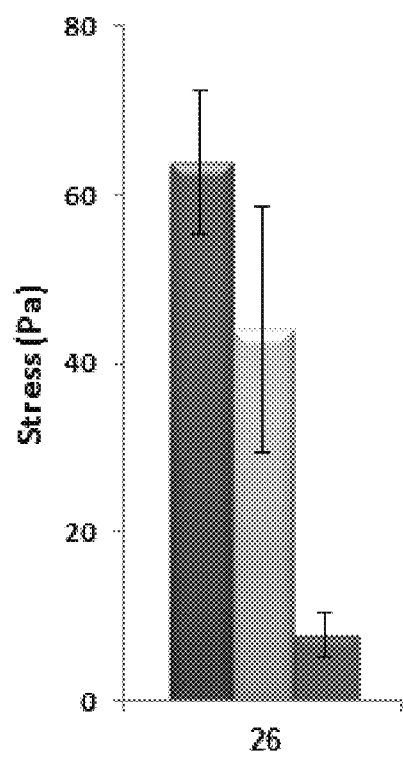
Figure 17:
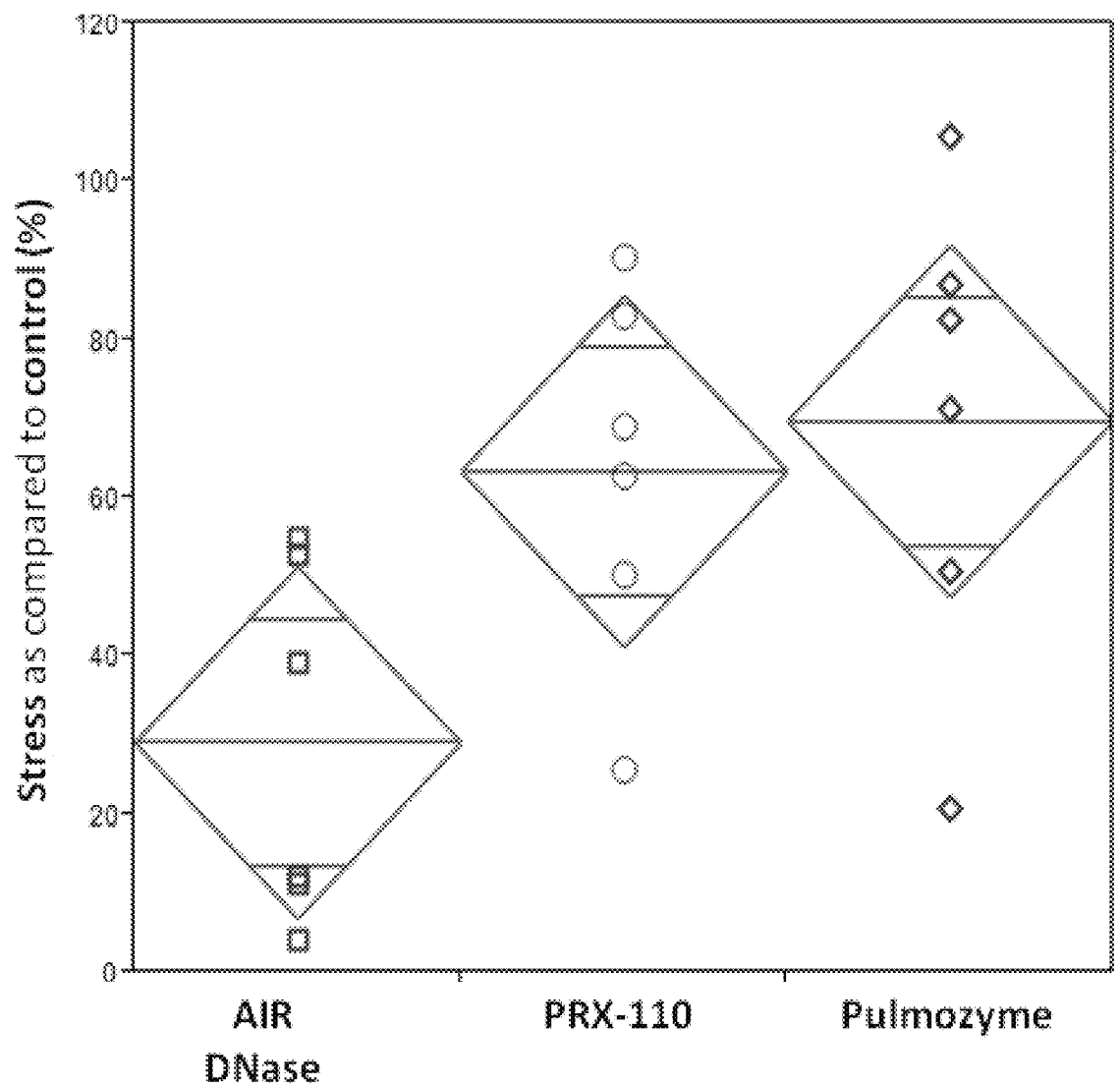
Figure 18:
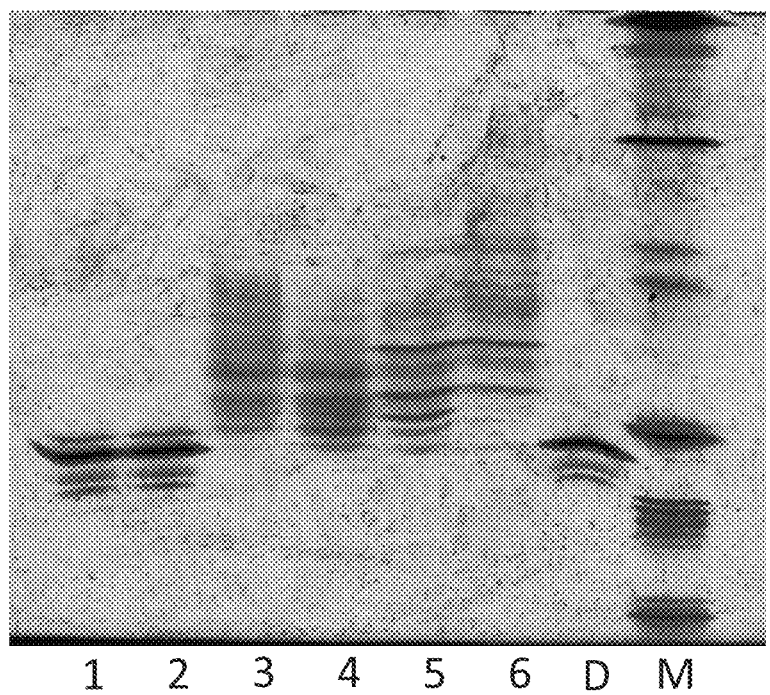
Figure 19:
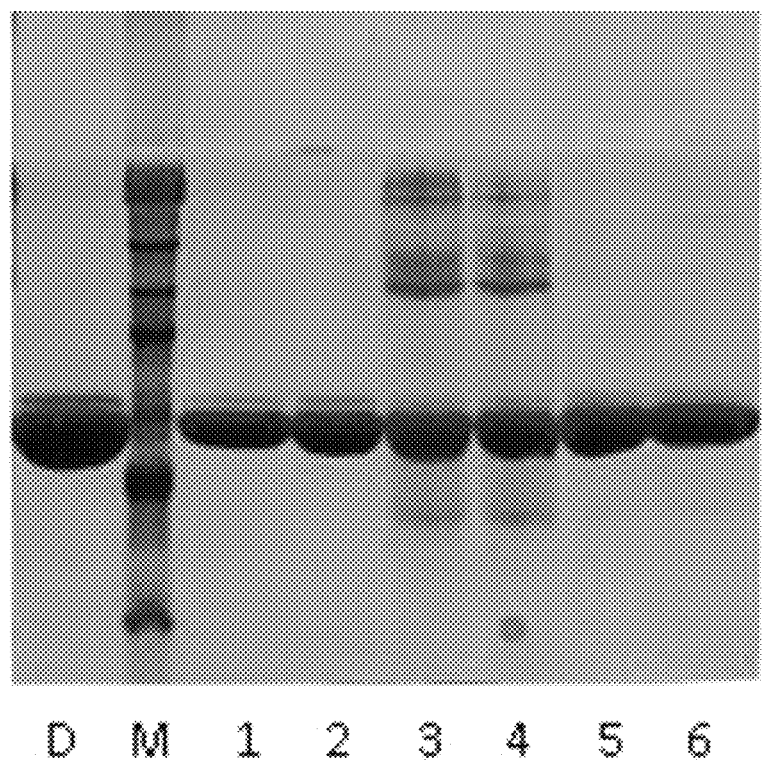
Figure 20:
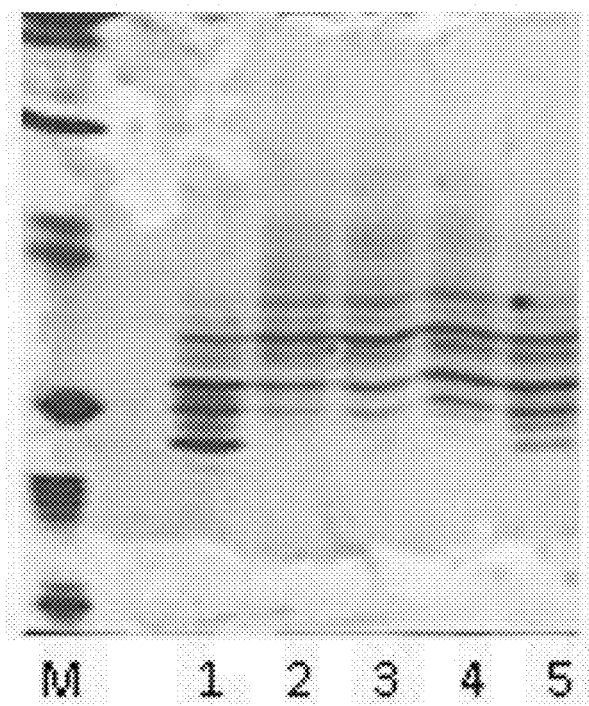
Figure 21:
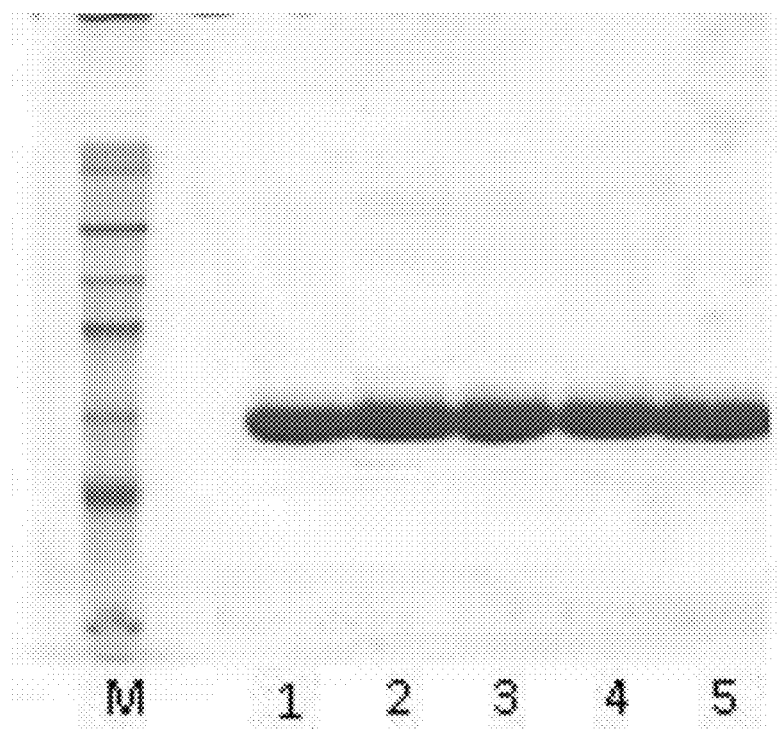
Figure 22:
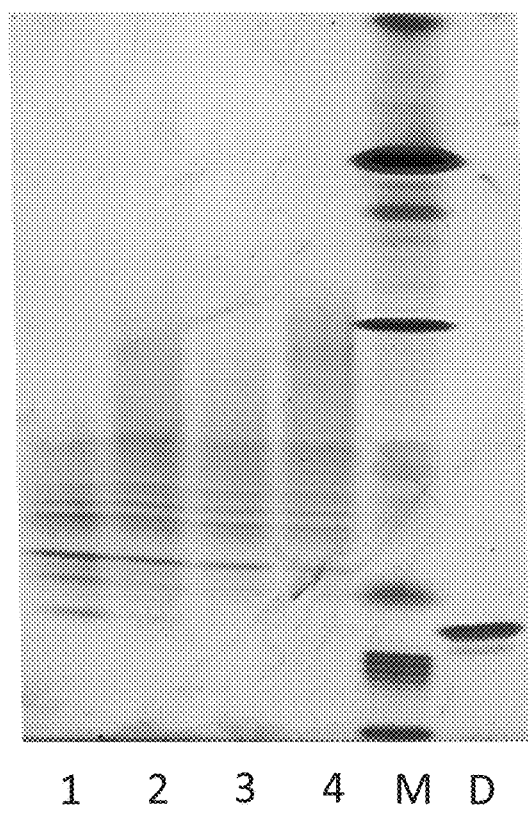
Figure 23:
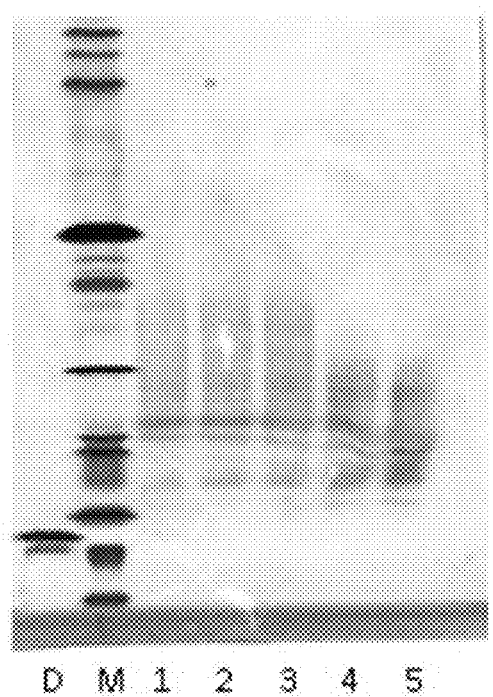
Figure 24:
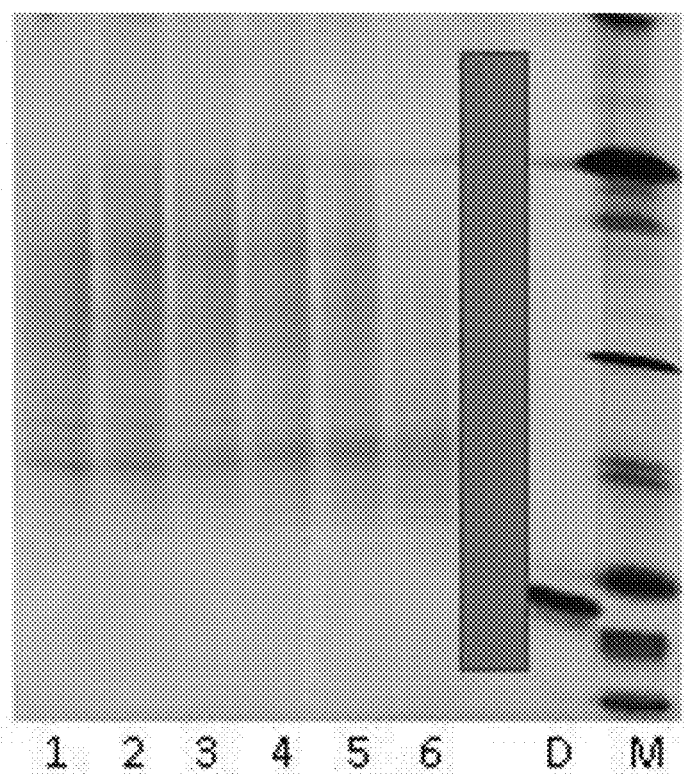
Figure 25:
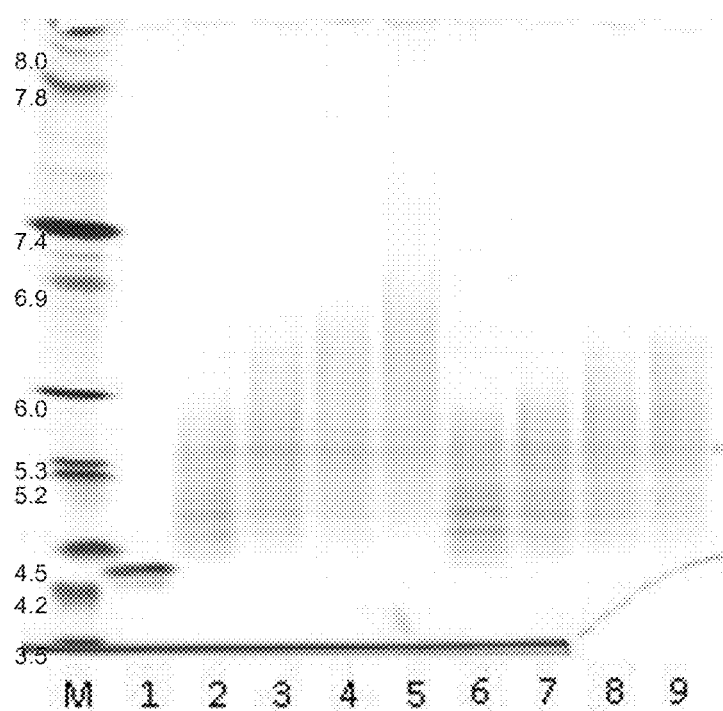
Figure 26:
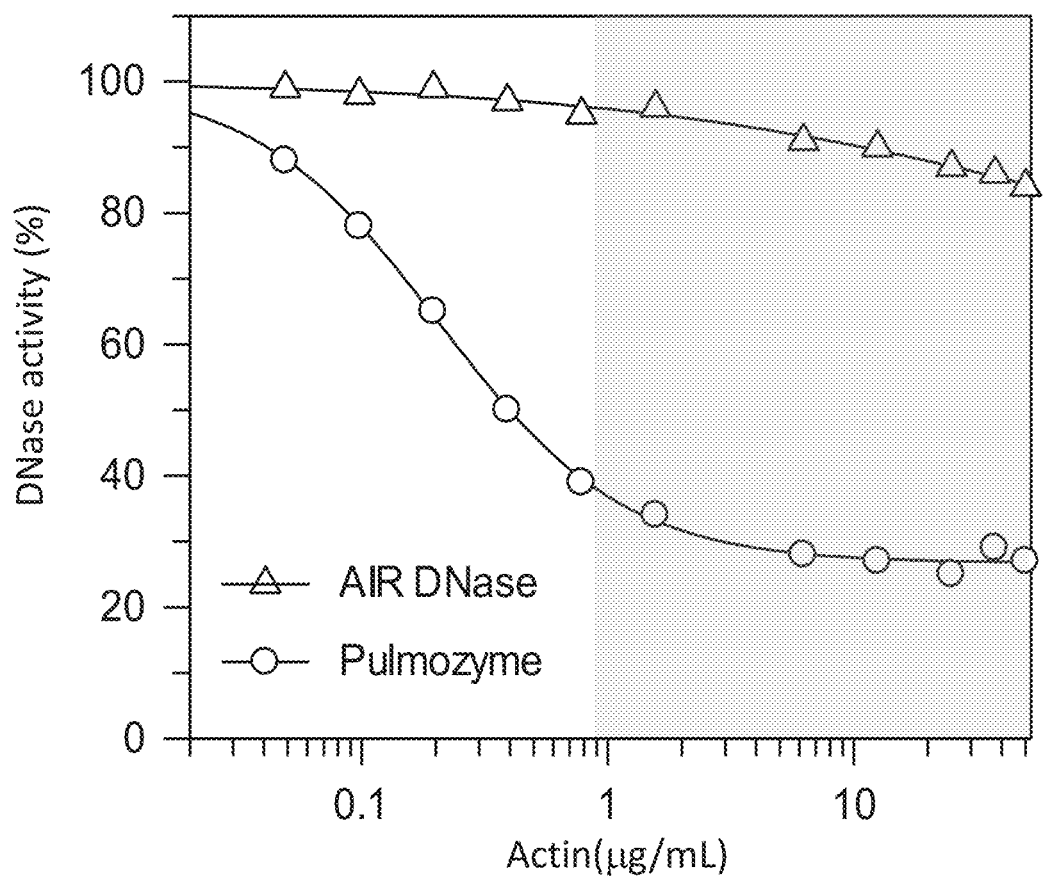
Figure 27:
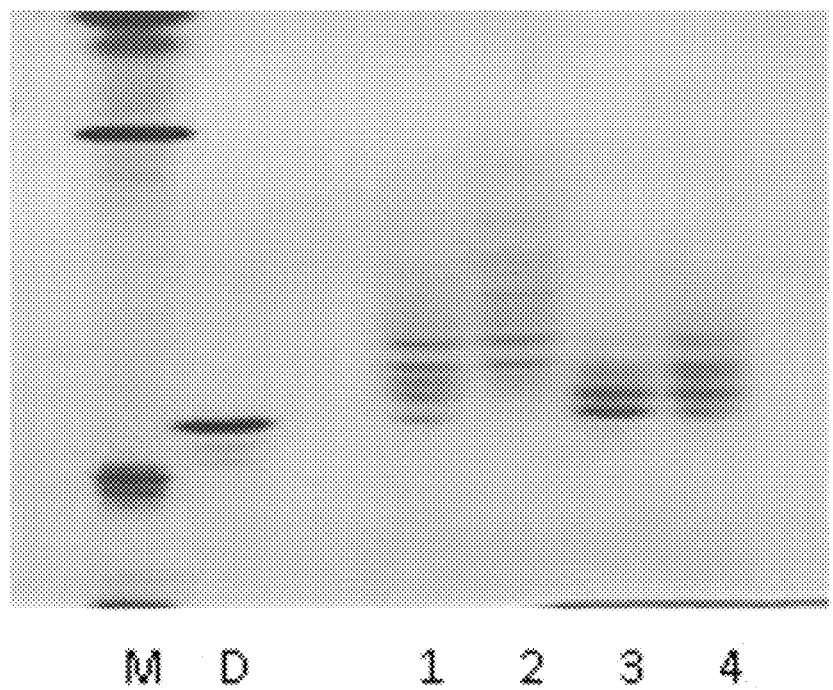
Figure 28:
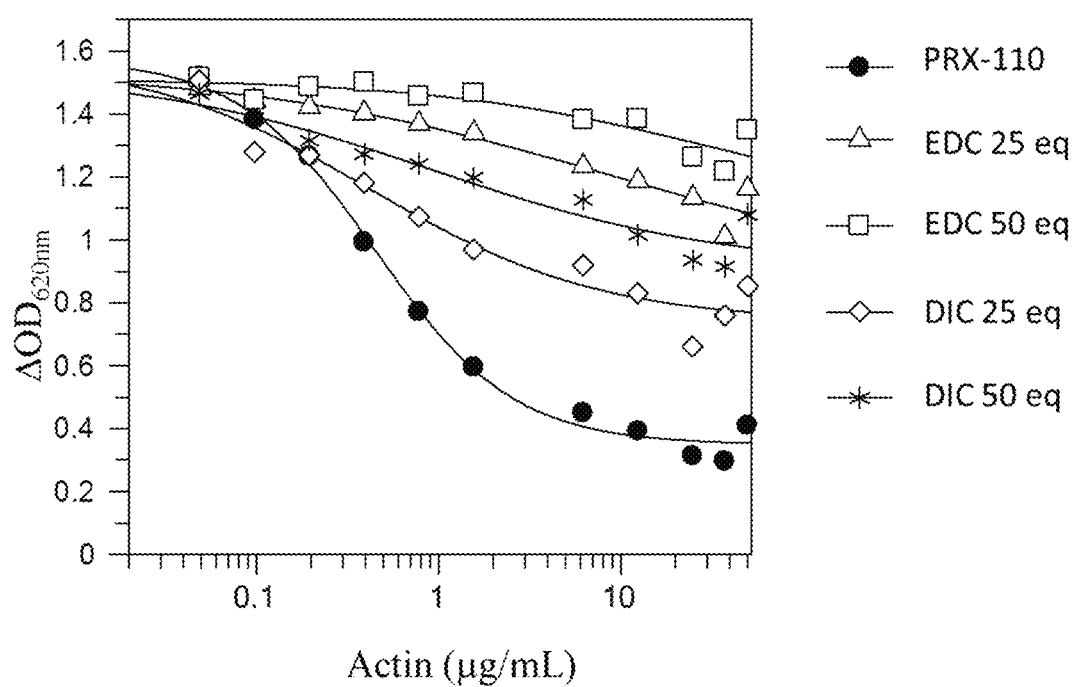
Figure 29:
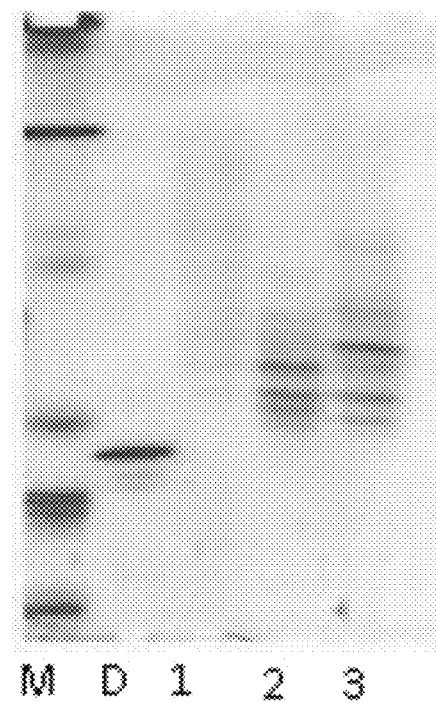
Figure 30:
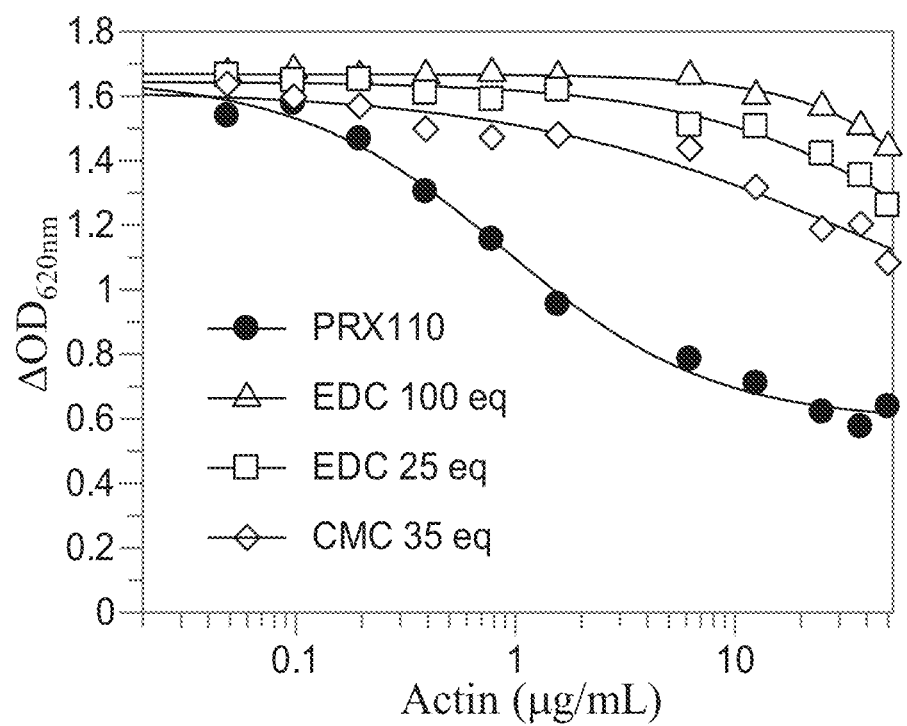
Figure 31A:
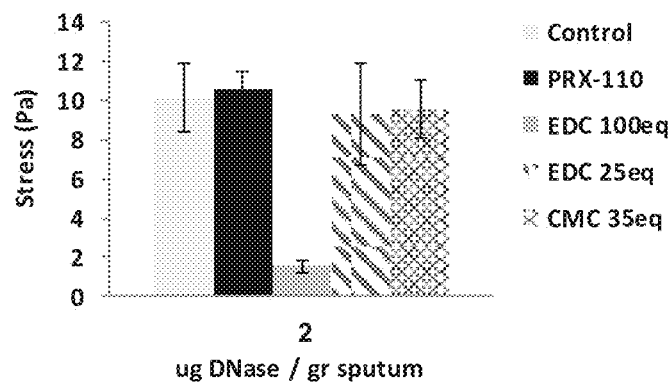
Figure 31B:
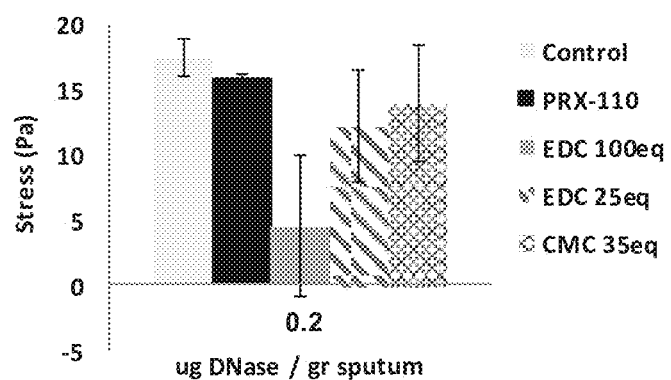
Figure 31C:
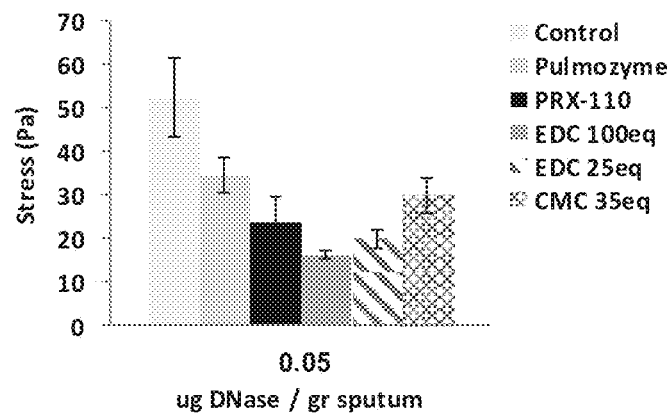
Figure 32:
Figure 33:
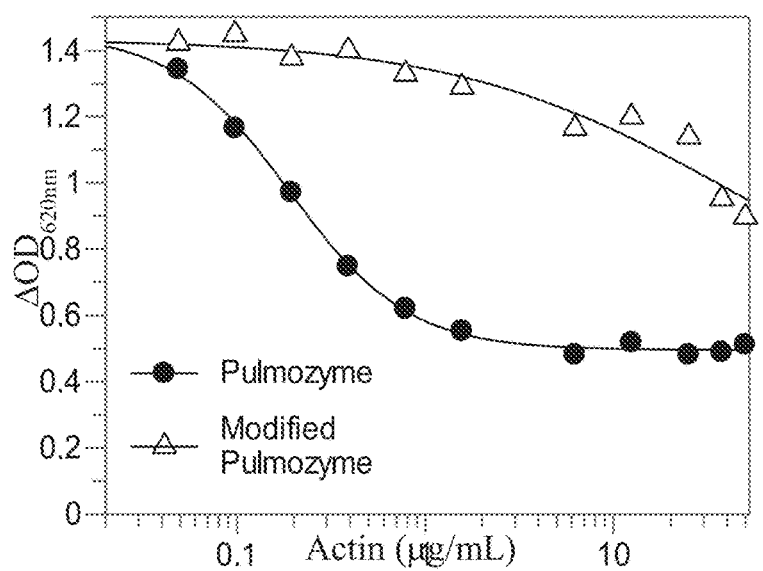
Figure 34:
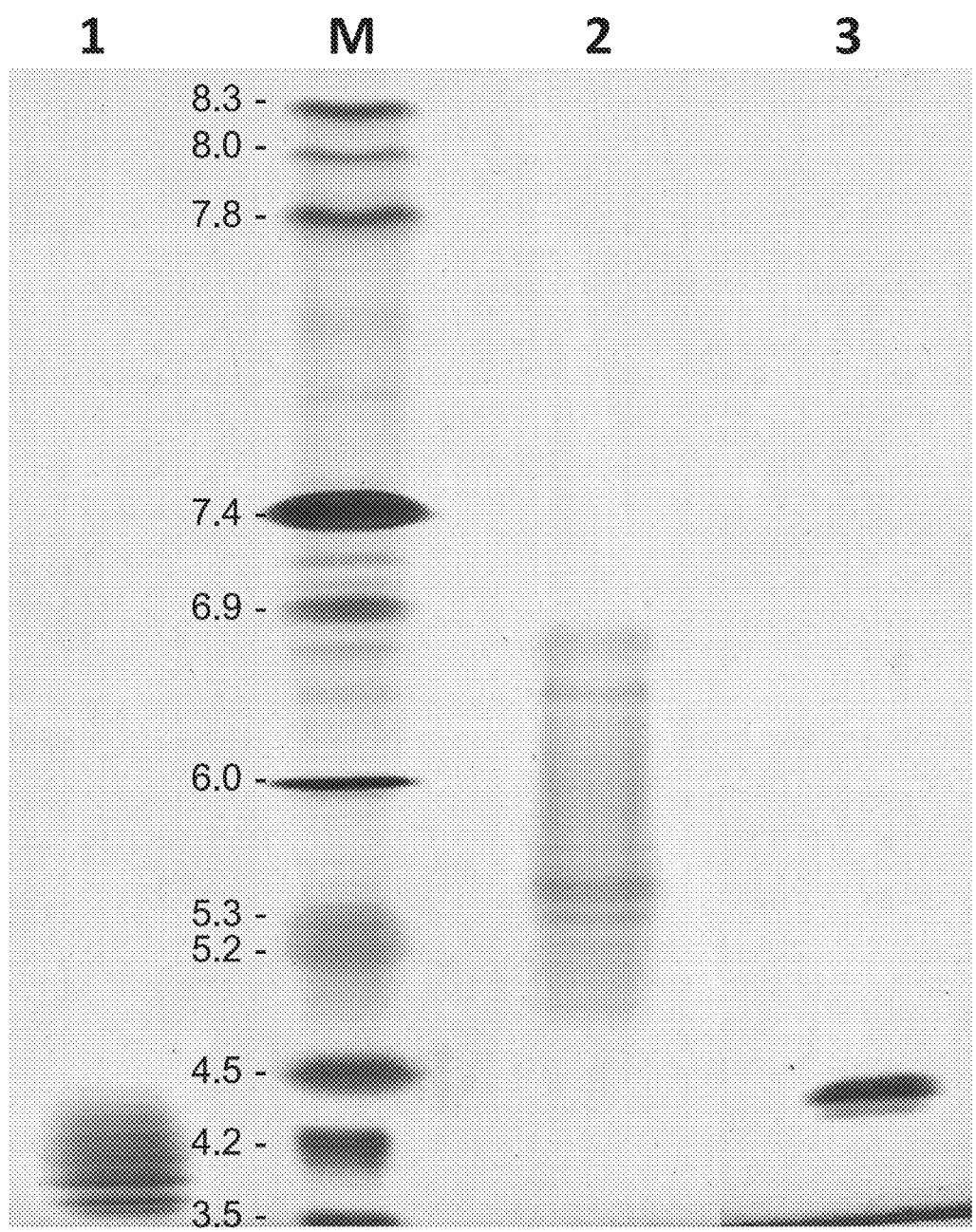
Figure 35:
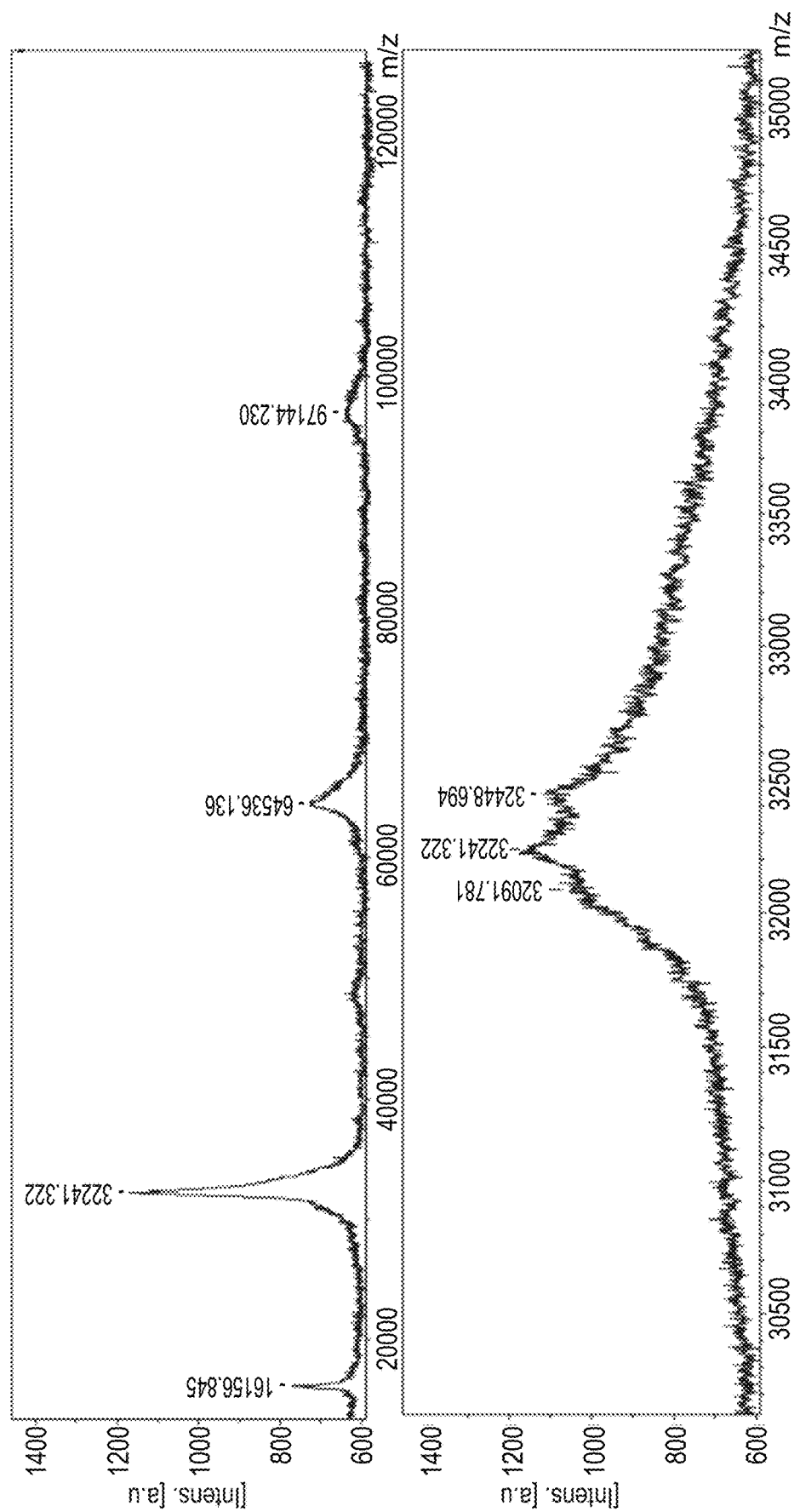
Figure 36:
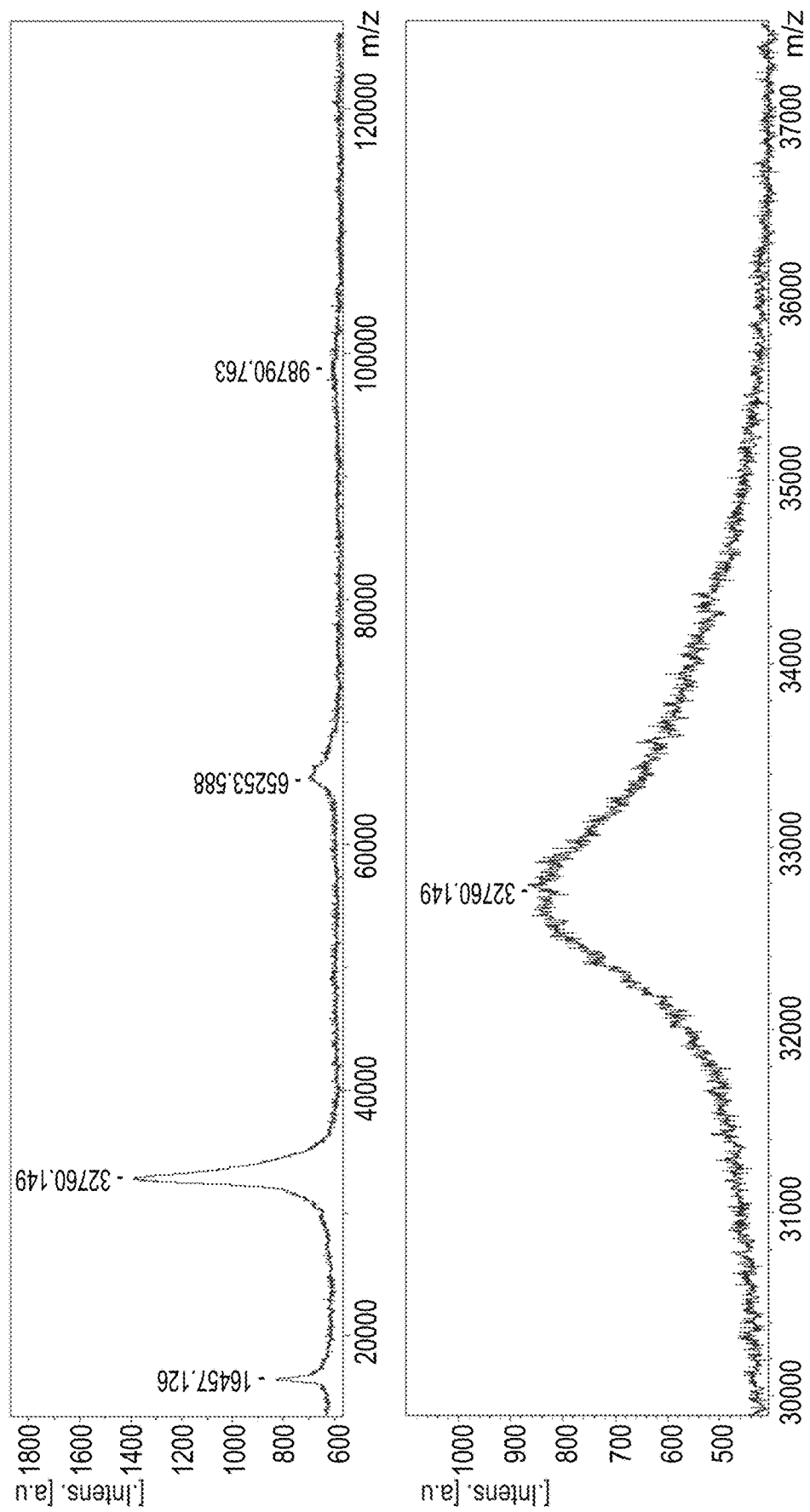
Figure 37:
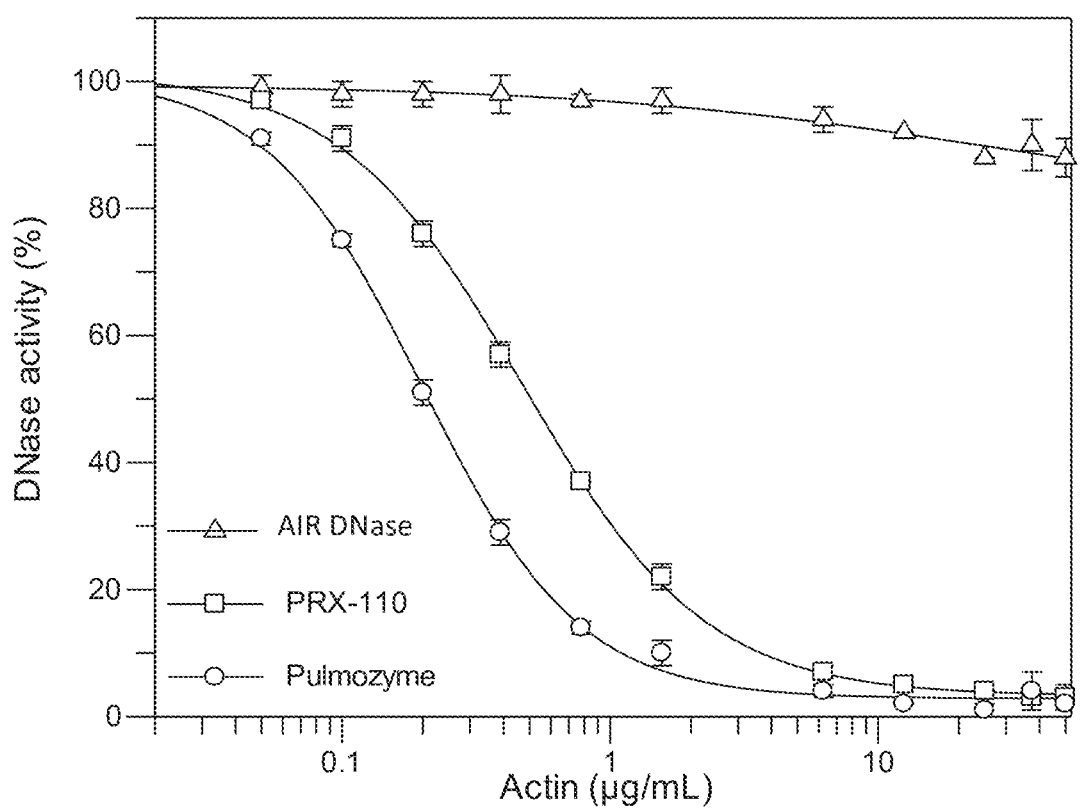
Figure 38A:
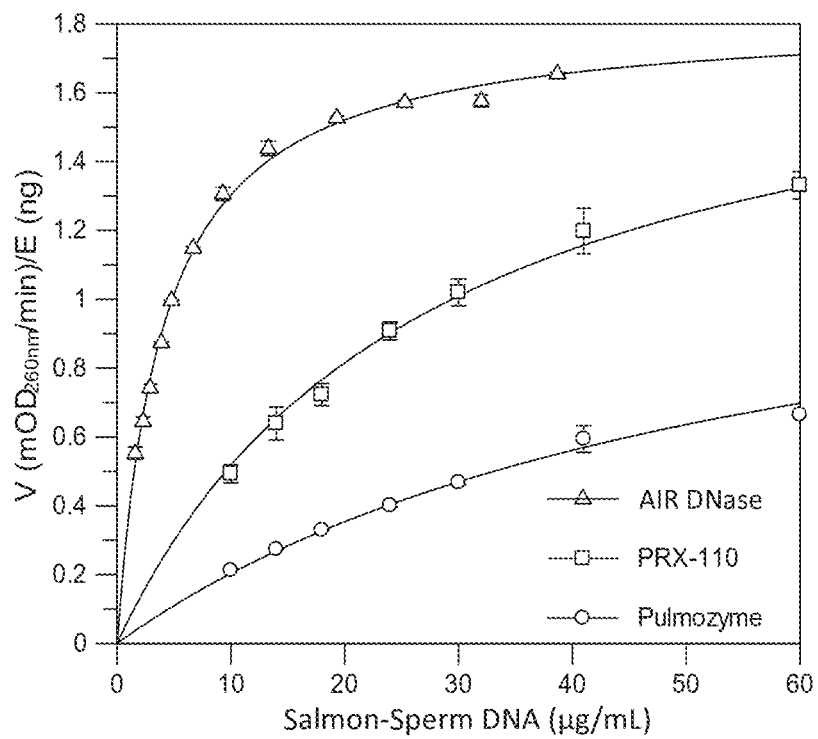
Figure 38B:
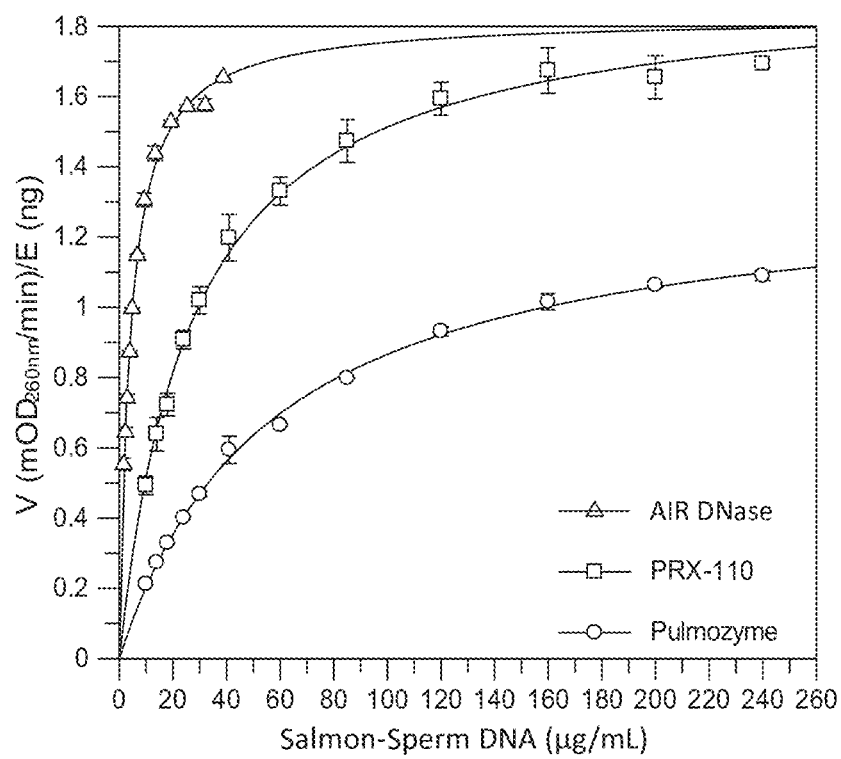
Figure 39A:
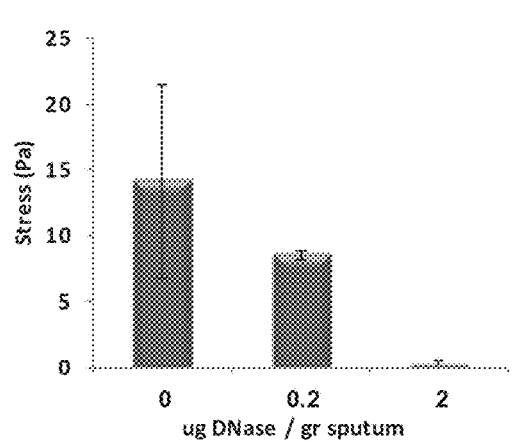
Figure 39B:
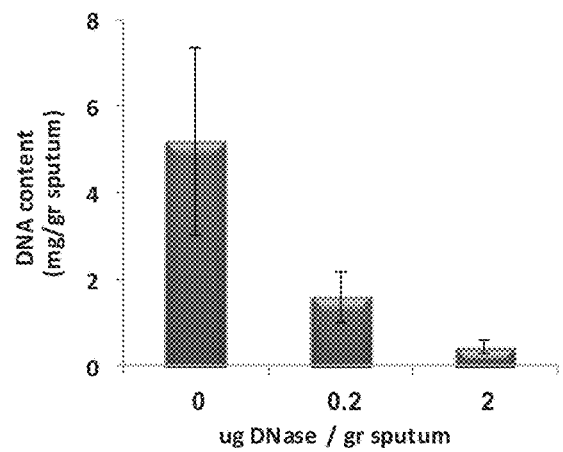
Figure 39C:
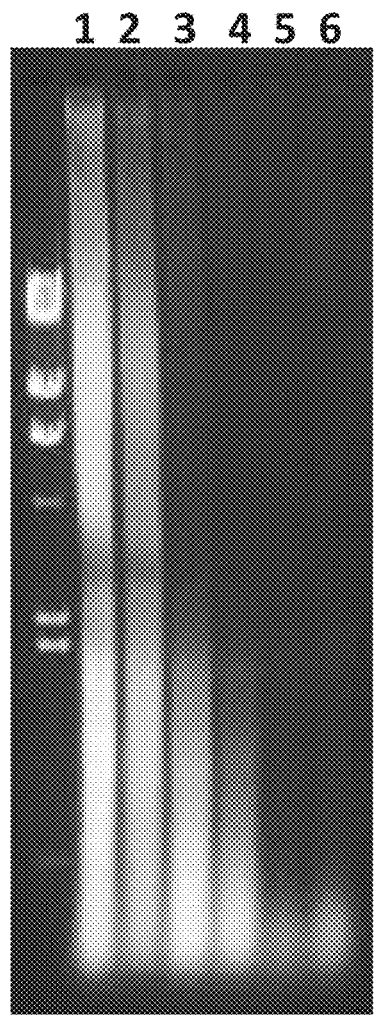
Figure 40A:
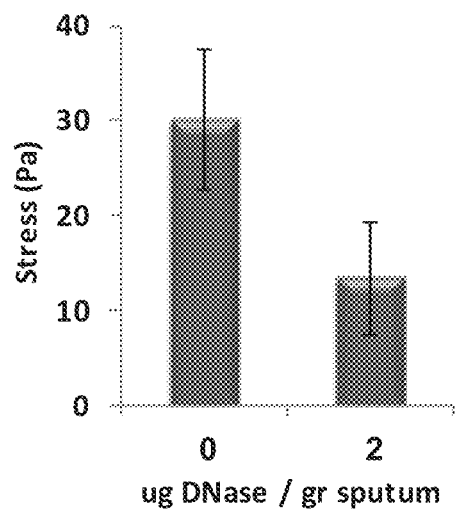
Figure 40B:
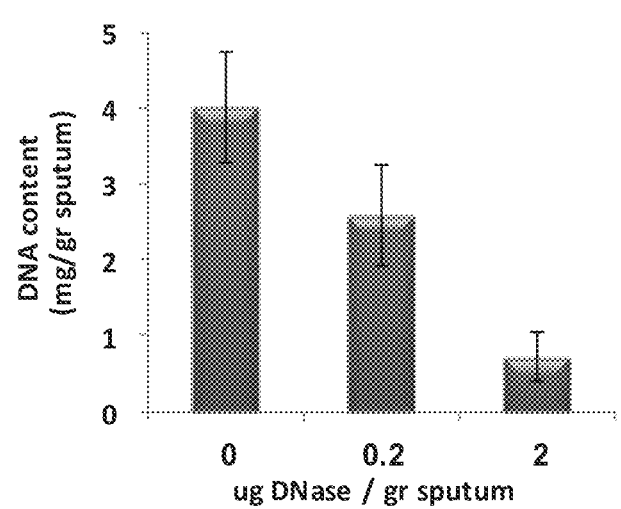
Figure 40C:
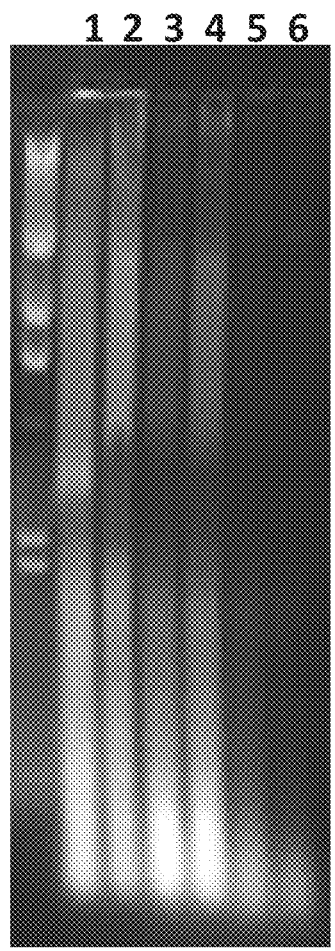

FIG. 9 is a bar graph showing DNase I concentration as determined by optical density (right hand bar) and apparent DNase I concentration based on DNase I activity as determined by a methyl green assay (left-hand bar) in modified DNase I samples prepared by amidation with Tris (L171(1)) or ammonium chloride (L171(2)) according to some embodiments of the invention;

FIG. 10 is a graph showing DNase I activity as a function of actin concentration for DNase I modified by amidation with Tris (L171(1)) or ammonium chloride (L171(2)), and for non-modified recombinant human DNase I (standard);

FIG. 11 presents kinetic plots of initial velocity of enzymatic activity versus substrate concentration of DNase I modified by amidation with Tris (AIR DNase, referred to as L171(1) in FIGS. 9 and 10) according to some embodiments of the invention, and of non-modified plant recombinant human DNase I (PRX 110), as determined using a DNA hyperchromicity assay which measures an increase in the optical density (OD) at 260 nm as DNA is degraded;

FIGS. 12A and 12B present an image of a DNA electrophoresis gel (FIG. 12A) and a bar graph (FIG. 12B) showing DNA content in sputum (in units of mg DNA per gram sputum in FIG. 12B) treated with 2 μg per gram sputum of actin inhibition resistant DNase I (AIR DNase, lanes 3 and 4 in FIG. 12A) according to some embodiments of the invention, or with 2 μg (lanes 7 and 8 in FIG. 12A) or 5 μg (lanes 5 and 6 in FIG. 12A) per gram sputum of non-modified Pulmozyme® DNase I, or with no DNase I (0 μg per gram sputum);

FIG. 13 is a bar graph showing the stress (in Pa units) at which the elastic modulus (G') and viscous modulus (G") cross over (i.e., G'=G", phase angle=45°) in a sputum sample treated with 2 μg per gram sputum of actin inhibition resistant DNase I (AIR DNase) according to some embodiments of the invention, or with 2 or 5 μg per gram sputum of non-modified Pulmozyme® DNase I, or with no DNase I (0 μg per gram sputum) (each value represents at least 2 measurements);

FIG. 14 is a bar graph showing DNA content in sputum (in units of mg DNA per gram sputum) from each of 19 patients, the sputum being treated with 2 μg per gram sputum of actin inhibition resistant DNase I according to some embodiments of the invention (AIR DNase, right-hand bars) or non-modified recombinant human DNase I (rhDNase I, middle bars), or without DNase (control, left-hand bars);

FIG. 15 presents bar graphs showing DNA content in sputum (in units of mg DNA per gram sputum) from each of 3 patients, the sputum being treated with 2 μg per gram sputum of actin inhibition resistant DNase I according to some embodiments of the invention (AIR DNase, right-hand bars), or 2 or 5 μg per gram sputum non-modified Pulmozyme® DNase I, or without DNase (0 μg per gram sputum);

FIGS. 16A-16D are each bar graphs showing the stress (in Pa units) at which the elastic modulus (G') and viscous modulus (G") cross over (i.e., G'=G", phase angle=45°) in sputum samples from 26 patients treated with 2 μg (FIG. 16A), 0.2 μg (FIG. 16B), 20 μg (FIG. 16C) or 0.05 μg (FIG. 16D) per gram sputum of actin inhibition resistant DNase I (right-hand bars) according to some embodiments of the invention and non-modified recombinant human DNase I (middle bars), and without DNase (left-hand bars) (each value represents at least 2 measurements);

FIG. 17 is a diamond plot showing the stress (in Pa units) at which the elastic modulus (G') and viscous modulus (G") cross over (i.e., G'=G", phase angle=45°) in sputum samples from 6 patients treated with actin inhibition resistant DNase I (AIR DNase) according to some embodiments of the invention, and non-modified plant recombinant human DNase I (PRX-110) or dornase alfa (Pulmozyme®) DNase I (for each treatment group, average values are represented by line in middle of diamond, 95% confidence interval is represented by top and bottom of diamond, and individual data points for each sample are further shown);

FIG. 18 presents an image of an isoelectric focusing gel (pH 3-7) showing non-modified DNase I (lane D), and DNase I modified by amidation with ethylene diamine, using 25 or 50 equivalents of DIC (diisopropylcarbodiimide) (lanes 3 and 4, respectively), 25 or 50 equivalents of CMC (N-cyclohexyl-N'-(2-morpholinoethyl)carbodiimide metho-p-toluenesulfonate) (lanes 5 and 6, respectively) or 50 or 100 equivalents of DTC (di-t-butylcarbodiimide) (lanes 1 and 2, respectively), according to some embodiments of the invention (pH markers in lane M);

FIG. 19 presents an image of a polyacrylamide (12%) electrophoresis gel (SDS-PAGE) showing non-modified DNase I (lane D), and DNase I modified by amidation with ethylene diamine, using 25 or 50 equivalents of DIC (diisopropylcarbodiimide) (lanes 3 and 4, respectively), 25 or 50 equivalents of CMC (N-cyclohexyl-N'-(2-morpholinoethyl) carbodiimide metho-p-toluenesulfonate) (lanes 5 and 6, respectively) or 50 or 100 equivalents of DTC (di-t-butyl-carbodiimide) (lanes 1 and 2, respectively), according to some embodiments of the invention (molecular weight markers in lane M);

FIG. 20 presents an image of an isoelectric focusing gel (pH 3-7) showing DNase I modified by amidation with ethylene diamine, using 35 equivalents of CMC (N-cyclohexyl-N'-(2-morpholinoethyl)carbodiimide metho-p-toluenesulfonate) in MES (2-(N-morpholino)ethanesulfonic acid) buffer with a pH of 4 (lane 1), 4.5 (lane 2), 5 (lane 3), 5.5 (lane 4) or 6 (lane 5), according to some embodiments of the invention (pH markers in lane M);

FIG. 21 presents an image of a polyacrylamide (12%) electrophoresis gel (SDS-PAGE) showing DNase I modified by amidation with ethylene diamine, using 35 equivalents of CMC (N-cyclohexyl-N'-(2-morpholinoethyl)carbodiimide metho-p-toluenesulfonate) in MES (2-(N-morpholino)ethanesulfonic acid) buffer with a pH of 4 (lane 1), 4.5 (lane 2), 5 (lane 3), 5.5 (lane 4) or 6 (lane 5), according to some embodiments of the invention (molecular weight markers in lane M);

FIG. 22 presents an image of an isoelectric focusing gel (pH 3-10) showing non-modified DNase I (lane D), and DNase I modified by amidation with ethylene diamine and CMC (N-cyclohexyl-N'-(2-morpholinoethyl)carbodiimide metho-p-toluenesulfonate) at a temperature of 12° C. (lane 1), 16° C. (lane 2), 20° C. (lane 3) or 25° C. (lane 4), according to some embodiments of the invention (pH markers in lane M);

FIG. 23 presents an image of an isoelectric focusing gel (pH 3-10) showing non-modified DNase I (lane D), and DNase I modified by amidation by reaction with ethylene diamine and CMC (N-cyclohexyl-N'-(2-morpholinoethyl) carbodiimide metho-p-toluenesulfonate) for 2.5 hours (lane 1), 2 hours (lane 2), 1.75 hours (lane 3), 1.5 hours (lane 4) or 1 hour (lane 5), according to some embodiments of the invention (pH markers in lane M);

FIG. 24 presents an image of an isoelectric focusing gel (pH 3-10) showing non-modified DNase I (lane D), and DNase I modified by amidation by reaction with CMC (N-cyclohexyl-N'-(2-morpholinoethyl)carbodiimide metho-p-toluenesulfonate) and 100 (lane 1), 500 (lane 2), 1,000 (lane 3), 2,000 (lane 4), 4,000 (lane 5) or 6,000 (lane 6) equivalents of ethylene diamine, according to some embodiments of the invention (pH markers in lane M);

FIG. 25 presents an image of an isoelectric focusing gel (pH 3-10) showing non-modified DNase I (lane 1), and DNase I modified by amidation with ethylene diamine, using 35 (lanes 2 and 6), 45 (lanes 3 and 7), 55 (lanes 4 and 8) or 65 (lanes 5 and 9) equivalents of CMC (N-cyclohexyl-N'-(2-morpholinoethyl)carbodiimide metho-p-toluenesulfonate), in the presence of 0 (lanes 2-5) or 2 mM (lanes 6-9) of calcium ions (pH markers and indicated pH values in lane M);

FIG. 26 is a graph showing DNase I activity as a function of actin concentration for DNase I modified by amidation with ethylene diamine (AIR DNase) as well and for non-modified Pulmozyme® DNase I (DNase I concentration was 45 ng/ml; shaded area represents actin concentration (at least 0.93 µg/ml) where the ratios of actin to DNase concentration (45 ng/ml) correlate to ratios found in pulmonary mucus of treated cystic fibrosis patients);

FIG. 27 presents an image of an isoelectric focusing gel (pH 3-7) showing non-modified DNase I (lane D), and DNase I modified by amidation with Tris, using 25 or 50 equivalents of EDC (1-ethyl-3-(3-dimethylaminopropyl)carbodiimide; lanes 1 and 2, respectively) or 25 or 50 equivalents of DIC (diisopropylcarbodiimide; lanes 3 and 4, respectively), according to some embodiments of the invention (pH markers in lane M);

FIG. 28 is a graph showing DNase I activity as a function of actin concentration for non-modified DNase I (PRX-110), and for DNase I modified by amidation with Tris using 25 or 50 equivalents of EDC (1-ethyl-3-(3-dimethylaminopropyl)carbodiimide) or DIC (diisopropylcarbodiimide);

FIG. 29 presents an image of an isoelectric focusing gel (pH 3-7) showing non-modified DNase I (lane D), and DNase I modified by amidation with 100 mM (lane 1) or 100 equivalents (lanes 2 and 3) of Tris, using 25 (lane 2) or 100 (lane 1) equivalents of EDC (1-ethyl-3-(3-dimethylaminopropyl)carbodiimide) or 35 equivalents of CMC (N-cyclohexyl-N'-(2-morpholinoethyl)carbodiimide metho-p-toluenesulfonate; lane 3), according to some embodiments of the invention (pH markers in lane M);

FIG. 30 is a graph showing DNase I activity as a function of actin concentration for non-modified DNase I (PRX-110), and for DNase I modified by amidation with Tris, using 25 or 100 equivalents of EDC (1-ethyl-3-(3-dimethylaminopropyl)carbodiimide) or 35 equivalents of CMC (N-cyclohexyl-N'-(2-morpholinoethyl)carbodiimide metho-p-toluenesulfonate);

FIGS. 31A-31C are each bar graphs showing the stress (in Pa units) at which the elastic modulus (G') and viscous modulus (G") cross over (i.e., G'=G", phase angle=45°) in sputum samples from 3 patients (one in each of FIGS. 31A-31C) treated with 2 µg (FIG. 31A), 0.2 µg (FIG. 31B) or 0.05 µg (FIG. 31C) per gram sputum of DNase I modified by amidation with Tris, using 25 or 100 equivalents of EDC (1-ethyl-3-(3-dimethylaminopropyl)carbodiimide) or 35 equivalents of CMC (N-cyclohexyl-N'-(2-morpholinoethyl)carbodiimide metho-p-toluenesulfonate), according to some embodiments of the invention, or non-modified plant recombinant human DNase I (PRX-110; FIGS. 31A-31C) or Pulmozyme® DNase I (FIG. 31C), and without DNase (Control);

FIG. 32 presents an image of an isoelectric focusing gel (pH 3-7) showing non-modified Pulmozyme® DNase I (lane 1) and Pulmozyme® DNase I modified by amidation with Tris using 25 equivalents of EDC (1-ethyl-3-(3-dimethylaminopropyl)carbodiimide) (lane 2), according to some embodiments of the invention (pH markers in lane M);

FIG. 33 is a graph showing DNase I activity as a function of actin concentration for non-modified Pulmozyme® DNase I and for Pulmozyme® DNase I modified according to some embodiments of the invention by amidation with Tris using 25 equivalents of EDC (1-ethyl-3-(3-dimethylaminopropyl)carbodiimide);

FIG. 34 presents an image of an isoelectric focusing gel (pH 3-10) showing non-modified Pulmozyme® DNase I (lane 1) and plant recombinant human DNase I (lane 3), plant recombinant human DNase I modified by amidation with ethylene diamine and 60 equivalents of CMC (N-cyclohexyl-N'-(2-morpholinoethyl)carbodiimide metho-p-toluenesulfonate) (lane 2), according to some embodiments of the invention (pH markers and indicated pH values in lane M);

FIG. 35 presents a MALDI-ToF spectrum of non-modified plant recombinant human DNase I (lower panel shows a portion of the spectrum shown in the upper panel at a higher resolution);

FIG. 36 presents a MALDI-ToF spectrum of plant recombinant human DNase I modified by amidation with ethylene diamine and 60 equivalents of CMC (N-cyclohexyl-N'-(2-morpholinoethyl)carbodiimide metho-p-toluenesulfonate) according to some embodiments of the invention (lower panel shows a portion of the spectrum shown in the upper panel at a higher resolution);

FIG. 37 is a graph showing DNase I activity as a function of actin concentration for non-modified Pulmozyme® DNase I and plant recombinant human DNase I (PRX-110), and for plant recombinant human DNase I modified by amidation with ethylene diamine and 60 equivalents of CMC (N-cyclohexyl-N'-(2-morpholinoethyl)carbodiimide metho-p-toluenesulfonate) according to some embodiments of the invention (AIR DNase);

FIGS. 38A and 38B are graphs showing DNase I activity (as determined by rate of change in absorption at 260) as a function of salmon sperm DNA concentration for non-modified Pulmozyme® DNase I and plant recombinant human DNase I (PRX-110), and for plant recombinant human DNase I modified by amidation with ethylene diamine and 60 equivalents of CMC (N-cyclohexyl-N'-(2-morpholinoethyl)carbodiimide metho-p-toluenesulfonate) according to some embodiments of the invention (AIR DNase) (FIG. 38A presents a portion of the data presented in FIG. 38B at a higher resolution);

FIGS. 39A-39C present bar graphs showing the stress (in Pa units) at which the elastic modulus (G') and viscous modulus (G") cross over (i.e., G'=G", phase angle=45°) (FIG. 39A), the DNA content (FIG. 39B), and an image of a DNA electrophoresis gel showing DNA degradation (FIG. 39C) in sputum treated with 0.2 (lanes 3-4 in FIG. 39C) or 2 µg (lanes 5-6 in FIG. 39C) per gram sputum of actin inhibition resistant DNase I (AIR DNase) according to some embodiments of the invention, or with the AIR DNase I vehicle without DNase I (0 µg/gr in FIGS. 39A and 39B, and lanes 1-2 in FIG. 39C);

FIGS. 40A-40C present bar graphs showing the stress (in Pa units) at which the elastic modulus (G') and viscous modulus (G") cross over (i.e., G'=G", phase angle=45°) (FIG. 40A), the DNA content (FIG. 40B), and an image of a DNA electrophoresis gel showing DNA degradation (FIG.

Figure 42A:
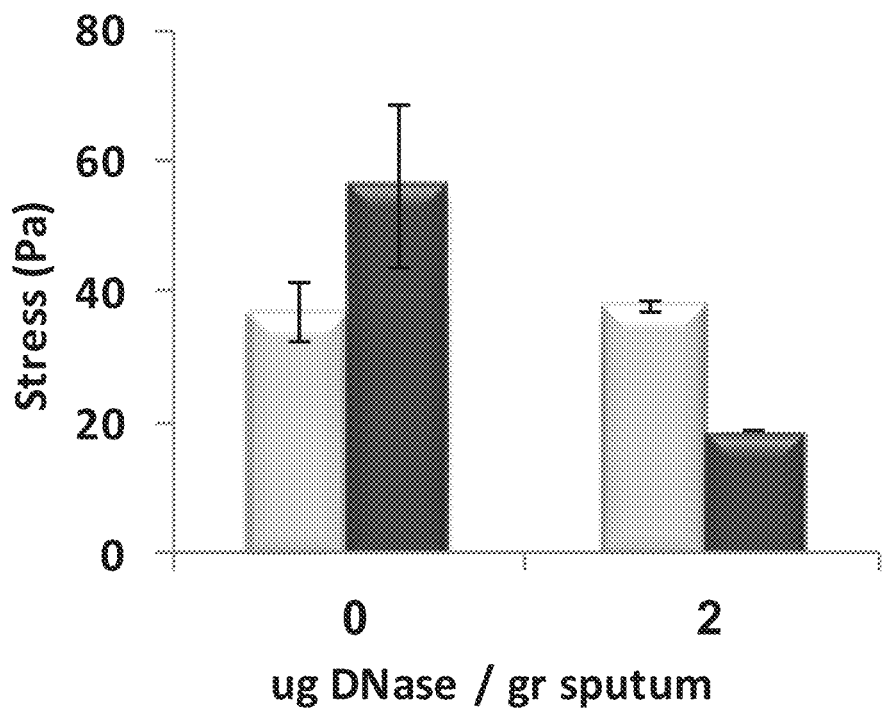
Figure 42B:
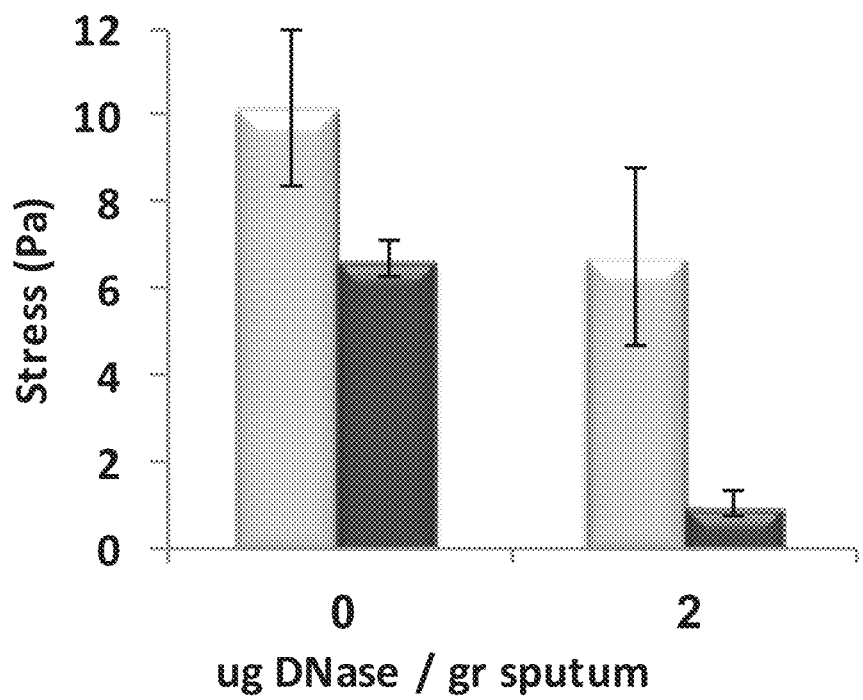
Figure 43A:
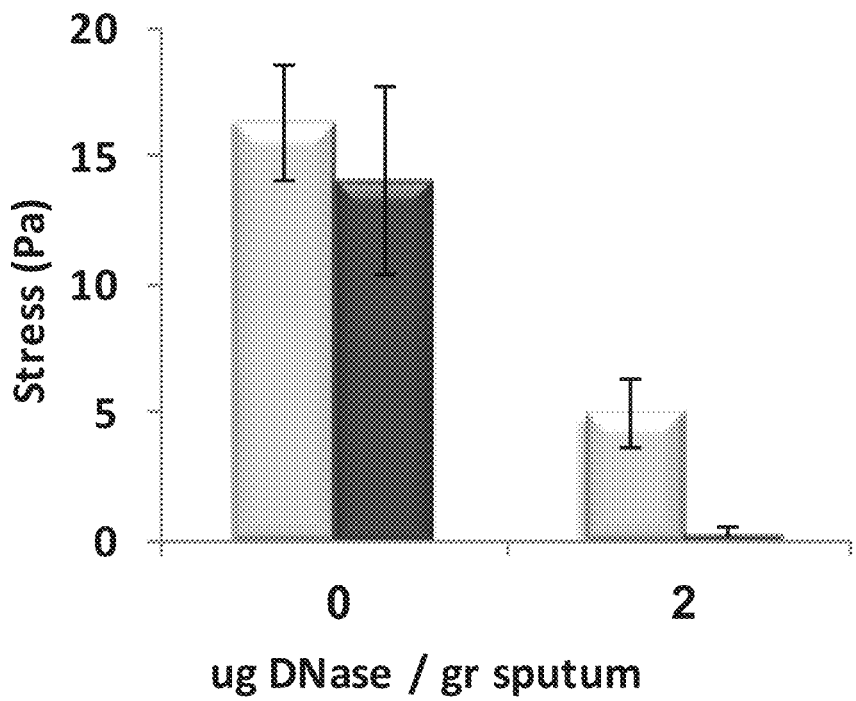
Figure 43B:
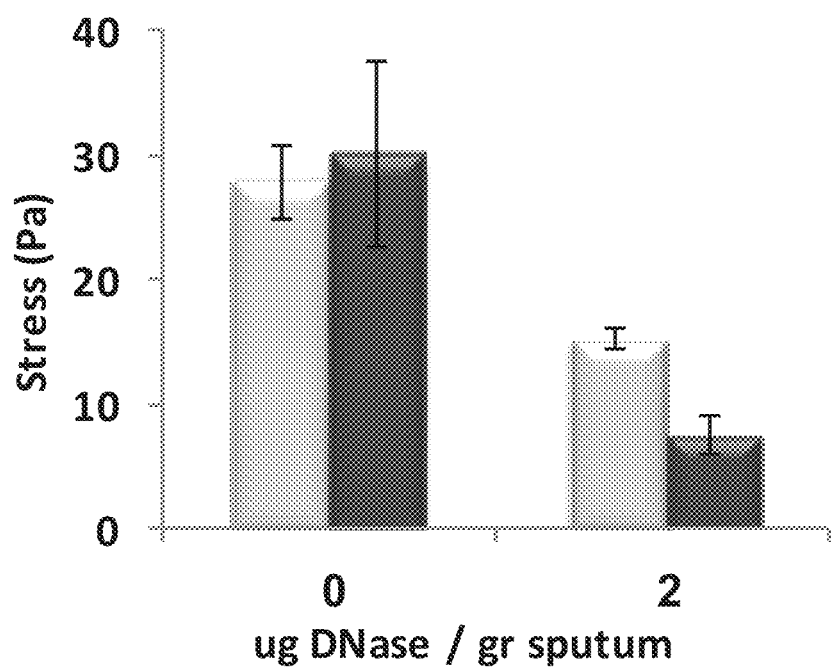
Figure 44A:
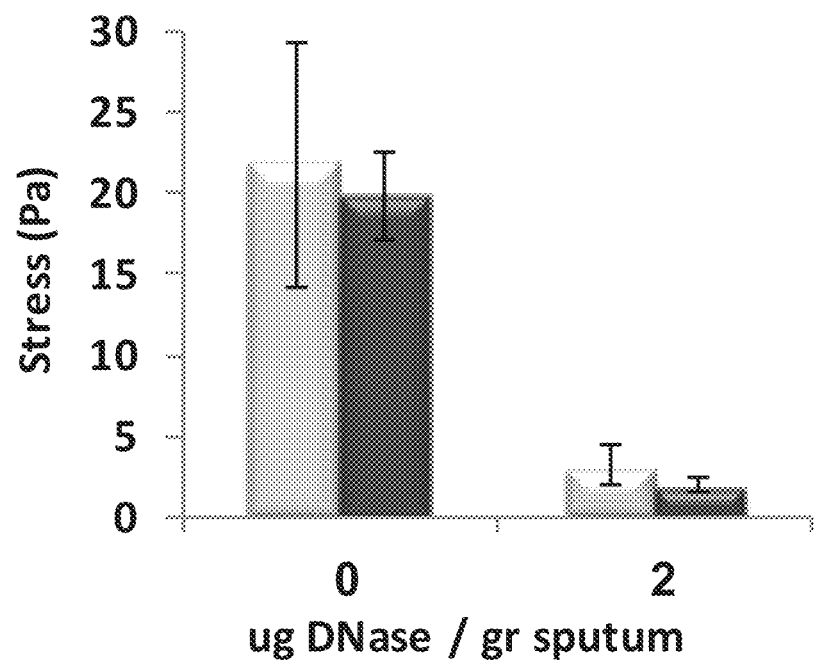
Figure 44B:
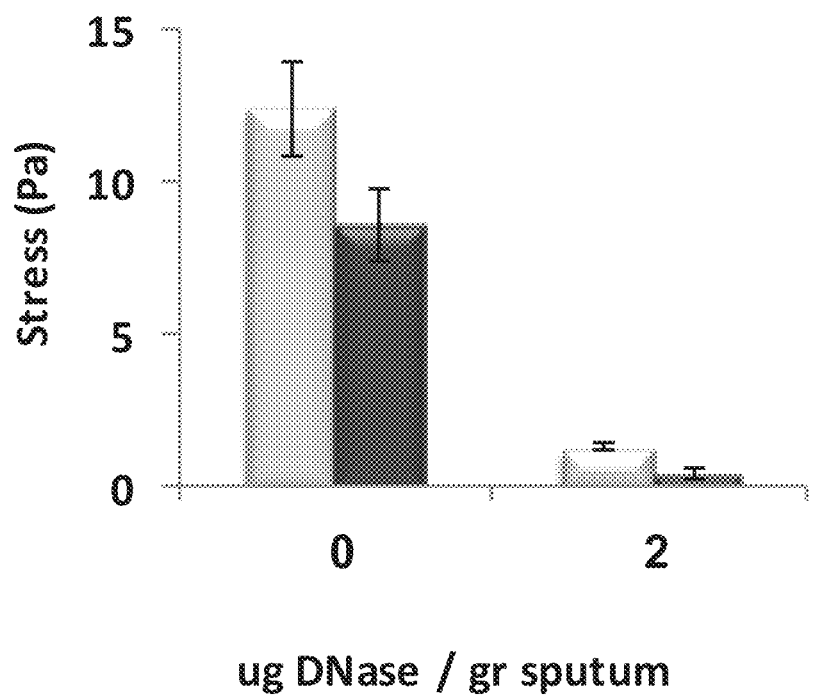
Figure 45A:
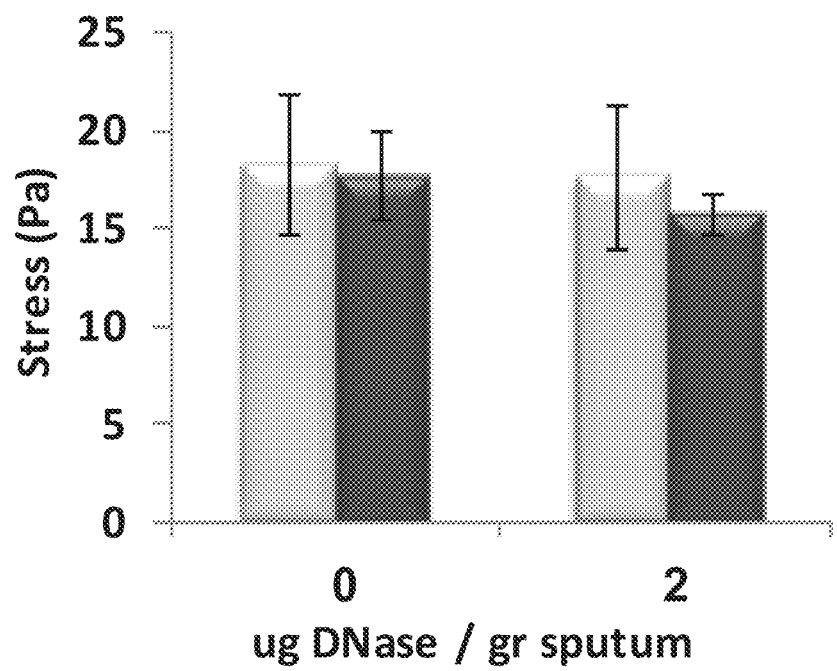
Figure 45B:
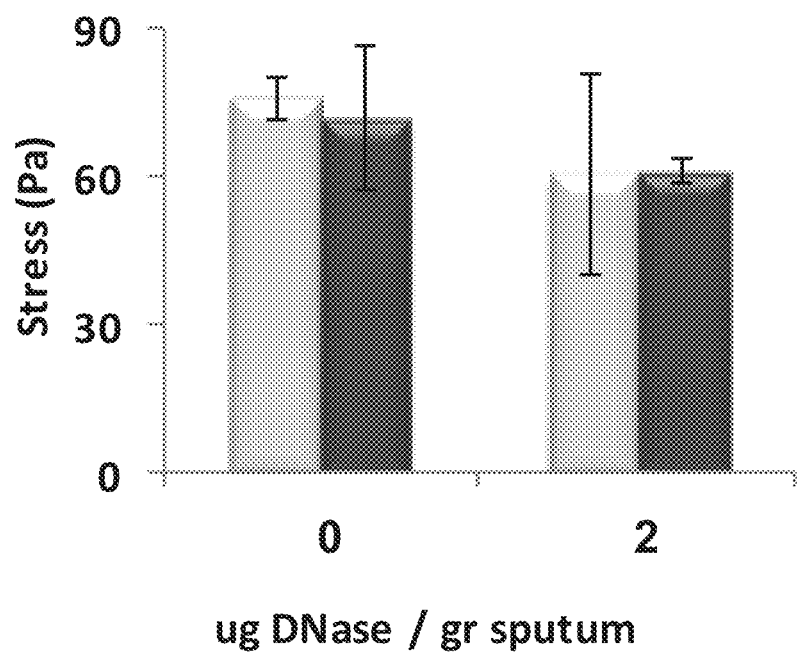
Figures 46, 47:
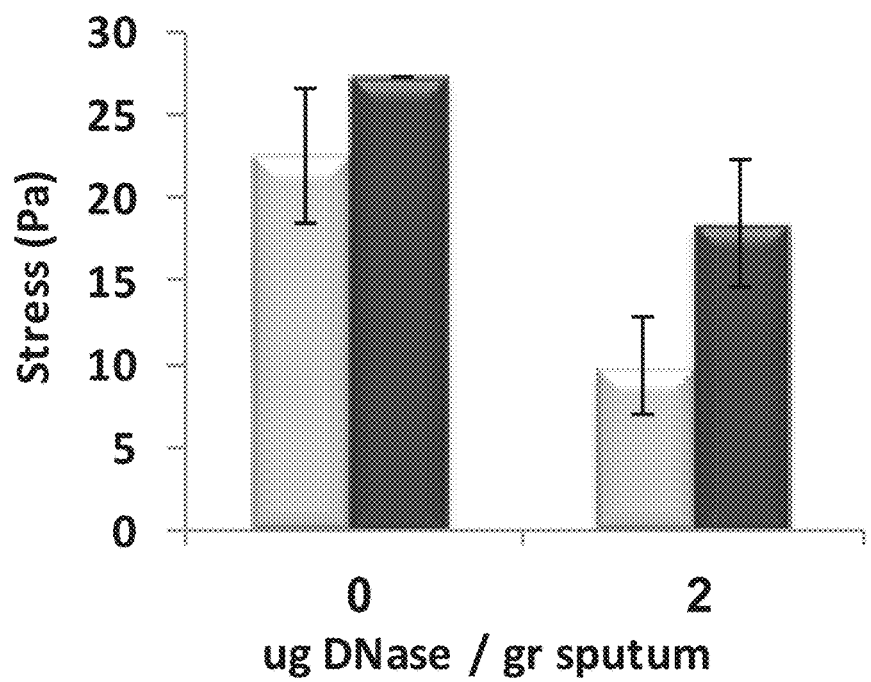
Figure 48:
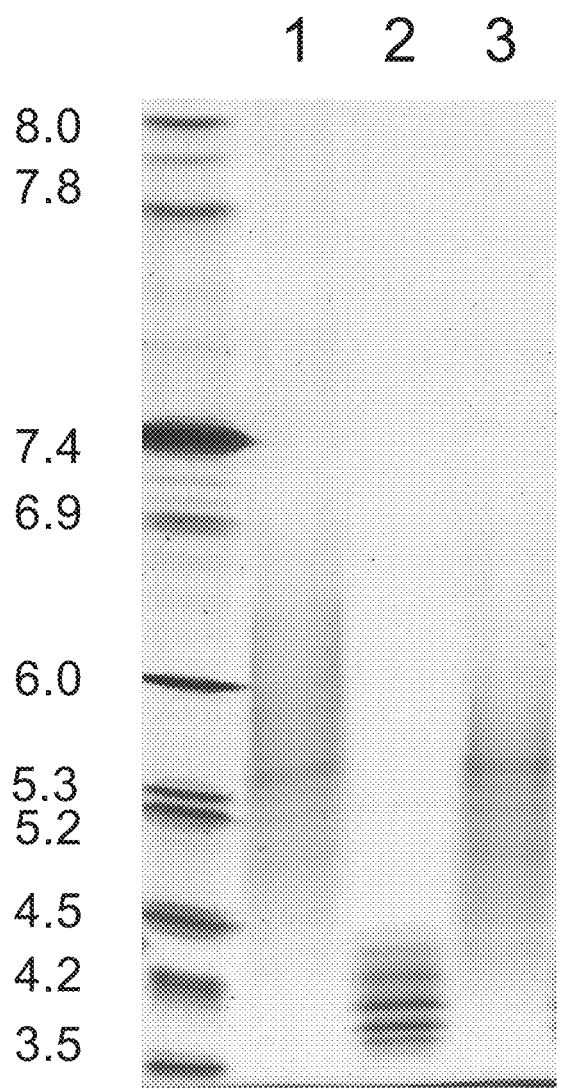
Figure 49:
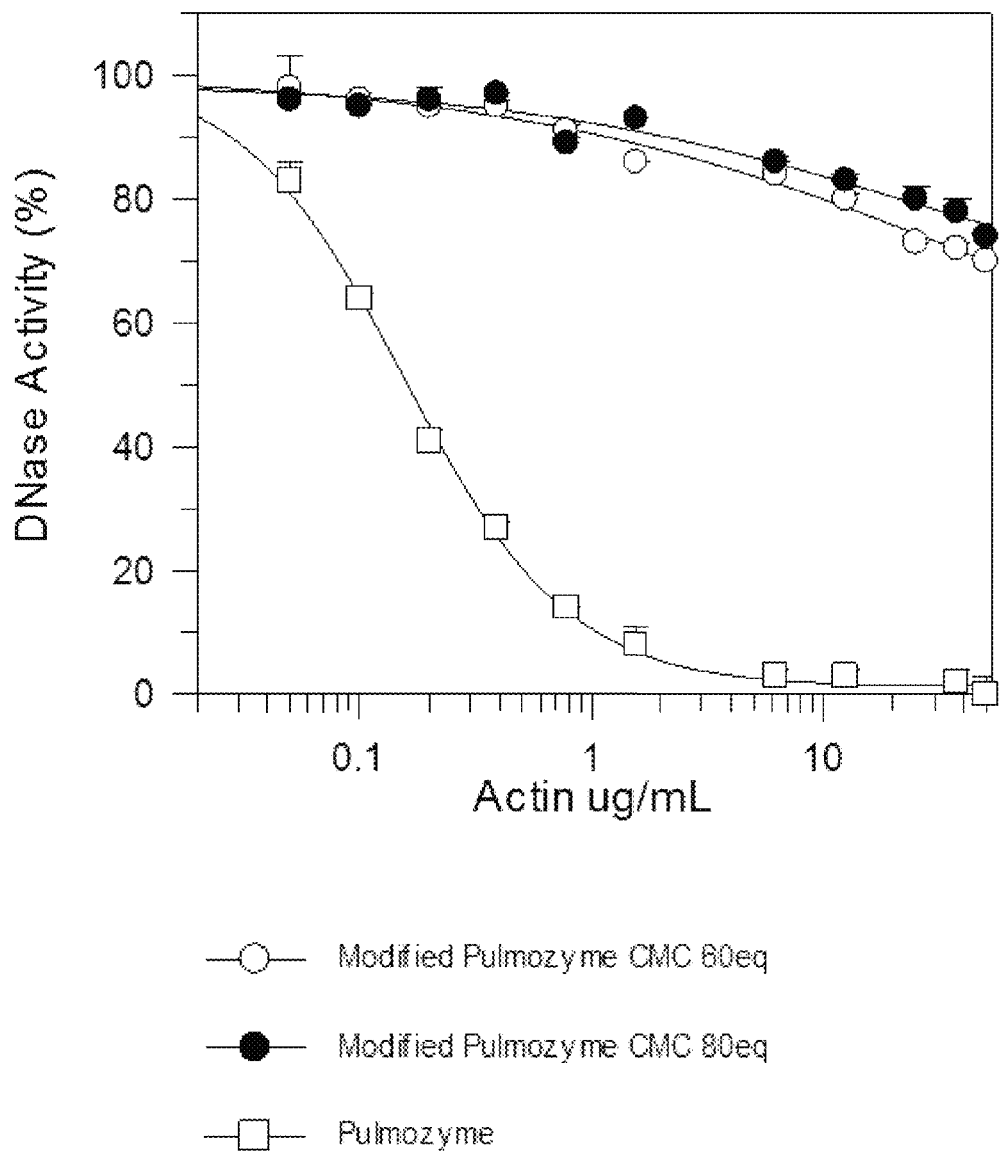

40C) in sputum treated with 0.2 (lanes 3-4 in FIG. 40C) or 2 μg (lanes 5-6 in FIG. 40C) per gram sputum of actin inhibition resistant DNase I (AIR DNase) according to some embodiments of the invention, or with the AIR DNase I vehicle without DNase I (0 μg/gr in FIGS. 40A and 40B, and lanes 1-2 in FIG. 40C);

FIGS. 41A-41C present bar graphs showing the stress (in Pa units) at which the elastic modulus (G') and viscous modulus (G") cross over (i.e., G'=G", phase angle=45°) (FIG. 41A), the DNA content (FIG. 41B), and an image of a DNA electrophoresis gel showing DNA degradation (FIG. 41C) in sputum treated with 2 μg per gram sputum of actin inhibition resistant DNase I (AIR DNase; lanes 7-8 in FIG. 41C) according to some embodiments of the invention, or of Pulmozyme® DNase I (lanes 3-4 in FIG. 41C), or with AIR DNase I vehicle (0 μg/gr AIR DNase in FIGS. 41A and 41B, and lanes 5-6 in FIG. 41C) or Pulmozyme® vehicle (0 μg/gr Pulmozyme® in FIGS. 41A and 41B, and lanes 1-2 in FIG. 41C);

FIGS. 42A and 42B are each a bar graph showing the stress (in Pa units) at which the elastic modulus (G') and viscous modulus (G") cross over (i.e., G'=G", phase angle=45°) in sputum treated 0 or 2 μg per gram sputum of actin inhibition resistant (AIR) DNase I according to some embodiments of the invention (dark bars) or Pulmozyme® DNase I (light bars) (FIGS. 42A and 42B show results for sputum samples obtained from different cystic fibrosis patients who are representative of patients whose sputum responded strongly to the AIR DNase I, but was not substantially affected by Pulmozyme® DNase I);

FIGS. 43A and 43B are each a bar graph showing the stress (in Pa units) at which the elastic modulus (G') and viscous modulus (G") cross over (i.e., G'=G", phase angle=45°) in sputum treated 0 or 2 μg per gram sputum of actin inhibition resistant (AIR) DNase I according to some embodiments of the invention (dark bars) or Pulmozyme® DNase I (light bars) (FIGS. 43A and 43B show results for sputum samples obtained from different cystic fibrosis patients who are representative of patients whose sputum responded strongly to the AIR DNase I, and weakly to Pulmozyme® DNase I);

FIGS. 44A and 44B are each a bar graph showing the stress (in Pa units) at which the elastic modulus (G') and viscous modulus (G") cross over (i.e., G'=G", phase angle=45°) in sputum treated 0 or 2 μg per gram sputum of actin inhibition resistant (AIR) DNase I according to some embodiments of the invention (dark bars) or Pulmozyme® DNase I (light bars) (FIGS. 44A and 44B show results for sputum samples obtained from different cystic fibrosis patients who are representative of patients whose sputum responded strongly to both the AIR DNase I and Pulmozyme® DNase I);

FIGS. 45A and 45B are each a bar graph showing the stress (in Pa units) at which the elastic modulus (G') and viscous modulus (G") cross over (i.e., G'=G", phase angle=45°) in sputum treated 0 or 2 μg per gram sputum of actin inhibition resistant (AIR) DNase I according to some embodiments of the invention (dark bars) or Pulmozyme® DNase I (light bars) (FIGS. 45A and 45B show results for sputum samples obtained from different cystic fibrosis patients who are representative of patients whose sputum was not substantially affected by either the AIR DNase I or Pulmozyme® DNase I);

FIG. 46 is a bar graph showing the stress (in Pa units) at which the elastic modulus (G') and viscous modulus (G") cross over (i.e., G'=G", phase angle=45°) in a single atypical sample of sputum treated 0 or 2 μg per gram sputum of actin inhibition resistant (AIR) DNase I according to some embodiments of the invention (dark bars) or Pulmozyme® DNase I (light bars) (sputum sample was atypical in that the response to Pulmozyme® DNase I was stronger than the response to the AIR DNase I);

FIG. 47 presents the glycan structures present in exemplary samples of AIR DNase and their relative amounts (M or white circle indicate mannose; Fc(3) or diamond with dot indicate α(1-3) linked core fucose; X or white triangle indicate xylose; A or black square indicate GlcNAc; solid lines indicate β-linkage; dotted lines indicate α-linkage; horizontal lines indicate 1-4 linkage; upward-angled diagonal (/) lines indicate 1-3 linkage; downward-angled diagonal (\) lines indicate 1-6 linkage; vertical lines indicate 1-2 linkage; wavy line indicates 1-3 or 1-6 linkage; minor amounts represent approximately 1-5%; major amounts represent approximately 40-60%);

FIG. 48 presents an image of an isoelectric focusing gel (pH 3-10) showing non-modified Pulmozyme® DNase I (lane 2), and Pulmozyme® DNase I modified with ethylene diamine using 60 (lane 3) or 80 (lane 1) molar equivalents of CMC (pH markers in left-most lane); and FIG. 49 is a graph showing DNase I activity as a function of actin concentration for non-modified Pulmozyme® DNase I (Pulmozyme) and Pulmozyme® DNase I modified by amidation with ethylene diamine and 60 molar equivalents (60 eq) or 80 molar equivalents (80 eq) of CMC according to some embodiments of the invention.

DESCRIPTION OF SPECIFIC EMBODIMENTS OF THE INVENTION

The present invention, in some embodiments thereof, relates to therapy, and more particularly, but not exclusively, to non-cellularly modified DNase I protein, to processes of preparing same, and to therapeutic uses thereof. Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have uncovered that DNase I can be post-translationally modified (synthetically, non-cellularly, modified after translation) so as to exhibit both substantial enzymatic (e.g., hydrolytic) activity of DNase I (e.g., DNA hydrolysis), as well as resistance to inactivation of the enzymatic activity in the presence of actin. The modified DNase I is particularly suitable for degrading DNA in an environment in which actin is present, such as DNA in secretions, fluids and tissues.

While reducing the present invention to practice, the inventors have shown that chemical replacement of carboxylic acid groups in DNase I with amide groups results in a surprisingly high degree of resistance to inactivation by actin, while substantially maintaining the ability of DNase I to hydrolyze DNA. The inventors have further shown the efficacy of the modified DNase I at reducing viscosity of sputum and disrupting the elastic structure of sputum, which is useful for treating a variety of medical conditions, including cystic fibrosis.

Figure 1:
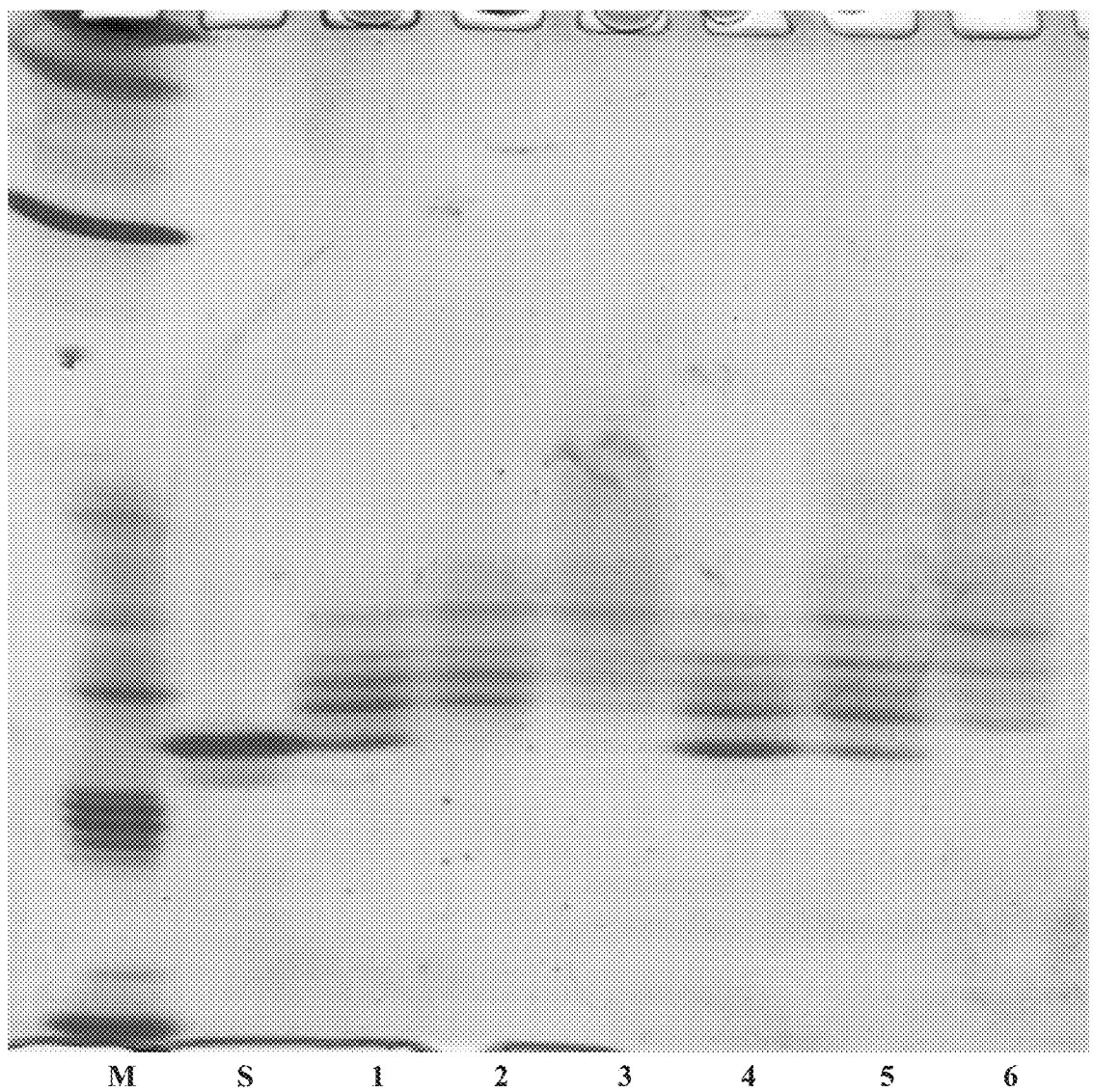
FIG. 1 presents an image of an isoelectric focusing gel (pH 3-10) showing DNase I standard (lane S), and DNase I modified by amidation with ethylene diamine (lanes 1-3) or hexamethylene diamine (lanes 4-6) and 25 (lanes 1 and 4), 50 (lanes 2 and 5) or 100 (lanes 3 and 6) equivalents of EDC (1-ethyl-3-(3-dimethylaminopropyl)carbodiimide), according to some embodiments of the invention (pH markers in lane M)
Figure 2:
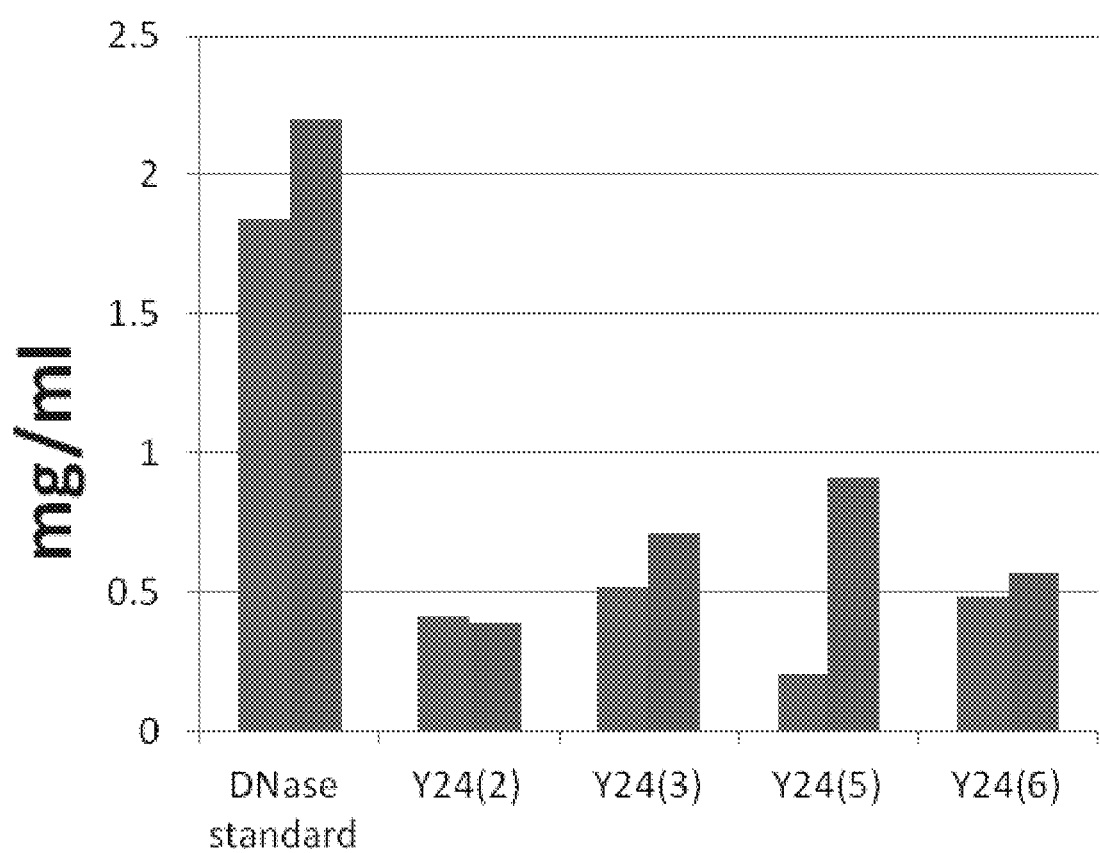
FIG. 2 is a bar graph showing DNase I concentration as determined by optical density (right hand bars) and apparent DNase I concentration based on DNase I activity as determined by a methyl green assay (left-hand bars) in modified DNase I samples prepared by amidation with ethylene diamine (Y24(2) and Y24(3)) or hexamethylene diamine (Y24(4) and Y24(5)) according to some embodiments of the invention and in a non-modified DNase standard.

Referring now to the drawings, FIGS. 1, 34 and 48 show DNase I from different sources (plant recombinant human DNase I and mammalian recombinant human DNase I) modified by amidation with diamines, to form an amide group with a free amine group. FIGS. 18-25 show the modified DNase I exhibiting various degrees of amidation by diamine under various reaction conditions. FIG. 2 shows that DNase modified by amidation with diamines substantially maintained DNase I enzymatic activity. FIGS. 26, 37 and 49 show that DNase from different sources (mammalian recombinant human DNase I and plant recombinant human DNase I) modified by amidation with a diamine exhibits resistance to inactivation by actin. Similar results were obtained using butylamine, a monoamine (data not shown). FIGS. 39A-46 show that DNase I modified by amidation with a diamine was considerably more effective than non-modified DNase I at hydrolyzing DNA in sputum and at disrupting the elastic structure of sputum.

FIGS. 38A-38B show that DNase I chemically modified by amidation with a diamine enhanced the enzymatic potency of the DNase as well as the affinity of the DNase to DNA, even in the absence of actin.

Figure 3:
FIG. 3 presents an image of an isoelectric focusing gel (pH 3-10) showing non-modified DNase I (DNase), and DNase I modified using EDC with (lane 2) and without (lane 1) addition of ethanolamine (pH markers in lane M)
Figure 4:
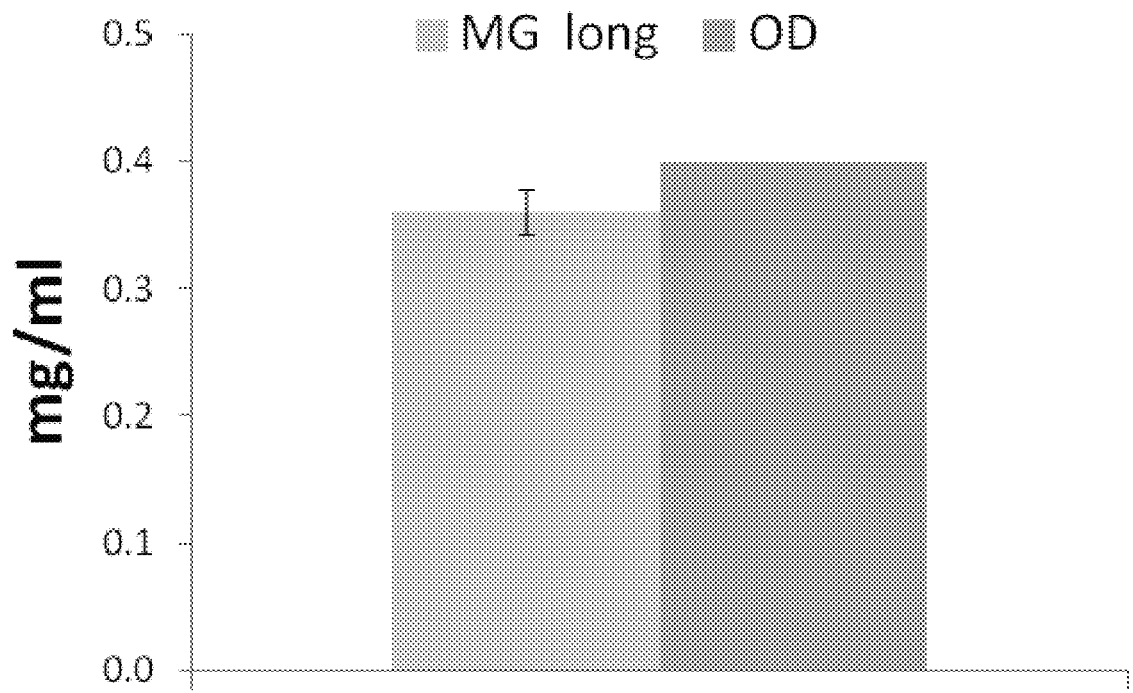
FIG. 4 is a bar graph showing DNase I concentration as determined by optical density (right hand bar) and apparent DNase I concentration based on DNase I activity as determined by a methyl green assay (left-hand bar) in a modified DNase I sample prepared by amidation with ethanolamine according to some embodiments of the invention.
Figure 5:
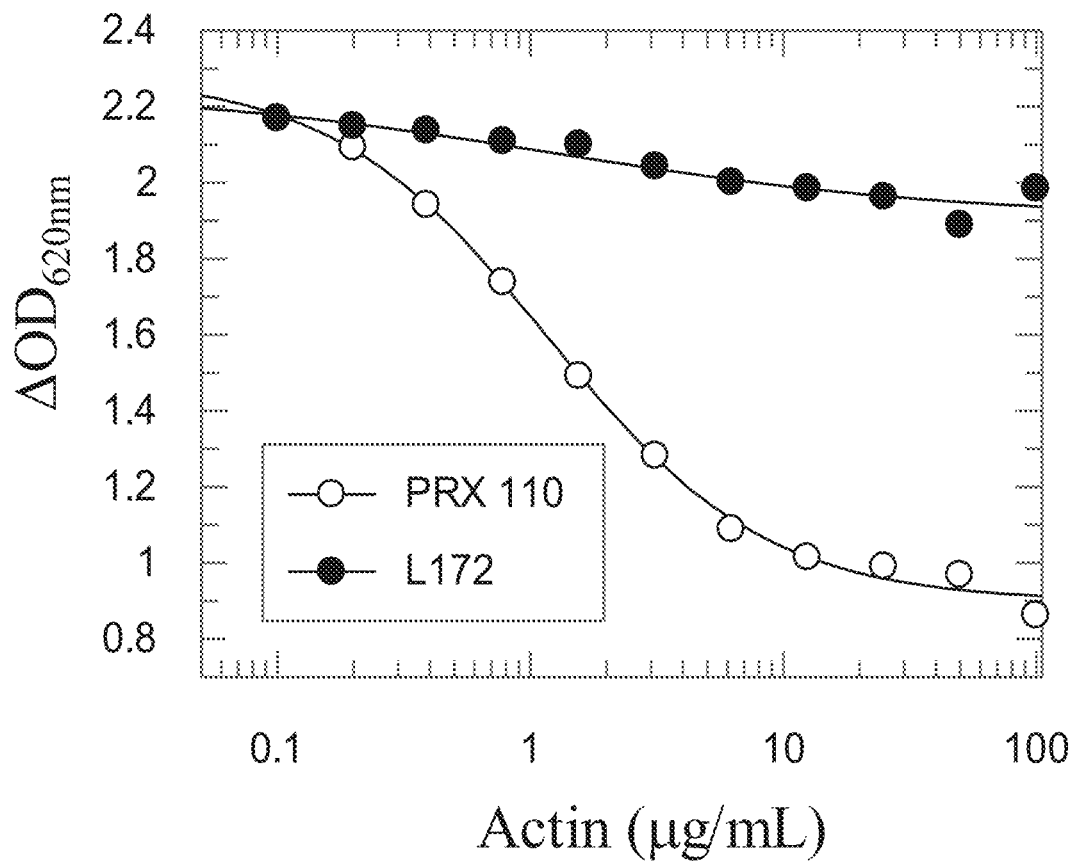
FIG. 5 is a graph showing DNase I activity as a function of actin concentration for DNase I modified by amidation with ethanolamine (L172) and for non-modified DNase I (PRX 110)
Figure 6:
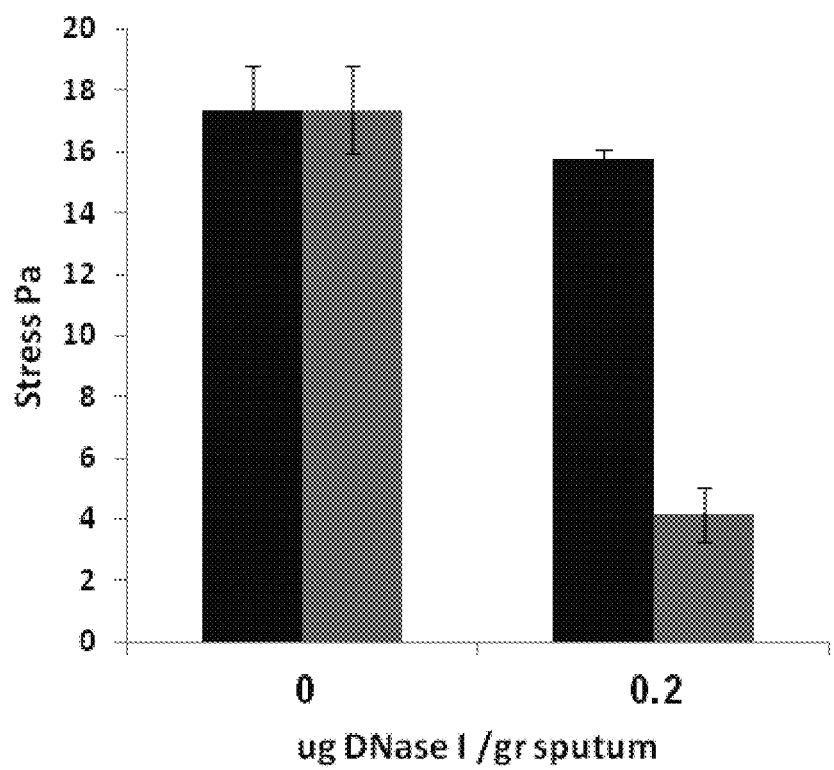
FIG. 6 is a bar graph showing the stress (in Pa units) at which the elastic modulus (G') and viscous modulus (G") cross over (i.e., G'=G", phase angle=45°) in a sputum sample treated with 0 or 0.2 µg per gram sputum of modified DNase I prepared by amidation with ethanolamine according to some embodiments of the invention (L172) or non-modified plant recombinant human DNase I (PRX-110) (each value represents at least measurements)
Figure 7:
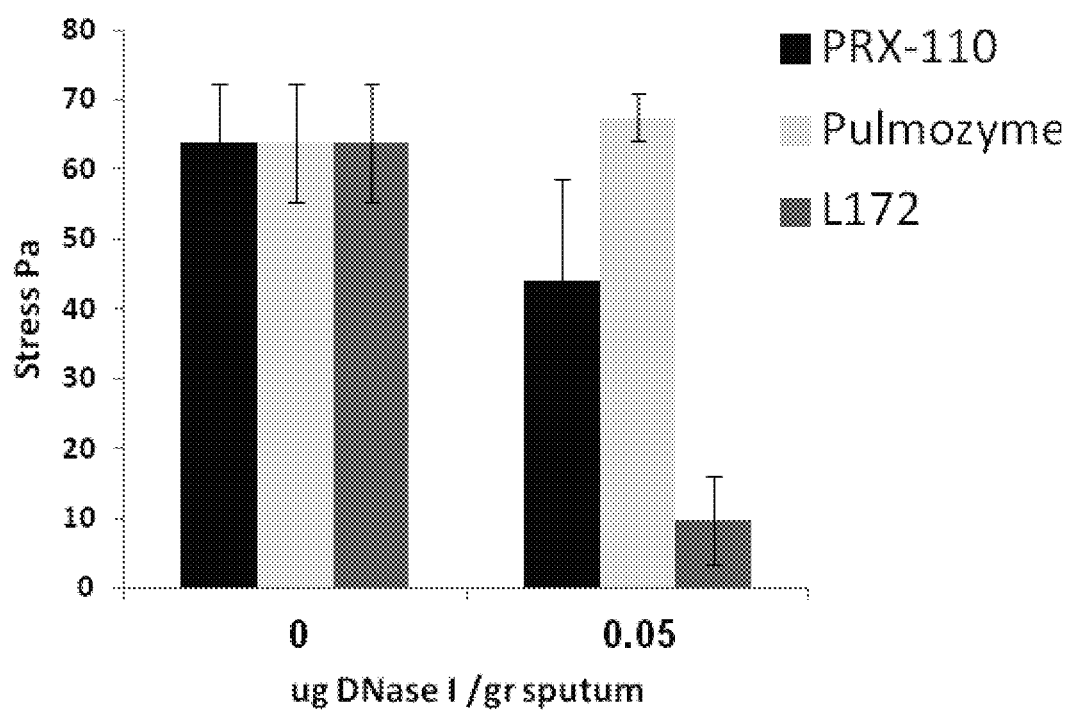
FIG. 7 is a bar graph showing the stress (in Pa units) at which the elastic modulus (G') and viscous modulus (G") cross over (i.e., G'=G", phase angle=45°) in a sputum sample treated with 0 or 0.05 µg per gram sputum of modified DNase I prepared by amidation with ethanolamine according to some embodiments of the invention (L172) or non-modified plant recombinant human DNase I (PRX-110) or Pulmozyme® DNase I (each value represents at least 2 measurements)

FIG. 3 shows DNase I modified by amidation with ethanolamine. FIG. 4 shows that DNase modified by amidation with ethanolamine substantially maintained DNase I enzymatic activity. FIG. 5 shows that DNase modified by amidation with ethanolamine exhibits resistance to inactivation by actin. FIGS. 6 and 7 show that DNase I modified by amidation with ethanolamine is more effective than non-modified DNase I in disrupting on the elastic structure of sputum, an indication of DNA degradation.

Figure 8:
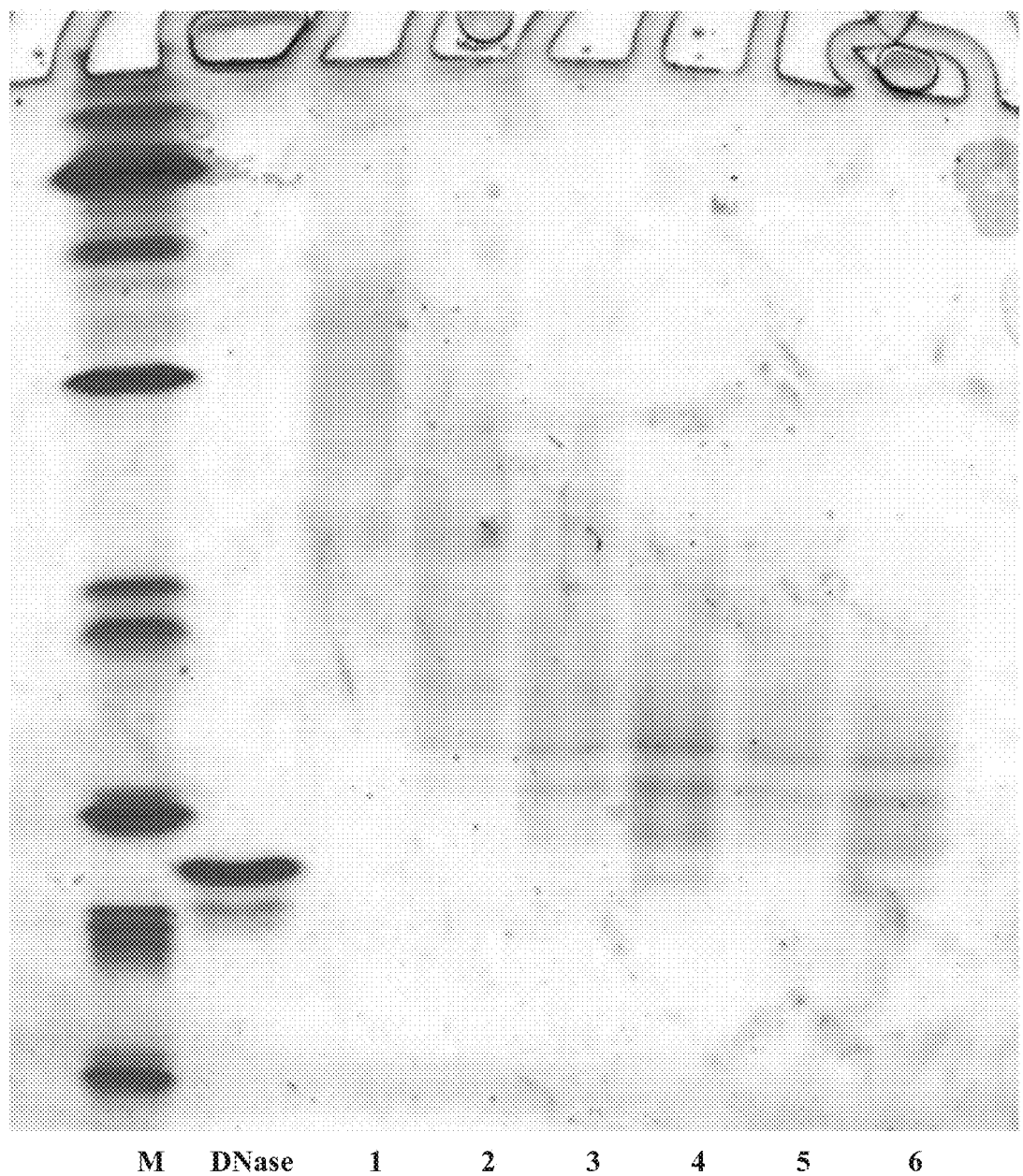
FIG. 8 presents an image of an isoelectric focusing gel (pH 3-10) showing non-modified DNase I (DNase), and DNase I modified using EDC with Tris (lanes 3 and 5), ammonium chloride (lanes 4 and 6) or EDC alone (lanes 1 and 2), with (lanes 5 and 6) or without (lanes 3 and 4) termination of the reaction with Tris or ammonium chloride after 3 hours (pH markers in lane M)

FIGS. 8 and 32 show DNase I from different sources (mammalian recombinant human DNase I and plant recombinant human DNase I) modified by amidation with Tris or ammonium chloride. FIG. 9 shows that DNase modified by amidation with Tris or ammonium chloride substantially maintained DNase I enzymatic activity. FIGS. 10 and 33 show that DNase I modified by amidation with Tris or ammonium chloride exhibits resistance to inactivation by actin. FIG. 11 shows that the kinetics of DNase I modified by amidation with Tris is similar to that of non-modified DNase I. FIGS. 12A, 12B, 14 and 15 show that DNase I modified by amidation with Tris was considerably more effective than non-modified DNase I at hydrolyzing DNA in sputum. FIGS. 13, 16A-16D and 17 show that DNase I modified by amidation with Tris considerably more effective than non-modified DNase I at disrupting the elastic structure of sputum. FIGS. 27-31C show that the resistance to inactivation by actin and ability to disrupt the elastic nature of sputum is correlated to the number of sites in the DNase I which are modified by amidation.

FIGS. 18 and 19 show that CMC (N-cyclohexyl-N'-(2-morpholinoethyl)carbodiimide metho-p-toluenesulfonate) is a more effective coupling agent for effecting amidation than are DIC (diisopropylcarbodiimide) and DTC (di-t-butylcarbodiimide).

FIGS. 35 and 36 show that an exemplary DNase I modification process results in an increase of the protein's molecular weight, thereby confirming amidation of the protein by the amine.

FIG. 47 shows the glycan structures of modified plant recombinant human DNase I.

These results indicate that amidation of one or more carboxylic acids of DNase I protein by reacting it with an amine-containing compound results in an enzymatically active modified DNase I protein which exhibits resistance to inactivation by actin, and that such a result is obtained while forming in the modified DNase I protein amide moieties that exhibit a wide variety of functional groups. Such a result may be obtained by forming amide moieties that exhibit functional groups which are, for example, positively charged (e.g., amide groups as obtained by amidation with a diamine) or non-charged (e.g., amide groups as obtained by amidation with a monoamine); hydrophobic (e.g., amide groups as obtained by amidation with butylamine) or hydrophilic (e.g., amide groups as obtained by amidation with ethanolamine, Tris or a diamine); and have a relatively bulky alkyl group (e.g., amide groups as obtained by amidation with hexamethylene diamine or Tris), a small alkyl group (e.g., amide groups as obtained by amidation with ethanolamine or ethylene diamine) or no alkyl group (e.g., amide groups as obtained by amidation with ammonia).

According to an aspect of some embodiments of the invention, there is provided a modified DNase I protein comprising an amino acid sequence substantially homologous to an amino acid sequence of a DNase I protein (according to any of the respective embodiments described herein), in which at least one amino acid residue (of the amino acid sequence of the modified DNase I) is a non-cellularly modified amino acid residue, as defined herein.

Herein, the phrase "non-cellularly modified amino acid residue" refers to an amino acid residue which is not included or incorporated as part of translation (e.g., which is not one of the 20 standard amino acid residues) and which is not formed in a DNase without human intervention (man-made activity). The phrase "non-cellularly modified" is also referred to herein interchangeably as "chemically modified" or "synthetically modified" or "non-cellularly synthetically modified", and describes a chemical modification (also referred to herein as a "synthetic modification" or "non-cellular modification") introduced synthetically to DNase.

This phrase is also referred to herein interchangeably as "non-cellular post-translationally modified amino acid residue" or simply as "post-translationally modified amino acid residue", and is not to be regarded as similar or equivalent to post-translational modifications that naturally occur in cells. Thus, amino acid residues formed by cellular post-translational modification, for example, glycosylation (including, without limitation, glycosylated asparagine, arginine, serine, threonine, tyrosine, tryptophan and/or C-terminal amino acid residues), phosphorylation (including, without limitation, phosphorylated serine, threonine and/or tyrosine residues), disulfide bond formation (including, without limitation, a cysteine residue linked by a disulfide bond to another cysteine reside), or deamidation of an asparagine residue to form an isoaspartic acid reside (e.g., at position 74 of SEQ ID NO:1 or a corresponding residue in a homologous sequence to SEQ ID NO: 1) are excluded from the scope of the phrase "non-cellularly modified amino acid residue".

The DNase I protein which is used as a substrate for modification (e.g., a basis for modification, a starting point for modification) to provide the modified DNase I protein described herein is referred to herein for clarity and simplicity as a "non-modified DNase I". It is to be understood that the "non-modified DNase I" is not precluded from being modified in some manner, and that the term "non-modified" is merely intended to refer to the lack of the non-cellularly modified amino acid residue (as defined herein and described in any one of the embodiments herein) present in the modified DNase I protein.

Similarly, the modified DNase I protein comprising at least one non-cellularly modified amino acid residue is described herein for the sake of brevity merely as "modified DNase I" and the like. It is to be understood that the modified DNase I according to embodiments of the invention is modified at least in that it comprises at least one non-cellularly modified amino acid residue, as defined herein. Optionally, the modified DNase I includes additional modifications (in addition to comprising at least one non-cellularly modified amino acid residue, as defined herein), for example, cellular post-translational modifications (e.g., as described herein) and/or additional synthetic modifications.

In some embodiments of any of the embodiments described herein, the modified DNase I is characterized by (or exhibits) at least one property selected from the group consisting of:

a) a DNA hydrolytic activity in the presence of 5 μg/ml human non-muscle actin which is at least 50% of a DNA hydrolytic activity of the modified DNase I protein in the absence of human non-muscle actin;

b) a DNA hydrolytic activity in the presence of 50 μg/ml human non-muscle actin which is at least 20% of a DNA hydrolytic activity of the modified DNase I protein in the absence of human non-muscle actin;

c) a DNA hydrolytic activity in the presence of 5 μg/ml human non-muscle actin which is at least 150% of a DNA hydrolytic activity of the non-modified DNase I protein in the presence of 5 μg/ml human non-muscle actin;

d) a DNA hydrolytic activity in the presence of 50 μg/ml human non-muscle actin which is at least 150% of a DNA hydrolytic activity of the non-modified DNase I protein in the presence of 50 μg/ml human non-muscle actin; and e) an $IC_{50}$ with respect to DNA hydrolytic activity in the presence of human non-muscle actin which is at least twice an $IC_{50}$ of a non-modified DNase I protein with respect to DNA hydrolytic activity in the presence of human non-muscle actin.

In some embodiments of any of the embodiments described herein, the modified DNase I is characterized by at least 2 of the above mentioned 5 properties (labeled a) to e)). In some embodiments, the modified DNase I is characterized by at least 3 of the above mentioned 5 properties. In some embodiments, the modified DNase I is characterized by at least 4 of the above mentioned 5 properties. In some embodiments, the modified DNase I is characterized by each of the above mentioned 5 properties.

Herein, the phrase "$IC_{50}$ with respect to DNA hydrolytic activity in the presence of human non-muscle actin" refers to a concentration of human non-muscle actin which inhibits a DNA hydrolytic activity (e.g., of a modified or non-modified DNase I described herein) such that the activity is reduced by precisely 50%.

Herein, the terms "AIR DNase" and "actin inhibition resistant DNase" (which are used interchangeably) refer to any DNase modified in a manner described herein, such that the modified DNase is less susceptible than the corresponding non-modified DNase to inhibition of DNA hydrolytic activity in the presence of actin.

In any of the comparisons between modified and non-modified DNase I described herein, the non-modified DNase I used for comparison preferably differs from the modified DNase I only in the absence of the non-cellularly modified amino acid residue of the modified DNase I. For example, in embodiments, wherein the non-cellularly modified amino acid residue is at a position occupied by an amino acid residue of a homologous naturally occurring DNase I protein (e.g., having SEQ ID NO: 1), the non-modified DNase I used for comparison has the amino acid of the naturally occurring protein at that position; whereas in embodiments wherein the non-cellularly modified amino acid residue is does not have a corresponding amino acid residue of a homologous naturally occurring DNase I protein (e.g., having SEQ ID NO: 1), for example, the non-cellularly modified amino acid residue is inserted between two amino acid residues which are adjacent to one another in the naturally occurring protein, the non-cellularly modified amino acid residue is simply deleted from the non-modified DNase I used for comparison.

To determine DNase I activity for modified or non-modified DNase I according to any of the respective embodiments described herein, the DNase I can be incubated (optionally at 37° C.) for a period of time (optionally 4 hours) with DNA (optionally salmon sperm DNA) complexed with methyl green in an aqueous solution at a pH of about 7.5 (optionally a solution of 25 mM HEPES-NaOH, 4 mM $CaCl_2$, 4 mM $MgCl_2$, 0.1% bovine serum albumin, 0.05% polysorbate 20 (e.g., TWEEN-20), pH 7.5). Absorption of light by methyl green (optionally at a wavelength of 620 nm) is measured before and after incubation with DNase I. Hydrolysis of DNA by DNase I is observed as a reduction in absorption by methyl green upon incubation with DNase I (e.g., as described in the Examples section herein).

In some embodiments of any one of the embodiments described herein, the DNase I activity (e.g., of modified and/or non-modified DNase I) is determined at a DNase I concentration of 45 ng/ml.

To determine DNase I activity for modified or non-modified DNase I in the presence of actin according to any of the respective embodiments described herein, human non-muscle actin (optionally from platelets), at the indicated concentration, and ATP (optionally 0.1 mM) are further incubated with the abovementioned DNase I, DNA and methyl green in the aqueous solution. To determine an $IC_{50}$, measurements of DNase I activity are performed at many actin concentrations (optionally 2-fold serial dilutions), and the results are analyzed using a non-linear fit, according to a suitable algorithm for determining $IC_{50}$ (e.g., as described in the Examples section herein).

In some embodiments of any of the embodiments described herein, the modified DNase I is characterized by a DNA hydrolytic activity in the presence of 1 μg/ml human non-muscle actin which is at least 50% of a DNA hydrolytic activity of the modified DNase I protein in the absence of human non-muscle actin (e.g., as determined at a DNase I concentration of 45 ng/ml). In some embodiments, the activity in the presence of 1 μg/ml human non-muscle actin is at least 70% of the activity in the absence of human non-muscle actin. In some embodiments, the activity in the presence of 1 μg/ml human non-muscle actin is at least 80% of the activity in the absence of human non-muscle actin. In some embodiments, the activity in the presence of 1 μg/ml human non-muscle actin is at least 90% of the activity in the absence of human non-muscle actin. In some embodiments, the activity in the presence of 1 μg/ml human non-muscle actin is at least 95% of the activity in the absence of human non-muscle actin. In some embodiments, the activity in the presence of 1 μg/ml human non-muscle actin is at least 97.5% of the activity in the absence of human non-muscle actin.

In some embodiments of any of the embodiments described herein, the modified DNase I is characterized by a DNA hydrolytic activity in the presence of 5 μg/ml human non-muscle actin which is at least 60% of a DNA hydrolytic activity of the modified DNase I protein in the absence of human non-muscle actin. In some embodiments, the activity in the presence of 5 μg/ml human non-muscle actin is at least 70% of the activity in the absence of human non-muscle actin. In some embodiments, the activity in the presence of 5 μg/ml human non-muscle actin is at least 80% of the activity in the absence of human non-muscle actin. In some embodiments, the activity in the presence of 5 μg/ml human non-muscle actin is at least 90% of the activity in the absence of human non-muscle actin. In some embodiments, the activity in the presence of 5 µg/ml human non-muscle actin is at least 95% of the activity in the absence of human non-muscle actin.

In some embodiments of any of the embodiments described herein, the modified DNase I is characterized by a DNA hydrolytic activity in the presence of 50 µg/ml human non-muscle actin which is at least 30% of a DNA hydrolytic activity of the modified DNase I protein in the absence of human non-muscle actin. In some embodiments, the activity in the presence of 50 µg/ml human non-muscle actin is at least 40% of the activity in the absence of human non-muscle actin. In some embodiments, the activity in the presence of 50 µg/ml human non-muscle actin is at least 50% of the activity in the absence of human non-muscle actin. In some embodiments, the activity in the presence of 50 µg/ml human non-muscle actin is at least 60% of the activity in the absence of human non-muscle actin. In some embodiments, the activity in the presence of 50 µg/ml human non-muscle actin is at least 70% of the activity in the absence of human non-muscle actin. In some embodiments, the activity in the presence of 50 µg/ml human non-muscle actin is at least 80% of the activity in the absence of human non-muscle actin. In some embodiments, the activity in the presence of 50 µg/ml human non-muscle actin is at least 90% of the activity in the absence of human non-muscle actin.

In some embodiments of any of the embodiments described herein, the modified DNase I is characterized by a DNA hydrolytic activity in the presence of 5 µg/ml human non-muscle actin which is at least 200% of (twofold) a DNA hydrolytic activity of the non-modified DNase I protein in the presence of 5 µg/ml human non-muscle actin. In some such embodiments, the activity is at least 300% of (3-fold) the activity of the non-modified DNase I protein. In some embodiments, the activity is at least 500% of (5-fold) the activity of the non-modified DNase I protein. In some embodiments, the activity is at least 1,000% of (10-fold) the activity of the non-modified DNase I protein. In some embodiments, the activity is at least 2,000% of (20-fold) the activity of the non-modified DNase I protein. In some embodiments, the activity is at least 5,000% of (50-fold) the activity of the non-modified DNase I protein. In some embodiments, the activity is at least 10,000% of (100-fold) the activity of the non-modified DNase I protein.

In some embodiments of any of the embodiments described herein, the modified DNase I is characterized by a DNA hydrolytic activity in the presence of 50 µg/ml human non-muscle actin which is at least 200% of (twofold) a DNA hydrolytic activity of the non-modified DNase I protein in the presence of 50 µg/ml human non-muscle actin. In some such embodiments, the activity is at least 300% of (3-fold) the activity of the non-modified DNase I protein. In some embodiments, the activity is at least 500% of (5-fold) the activity of the non-modified DNase I protein. In some embodiments, the activity is at least 1,000% of (10-fold) the activity of the non-modified DNase I protein. In some embodiments, the activity is at least 2,000% of (20-fold) the activity of the non-modified DNase I protein. In some embodiments, the activity is at least 5,000% of (50-fold) the activity of the non-modified DNase I protein. In some embodiments, the activity is at least 10,000% of (100-fold) the activity of the non-modified DNase I protein.

Without being bound by any particular theory, it is believed that the hydrolytic activity of about 45 ng/ml DNase I (as exemplified herein) in the presence of actin concentrations of at least about 0.9 µg/ml, for example, about 1, 5 or 50 µg/ml described herein (e.g., according to any of embodiments described herein relating to DNase activity at such actin concentrations) is particularly relevant to clinical applications according to some embodiments described herein, as the ratio of DNase I concentration (45 ng/ml) to such actin concentration (e.g., 0.9-100 µg/ml) corresponds to a clinically relevant ratio of a concentration of 2.9 µg/ml DNase I (as reported to be present in respiratory mucus 15 minutes after aerosolization of DNase I at a recommended dose [Zahm et al., Eur Respir J 1995, 8:381-386]) to a concentration of 60-5,000 µg/ml actin (as reported to be present in respiratory mucus [Ulmer et al., PNAS 1996, 93:8225-8229; Sanders et al., Thorax 2006, 61:962-966]).

In some embodiments of any of the embodiments described herein, the modified DNase I is characterized by an $IC_{50}$ with respect to DNA hydrolytic activity in the presence of human non-muscle actin which is at least 300% of (3-fold) an $IC_{50}$ of a non-modified DNase I protein with respect to DNA hydrolytic activity in the presence of human non-muscle actin. In some embodiments, the $IC_{50}$ is at least 500% of (5-fold) an $IC_{50}$ of the non-modified DNase I protein. In some embodiments, the $IC_{50}$ is at least 1,000% of (10-fold) an $IC_{50}$ of the non-modified DNase I protein. In some embodiments, the $IC_{50}$ is at least 2,000% of (20-fold) an $IC_{50}$ of the non-modified DNase I protein. In some embodiments, the $IC_{50}$ is at least 5,000% of (50-fold) an $IC_{50}$ of the non-modified DNase I protein. In some embodiments, the $IC_{50}$ is at least 10,000% of (100-fold) an $IC_{50}$ of the non-modified DNase I protein.

In some embodiments of any of the embodiments described herein, the modified DNase I is characterized by an $IC_{50}$ with respect to DNA hydrolytic activity in the presence of human non-muscle actin which is at least 2 µg/ml (of actin). In some embodiments, the $IC_{50}$ is at least 5 µg/ml. In some embodiments, the $IC_{50}$ is at least 10 µg/ml. In some embodiments, the $IC_{50}$ is at least 20 µg/ml. In some embodiments, the $IC_{50}$ is at least 50 µg/ml. In some embodiments, the $IC_{50}$ is at least 100 µg/ml. In some embodiments, the $IC_{50}$ is determined at a DNase I concentration of 45 ng/ml.

In some embodiments of any of the embodiments described herein, the modified DNase I is characterized by enhanced enzymatic activity even in the absence of actin. In some such embodiments, enhanced enzymatic activity is characterized (at least in part) by a reduced Michaelis constant with respect to DNA hydrolytic activity, in comparison with a non-modified DNase I. The skilled artisan will appreciate that a reduced Michaelis constant ($K_M$) will be associated with enhanced affinity to a substrate and enhanced activity at low concentrations of substrate.

Enzymatic activity parameters such as Michaelis constant ($K_M$), specific activity ($k_{cat}$), catalytic efficiency ($k_{cat}/K_M$) and maximum velocity ($V_{max}$) can be determined by measuring a rate of DNA hydrolysis by DNase (according to any of the embodiments described herein) and fitting the obtained data to an equation such as the Michaelis—Menten equation using techniques known in the art. Exemplary conditions for any of the enzymatic activity parameters described herein include incubation in an aqueous buffer of 25 mM HEPES (4-(2-hydroxyethyl)-1-piperazineethanesulfonic acid) at pH 7.5, with 4 mM $CaCl_2$, 4 mM $MgCl_2$, 0.1% bovine serum albumin, and 0.05% polysorbate 20 (e.g., TWEEN-20)), wherein the DNA is salmon sperm DNA.

Preferably, activity is measured at a range of DNA (e.g., salmon sperm DNA) concentrations which includes at least one concentration which is at least about 5-fold of the calculated $K_M$ (e.g., additional measurement with at least one higher DNA concentration is performed if an initially calculated $K_M$ is more than 20% of the highest tested DNA concentration, and $K_M$ is then recalculated), and at least one concentration which is about equal to the $K_M$ or lower (e.g., additional measurement with at least one lower DNA concentration is performed if an initially calculated $K_M$ is lower than about the lowest tested DNA concentration, and $K_M$ is then recalculated).

Optionally, rates of DNA hydrolysis are measured using a DNase I concentration in a range of from 2.5 to 14 ng/ml (optionally 2.5 ng/ml) and/or salmon sperm DNA at a concentration in a range of about 1.6 to at least about 5-fold of a $K_M$ of the tested DNase, as described hereinabove (e.g., as exemplified herein).

In some embodiments of any of the embodiments described herein, the modified DNase I is characterized by a Michaelis constant with respect to DNA hydrolytic activity which is no more than 90% of a Michaelis constant of a non-modified DNase I (e.g., under the same conditions). In some embodiments, the Michaelis constant of the modified DNase I is no more than 80% of a Michaelis constant of the non-modified DNase I. In some embodiments, the Michaelis constant of the modified DNase I is no more than 70% of a Michaelis constant of the non-modified DNase I. In some embodiments, the Michaelis constant of the modified DNase I is no more than 60% of a Michaelis constant of the non-modified DNase I. In some embodiments, the Michaelis constant of the modified DNase I is no more than 50% of a Michaelis constant of the non-modified DNase I. In some embodiments, the Michaelis constant of the modified DNase I is no more than 40% of a Michaelis constant of the non-modified DNase I. In some embodiments, the Michaelis constant of the modified DNase I is no more than 30% of a Michaelis constant of the non-modified DNase I. In some embodiments, the Michaelis constant of the modified DNase I is no more than 20% of a Michaelis constant of the non-modified DNase I. In some embodiments, the Michaelis constant of the modified DNase I is no more than 10% of a Michaelis constant of the non-modified DNase I. In some embodiments, the Michaelis constant is determined at a DNase I concentration of 2.5 ng/ml, and the DNA is salmon sperm DNA.

In some embodiments of any of the embodiments described herein, the modified DNase I is characterized by a Michaelis constant with respect to DNA hydrolytic activity which is no more than 40 µg/ml DNA. In some embodiments, the Michaelis constant of the modified DNase I is no more than 30 µg/ml DNA. In some embodiments, the Michaelis constant of the modified DNase I is no more than 20 µg/ml DNA. In some embodiments, the Michaelis constant of the modified DNase I is no more than 15 µg/ml DNA. In some embodiments, the Michaelis constant of the modified DNase I is no more than 10 µg/ml DNA. In some embodiments, the Michaelis constant of the modified DNase I is no more than 5 µg/ml DNA. In some embodiments, the Michaelis constant of the modified DNase I is no more than 2.5 µg/ml DNA. In some embodiments, the Michaelis constant is determined at a DNase I concentration of 2.5 ng/ml, and the DNA is salmon sperm DNA.

In some embodiments of any of the embodiments described herein, the modified DNase I is characterized by a specific activity which is at least 70% of a specific activity of a non-modified DNase I (e.g., under the same conditions). In some embodiments, the modified DNase I is characterized by a specific activity which is at least 80% of a specific activity of a non-modified DNase I. In some embodiments, the modified DNase I is characterized by a specific activity which is at least 90% of a specific activity of a non-modified DNase I. In some embodiments, the modified DNase I is characterized by a specific activity which is at least 100% of a specific activity of a non-modified DNase I. In some embodiments, the modified DNase I is further characterized by a reduced Michaelis constant in comparison with the non-modified DNase. In some embodiments, the specific activity is determined at a DNase I concentration of 2.5 ng/ml, and the DNA is salmon sperm DNA.

In some embodiments of any of the embodiments described herein, the modified DNase I is characterized by a catalytic efficiency ($k_{cat}/K_M$) which is greater than a catalytic efficiency of a non-modified DNase I (e.g., under the same conditions). In some embodiments, the modified DNase I is characterized by a catalytic efficiency which is at least 150% of (i.e., 50% greater than) a catalytic efficiency of a non-modified DNase I. In some embodiments, the modified DNase I is characterized by a catalytic efficiency which is at least 200% (two-fold) of a catalytic efficiency of a non-modified DNase I. In some embodiments, the modified DNase I is characterized by a catalytic efficiency which is at least 300% (3-fold) of a catalytic efficiency of a non-modified DNase I. In some embodiments, the modified DNase I is characterized by a catalytic efficiency which is at least 400% (4-fold) of a catalytic efficiency of a non-modified DNase I. In some embodiments, the modified DNase I is characterized by a catalytic efficiency which is at least 500% (5-fold) of a catalytic efficiency of a non-modified DNase I. In some embodiments, the modified DNase I is characterized by a catalytic efficiency which is at least 600% (6-fold) of a catalytic efficiency of a non-modified DNase I. In some embodiments, the modified DNase I is characterized by a catalytic efficiency which is at least 800% (8-fold) of a catalytic efficiency of a non-modified DNase I. In some embodiments, the modified DNase I is characterized by a catalytic efficiency which is at least 1000% (10-fold) of a catalytic efficiency of a non-modified DNase I. In some embodiments, the catalytic efficiency is determined (e.g., by determining the specific activity and Michaelis constant) at a DNase I concentration of 2.5 ng/ml, and the DNA is salmon sperm DNA.

Without being bound by any particular theory, it is believed that modified DNase I according to some embodiments of the invention combines enhanced activity in a form of a surprisingly low Michaelis constant and increased catalytic efficiency, associated with enhanced activity at low concentrations of DNA (the substrate of DNase I) in combination with a specific activity which is similar to that of non-modified DNase I, which indicates that DNase activity is not substantially decreased at high DNA concentrations.

In some embodiments of any of the embodiments described herein, the modified DNase I comprises at least 2 non-cellularly modified amino acid residues. In some embodiments, the modified DNase I comprises at least 3 non-cellularly modified amino acid residues. In some embodiments, the modified DNase I comprises at least 4 non-cellularly modified amino acid residues. In some embodiments, the modified DNase I comprises at least 5 non-cellularly modified amino acid residues. In some embodiments, the modified DNase I comprises at least 7 non-cellularly modified amino acid residues. In some embodiments, the modified DNase I comprises at least 10 non-cellularly modified amino acid residues. In some embodiments, the modified DNase I comprises at least 15 non-cellularly modified amino acid residues. In some embodiments, the modified DNase I comprises at least 20 non-cellularly modified amino acid residues. In some embodiments, the modified DNase I comprises at least 30 non-cellularly modified amino acid residues.

In some embodiments of any of the embodiments described herein, the modified DNase I is a mixture of species, wherein the different species may optionally have a non-cellularly modified amino acid residues at different sites in the protein, a different number of non-cellularly modified amino acid residues, and/or different species and/or combination of species of non-cellularly modified amino acid residues (e.g., different amide group species, according to any of the respective embodiments described herein). The mixture of species may optionally be further intermixed with non-modified DNase I, although such non-modified DNase I is not considered a part of the modified DNase I.

In some embodiments wherein the modified DNase I is a mixture of modified DNase I species, a number of non-cellularly modified amino acid residues according to any of the respective embodiments described herein refers to an average number of non-cellularly modified amino acid residues, as averaged over the molecules of modified DNase I.

In some embodiments of any of the embodiments described herein, at least one carboxylic acid group of the DNase I protein is replaced by an amide group. In such embodiments, a carboxylic acid group according to any one of the embodiments described herein relating to a carboxylic acid group (e.g., in the respective section herein) may optionally be replaced with an amide group according to any one of the embodiments described herein relating to an amide acid group (e.g., in the respective section herein).

The replacement of the at least one carboxylic acid group by an amide group optionally represents at least a portion of the non-cellular modification in the modified DNase I. In some embodiments of any of the embodiments described herein, each of the non-cellularly modified amino acid residues of the modified DNase I is an amino acid residue in which at least one carboxylic acid group is replaced by an amide group.

According to some of any of the embodiments of the present invention, the modified DNase I protein is such that less than 10 weight percent of the modified DNase I is in a dimeric or multimeric form.

Herein, the term "multimeric" refers to a plurality of molecules (e.g., DNase I proteins) which interact so as to be covalently and/or non-covalently bound to one another, and encompasses both ordered structures and/or in an unordered structures (e.g., aggregates). The plurality of molecules may optionally be the same or different. Examples include, without limitation, protein dimers (2 proteins interacting), trimers (3 proteins interacting), tetramers (4 proteins interacting) and multimers of higher molecular weight, or any other structures that result from intermolecular interactions.

Amide Group:

As used herein, the term "amide" refers to a —C(=O)—NR'R" group, wherein R' and R" are each selected from the group consisting of hydrogen and a saturated or unsaturated hydrocarbon moiety, the hydrocarbon moiety being substituted or non-substituted. R' and R" are bound (to the nitrogen atom of the amide) via a carbon atom thereof (unless R' or R" is hydrogen). When substituted, the carbon atom of R' and/or R" which is bound to the nitrogen atom of the amide is not substituted by oxo, such that R' and R" are not (for example) carbonyl, C-carboxy or amide, as these groups are defined herein. Optionally, R' and R" are selected from the group consisting of hydrogen and alkyl.

The term "hydrocarbon" describes an organic moiety that includes, as its basic skeleton, a chain of carbon atoms, substituted mainly by hydrogen atoms. The hydrocarbon can be saturated or non-saturated, be comprised of aliphatic, alicyclic or aromatic moieties, and can optionally be substituted by one or more substituents (other than hydrogen). The hydrocarbon moiety is optionally interrupted by one or more heteroatoms, including, without limitation, one or more oxygen, nitrogen and/or sulfur atoms.

In some embodiments of any of the embodiments described herein, R' and R" are selected from the group consisting of alkyl (e.g., wherein the hydrocarbon moiety is saturated), alkenyl (e.g., wherein the hydrocarbon moiety is unsaturated), alkynyl (e.g., wherein the hydrocarbon moiety is unsaturated), cycloalkyl, heteroalicyclic (bonded through a ring carbon), aryl and heteroaryl (bonded through a ring carbon), as these groups are defined herein.

In some embodiments of any of the embodiments described herein, the hydrocarbon is a substituted or non-substituted saturated hydrocarbon selected from the group consisting of substituted or non-substituted alkyl, cycloalkyl and heteroalicyclic (as defined herein).

In some embodiments of any of the embodiments described herein, the C(=O) in an amide group, as defined hereinabove, is derived from a carboxylic acid group present in the non-modified DNase I (as described herein according to any of the respective embodiments), whereas the NR'R" in the amide group represents a substituent which replaces the —OH of the carboxylic acid group.

In some embodiments of any of the embodiments described herein, the carbon atom of R' and/or R" which is bound to the nitrogen atom of the amide is not bound to any other heteroatom (i.e., is bound only to carbon and/or hydrogen atoms).

In some embodiments of any of the embodiments described herein, R" is hydrogen.

In some embodiments of any of the embodiments described herein, R' and R" are each hydrogen.

In some embodiments of any of the embodiments described herein, at last one of R' and R" is not hydrogen.

In some embodiments of any of the embodiments described herein, at least one of R' and R" is a hydrocarbon moiety, that is the amide group is not a —C(=O)NH$_2$ group. In some such embodiments, R' is a hydrocarbon moiety and R" is hydrogen.

In some embodiments of any of the embodiments described herein, an amide group which replaces a carboxylic acid group at a side chain of an amino acid residue such as, for example, a glutamic acid or aspartic acid residue, is not a —C(=O)NH$_2$ group, whereas, for example, a C-terminal carboxylic acid may optionally be replaced with a C-terminal —C(=O)NH$_2$ group.

In some embodiments of any of the embodiments described herein, the amide group has the general formula:

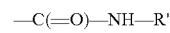

wherein R' is selected from the group consisting of alkyl, alkenyl and alkynyl, each being non-substituted or substituted with one or more substituents selected from the group consisting of hydroxy and amino.

Herein, the terms "hydroxy" and "hydroxyl" refer to —OH.

Herein, the terms "amine" and "amino" each refer to either a —NR'R" group or a —N$^+$R'R"R'" group, wherein R' and R" are as defined herein, and R'" is defined as R' and R" are defined herein. Optionally, R', R" and R'" are selected from the group consisting of hydrogen and alkyl comprising 1 to 4 carbon atoms. Optionally, R' and R" are hydrogen.

In some embodiments of any of the embodiments described herein, R' is a non-substituted alkyl, alkenyl or alkynyl. In some embodiments, R' is a non-substituted alkyl, for example, methyl, ethyl, n-propyl, isopropyl, n-butyl, isobutyl and/or t-butyl.

In some embodiments of any of the embodiments described herein, R' is substituted by (optionally only by) one or more substituents which are hydroxy. In some embodiments, R' comprises only one hydroxy group (e.g., wherein R' is 2-hydroxyethyl). In some embodiments, R' comprises at least 2 hydroxy groups. In some embodiments, R' comprises at least 3 hydroxy groups. In some embodiments, R' comprises from 2 to 6 hydroxy groups. In some embodiments, R' comprises from 2 to 4 hydroxy groups. In some embodiments, R' comprises 3 hydroxy groups. Tris (hydroxymethyl)methyl is a non-limiting example of an R' group comprising 3 hydroxy groups. In some embodiments, R' is a substituted alkyl.

In some embodiments of any of the embodiments described herein, R' is substituted by (optionally only by) one or more substituents which are amino. In some embodiments, R' comprises from 1 to 4 amino substituents. In some embodiments, R' comprises one amino substituent. In some embodiments, R' is a substituted alkyl.

In some embodiments of any of the embodiments described herein, R' is substituted by one or more substituents which are —$NH_2$. In some embodiments, R' is a substituted alkyl, for example, 2-aminoethyl, 3-aminopropyl, 4-aminobutyl, 5-aminopentyl and/or 6-aminohexyl.

In some embodiments of any of the embodiments described herein, R' is a hydrocarbon moiety substituted by one or more substituents which are alkylamino, for example, a primary alkylamino having the formula —NHR', wherein R' is alkyl. In some embodiments, the alkyl in the alkylamino is substituted by amino, such that the hydrocarbon moiety is substituted by an (aminoalkyl)amino substituent. In some embodiments, the hydrocarbon moiety is a substituted alkyl, for example, alkyl substituted by (aminoalkyl)amino (e.g., 4-(3-aminopropyl)amino-butyl or 3-(4-aminobutyl)amino-propyl, each of which provides an amide which is a derivative of spermidine).

In some embodiments of any of the embodiments described wherein R' is substituted by one or more amino substituents, the modified DNase I exhibits a reduced Michaelis constant, an increased catalytic efficiency, and/or a specific activity according to any of the respective embodiments herein describing a reduced Michaelis constant, an increased catalytic efficiency and/or a specific activity. In some such embodiments, R' is 2-aminoethyl.

Without being bound by any particular theory, it is believed that a positive charge of an amino substituent enhances affinity to negatively charged DNA, thereby reducing the Michaelis constant.

In some embodiments of any of the embodiments described herein, the hydrocarbon moiety (e.g., R') comprises from 1 to 100 carbon atoms. In some embodiments, the hydrocarbon moiety comprises from 1 to 50 carbon atoms. In some embodiments, the hydrocarbon moiety comprises from 1 to 20 carbon atoms. In some embodiments, the hydrocarbon moiety comprises from 1 to 10 carbon atoms. In some embodiments, the hydrocarbon moiety comprises from 1 to 6 carbon atoms. In some embodiments, the hydrocarbon moiety comprises from 1 to 4 carbon atoms. In some embodiments, the hydrocarbon moiety comprises from 2 to 4 carbon atoms.

In some embodiments of any of the embodiments described herein, the hydrocarbon moiety (e.g., R') comprises from 2 to 10 carbon atoms. In some embodiments, the hydrocarbon moiety comprises from 2 to 6 carbon atoms. In some embodiments, the hydrocarbon moiety comprises from 3 to 5 carbon atoms. In some embodiments, the hydrocarbon moiety comprises 4 carbon atoms.

In some embodiments of any of the embodiments described herein, the hydrocarbon moiety (e.g., R') comprises more than 100 carbon atoms. In some such embodiments, the hydrocarbon moiety is a polymeric moiety, for example, a polyalkylene glycol moiety (optionally modified by a functional group which binds to the nitrogen atom of the amide group). Polyethylene glycol is a non-limiting example of a polyalkylene glycol moiety.

As used herein throughout, the term "alkyl" refers to a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or non-substituted. When substituted, the substituent group can be, for example, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

A "cycloalkyl" group refers to a saturated on unsaturated all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or non-substituted. When substituted, the substituent group can be, for example, alkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein. When a cycloalkyl group is unsaturated, it may comprise at least one carbon-carbon double bond and/or at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or non-substituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazole, pyridine, pyrimidine, quinoline, isoquinoline and purine. The heteroaryl group may be substituted or non-substituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or non-substituted. When substituted, the substituted group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein. Representative examples are piperidine, piperazine, tetrahydrofuran, tetrahydropyran, morpholine and the like.

An "azide" group refers to a $-N=N^{30}=N^-$ group.

An "alkoxy" group refers to both an —O-alkyl and an —O-cycloalkyl group, as defined herein.

An "aryloxy" group refers to both an —O-aryl and an —O-heteroaryl group, as defined herein.

A "thiohydroxy" or "thiol" group refers to a —SH group.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "carbonyl" group refers to a —C(=O)—R' group, where R' is defined as hereinabove.

A "thiocarbonyl" group refers to a —C(=S)—R' group, where R' is as defined herein.

A "carboxyl" or "carboxylate" refers to both "C-carboxy" and O-carboxy".

A "C-carboxy" group refers to a —C(=O)—O—R' groups, where R' is as defined herein.

An "O-carboxy" group refers to an R'C(=O)—O— group, where R' is as defined herein.

A "carboxylic acid" refers to a —C(=O)OH group, including the deprotonated ionic form and salts thereof.

An "oxo" group refers to a =O group.

A "thiocarboxy" or "thiocarboxylate" group refers to both —C(=S)—O—R' and —O—C(=S)R' groups.

A "halo" group refers to fluorine, chlorine, bromine or iodine.

A "sulfinyl" group refers to an —S(=O)—R' group, where R' is as defined herein.

A "sulfonyl" group refers to an —S(=O)$_2$—R' group, where R' is as defined herein.

A "sulfonate" group refers to an —S(=O)$_2$—O—R' group, where R' is as defined herein.

A "sulfate" group refers to an —O—S(=O)$_2$—O—R' group, where R' is as defined as herein.

A "sulfonamide" or "sulfonamido" group encompasses both S-sulfonamido and N-sulfonamido groups, as defined herein.

An "S-sulfonamido" group refers to a —S(=O)$_2$—NR'R" group, with each of R' and R" as defined herein.

An "N-sulfonamido" group refers to an R'S(=O)$_2$—NR" group, where each of R' and R" is as defined herein.

An "O-carbamyl" group refers to an —OC(=O)—NR'R" group, where each of R' and R" is as defined herein.

An "N-carbamyl" group refers to an R'OC(=O)—NR"— group, where each of R' and R" is as defined herein.

A "carbamyl" or "carbamate" group encompasses O-carbamyl and N-carbamyl groups.

An "O-thiocarbamyl" group refers to an —OC(=S)—NR'R" group, where each of R' and R" is as defined herein.

An "N-thiocarbamyl" group refers to an R'OC(=S)NR"— group, where each of R' and R" is as defined herein.

A "thiocarbamyl" or "thiocarbamate" group encompasses O-thiocarbamyl and N-thiocarbamyl groups.

A "C-amido" group refers to a —C(=O)—NR'R" group, where each of R' and R" is as defined herein.

An "N-amido" group refers to an R'C(=O)—NR"— group, where each of R' and R" is as defined herein.

A "urea" group refers to an —N(R')—C(=O)—NR"R'" group, where each of R', R" and R'" is as defined herein.

A "nitro" group refers to an —NO$_2$ group.

A "cyano" group refers to a —C≡N group.

The term "phosphonyl" or "phosphonate" describes a —P(=O)(OR')(OR") group, with R' and R" as defined hereinabove.

The term "phosphate" describes an —O—P(=O)(OR')(OR") group, with each of R' and R" as defined hereinabove.

The term "phosphinyl" describes a —PR'R" group, with each of R' and R" as defined hereinabove.

The term "thiourea" describes a —N(R')—C(=S)—NR"R'" group, where each of R', R" and R'" is as defined herein.

Carboxylic Acid Group:

In some embodiments of any of the embodiments described herein, the carboxylic acid group replaced by an amide group is selected from the group consisting of a carboxylic acid group within a side chain of an amino acid residue and a C-terminal carboxylic acid group.

Examples of side chains of an amino acid residue which comprise a carboxylic acid residue which may optionally be replaced by an amide group according to some embodiments of the invention include, without limitation, a glutamic acid residue, an aspartic acid residue, an N-methyl-glutamic acid residue, an N-methylaspartic acid residue, an α-methylglutamic acid residue, an α-methylaspartic acid residue, a γ-carboxyglutamic acid residue, an N-(carboxymethyl)glycine residue, an N-(2-carboxyethyl)glycine residue and an α-aminoadipic acid residue. In some embodiments, the side chains are glutamic acid and/or aspartic acid side chains.

The amino acid residues may optionally be L-amino acid and/or D-amino acid residues. In some embodiments, the amino acid residues are L-amino acid residues.

In some embodiments, the amino acid residues are L-glutamic acid and/or L-aspartic acid residues.

In some embodiments of any of the embodiments described herein, at least two carboxylic acid groups are replaced by an amide group as described herein. In some embodiments, from 2 to 35 carboxylic acid groups are replaced by an amide group as described herein. In some embodiments, from 2 to 30 carboxylic acid groups are replaced by an amide group as described herein. In some embodiments, from 2 to 25 carboxylic acid groups are replaced by an amide group as described herein. In some embodiments, from 2 to 20 carboxylic acid groups are replaced by an amide group as described herein. In some embodiments, from 2 to 15 carboxylic acid groups are replaced by an amide group as described herein. In some embodiments, from 2 to 10 carboxylic acid groups are replaced by an amide group as described herein. In some embodiments, from 2 to 5 carboxylic acid groups are replaced by an amide group as described herein.

In some embodiments, wherein the modified DNase I is a mixture of modified DNase I species, a number of carboxylic acid groups being replaced by an amide group according to any of the respective embodiments described herein refers to an average number of carboxylic acid groups being replaced, as averaged over the molecules of modified DNase I (i.e., DNase I molecules in which at least one carboxylic acid is replaced by an amide group).

In some embodiments of any of the embodiments described herein, at least 3 carboxylic acid groups are replaced by an amide group as described herein. In some embodiments, from 3 to 35 carboxylic acid groups are replaced by an amide group as described herein. In some embodiments, from 3 to 30 carboxylic acid groups are replaced by an amide group as described herein. In some embodiments, from 3 to 25 carboxylic acid groups are replaced by an amide group as described herein. In some embodiments, from 3 to 20 carboxylic acid groups are replaced by an amide group as described herein. In some embodiments, from 3 to 15 carboxylic acid groups are replaced by an amide group as described herein. In some embodiments, from 3 to 10 carboxylic acid groups are replaced by an amide group as described herein. In some embodiments, from 3 to 5 carboxylic acid groups are replaced by an amide group as described herein.

In some embodiments of any of the embodiments described herein, at least 4 carboxylic acid groups are replaced by an amide group as described herein. In some embodiments, from 4 to 35 carboxylic acid groups are replaced by an amide group as described herein. In some embodiments, from 4 to 30 carboxylic acid groups are replaced by an amide group as described herein. In some embodiments, from 4 to 25 carboxylic acid groups are replaced by an amide group as described herein. In some embodiments, from 4 to 20 carboxylic acid groups are replaced by an amide group as described herein. In some embodiments, from 4 to 15 carboxylic acid groups are replaced by an amide group as described herein. In some embodiments, from 4 to 10 carboxylic acid groups are replaced by an amide group as described herein. In some embodiments, from 4 to 5 carboxylic acid groups are replaced by an amide group as described herein.

In some embodiments of any of the embodiments described herein, at least 5 carboxylic acid groups are replaced by an amide group as described herein. In some embodiments, from 5 to 35 carboxylic acid groups are replaced by an amide group as described herein. In some embodiments, from 5 to 30 carboxylic acid groups are replaced by an amide group as described herein. In some embodiments, from 5 to 25 carboxylic acid groups are replaced by an amide group as described herein. In some embodiments, from 5 to 20 carboxylic acid groups are replaced by an amide group as described herein. In some embodiments, from 5 to 15 carboxylic acid groups are replaced by an amide group as described herein. In some embodiments, from 5 to 10 carboxylic acid groups are replaced by an amide group as described herein.

In some embodiments of any of the embodiments described herein, at least 6 carboxylic acid groups are replaced by an amide group as described herein. In some embodiments, from 6 to 35 carboxylic acid groups are replaced by an amide group as described herein. In some embodiments, from 6 to 30 carboxylic acid groups are replaced by an amide group as described herein. In some embodiments, from 6 to 25 carboxylic acid groups are replaced by an amide group as described herein. In some embodiments, from 6 to 20 carboxylic acid groups are replaced by an amide group as described herein. In some embodiments, from 6 to 15 carboxylic acid groups are replaced by an amide group as described herein. In some embodiments, from 6 to 10 carboxylic acid groups are replaced by an amide group as described herein.

In some embodiments of any of the embodiments described herein, at least 8 carboxylic acid groups are replaced by an amide group as described herein. In some embodiments, from 8 to 35 carboxylic acid groups are replaced by an amide group as described herein. In some embodiments, from 8 to 30 carboxylic acid groups are replaced by an amide group as described herein. In some embodiments, from 8 to 25 carboxylic acid groups are replaced by an amide group as described herein. In some embodiments, from 8 to 20 carboxylic acid groups are replaced by an amide group as described herein. In some embodiments, from 8 to 15 carboxylic acid groups are replaced by an amide group as described herein. In some embodiments, from 8 to 10 carboxylic acid groups are replaced by an amide group as described herein.

In some embodiments of any of the embodiments described herein, at least 10 carboxylic acid groups are replaced by an amide group as described herein. In some embodiments, from 10 to 35 carboxylic acid groups are replaced by an amide group as described herein. In some embodiments, from 10 to 30 carboxylic acid groups are replaced by an amide group as described herein. In some embodiments, from 10 to 25 carboxylic acid groups are replaced by an amide group as described herein. In some embodiments, from 10 to 20 carboxylic acid groups are replaced by an amide group as described herein. In some embodiments, from 10 to 15 carboxylic acid groups are replaced by an amide group as described herein.

In some embodiments of any of the embodiments described herein, at least 12 carboxylic acid groups are replaced by an amide group as described herein. In some embodiments, from 12 to 35 carboxylic acid groups are replaced by an amide group as described herein. In some embodiments, from 12 to 30 carboxylic acid groups are replaced by an amide group as described herein. In some embodiments, from 12 to 25 carboxylic acid groups are replaced by an amide group as described herein. In some embodiments, from 12 to 20 carboxylic acid groups are replaced by an amide group as described herein. In some embodiments, from 12 to 15 carboxylic acid groups are replaced by an amide group as described herein.

In some embodiments of any of the embodiments described herein, at least 15 carboxylic acid groups are replaced by an amide group as described herein. In some embodiments, from 15 to 35 carboxylic acid groups are replaced by an amide group as described herein. In some embodiments, from 15 to 30 carboxylic acid groups are replaced by an amide group as described herein. In some embodiments, from 15 to 25 carboxylic acid groups are replaced by an amide group as described herein. In some embodiments, from 15 to 20 carboxylic acid groups are replaced by an amide group as described herein.

In some embodiments of any of the embodiments described herein, at least 20 carboxylic acid groups are replaced by an amide group as described herein. In some embodiments, from 20 to 35 carboxylic acid groups are replaced by an amide group as described herein. In some embodiments, from 20 to 30 carboxylic acid groups are replaced by an amide group as described herein. In some embodiments, from 20 to 25 carboxylic acid groups are replaced by an amide group as described herein.

In some embodiments of any of the embodiments described herein, at least 25 carboxylic acid groups are replaced by an amide group as described herein. In some embodiments, from 25 to 35 carboxylic acid groups are replaced by an amide group as described herein. In some embodiments, from 25 to 30 carboxylic acid groups are replaced by an amide group as described herein.

In some embodiments of any of the embodiments described herein, at least 30 carboxylic acid groups are replaced by an amide group as described herein. In some embodiments, from 30 to 35 carboxylic acid groups are replaced by an amide group as described herein.

Non-limiting representative examples of glutamic acid residue side chains and aspartic acid residue side chains which may optionally be replaced by an amide group according to any of the respective embodiments described herein include, without limitation, Glu13, Glu39, Glu69, Glu78, Glu102, Glu112, Glu124, Glu127, Glu143, Glu156, Glu161, Glu256, Asp33, Asp42, Asp53, Asp58, Asp61, Asp87, Asp93, Asp98, Asp99, Asp107, Asp139, Asp145, Asp149, Asp153, Asp162, Asp168, Asp198, Asp201, Asp212, Asp228, Asp243 and Asp251 in SEQ ID NO: 1, and any corresponding glutamic acid or aspartic acid residues in an amino acid sequence homologous to SEQ ID NO: 1. For example, SEQ ID NO: 2 contains glutamic acid and aspartic acid residues corresponding residues to each of the aforementioned glutamic acid or aspartic acid residues, each residue being numbered by one number higher than the corresponding residue in SEQ ID NO: 1.

In some embodiments of any of the embodiments described herein, at least Glu13 in SEQ ID NO: 1 (or any corresponding glutamic acid or aspartic acid residue in an amino acid sequence homologous to SEQ ID NO: 1) is replaced by an amide group, according to any of the respective embodiments described herein.

In some embodiments of any of the embodiments described herein, at least Glu39 in SEQ ID NO: 1 (or any corresponding glutamic acid or aspartic acid residue in an amino acid sequence homologous to SEQ ID NO: 1) is replaced by an amide group, according to any of the respective embodiments described herein.

In some embodiments of any of the embodiments described herein, at least Glu69 in SEQ ID NO: 1 (or any corresponding glutamic acid or aspartic acid residue in an amino acid sequence homologous to SEQ ID NO: 1) is replaced by an amide group, according to any of the respective embodiments described herein.

In some embodiments of any of the embodiments described herein, at least Glu78 in SEQ ID NO: 1 (or any corresponding glutamic acid or aspartic acid residue in an amino acid sequence homologous to SEQ ID NO: 1) is replaced by an amide group, according to any of the respective embodiments described herein.

In some embodiments of any of the embodiments described herein, at least Glu102 in SEQ ID NO: 1 (or any corresponding glutamic acid or aspartic acid residue in an amino acid sequence homologous to SEQ ID NO: 1) is replaced by an amide group, according to any of the respective embodiments described herein.

In some embodiments of any of the embodiments described herein, at least Glu112 in SEQ ID NO: 1 (or any corresponding glutamic acid or aspartic acid residue in an amino acid sequence homologous to SEQ ID NO: 1) is replaced by an amide group, according to any of the respective embodiments described herein.

In some embodiments of any of the embodiments described herein, at least Glu124 in SEQ ID NO: 1 (or any corresponding glutamic acid or aspartic acid residue in an amino acid sequence homologous to SEQ ID NO: 1) is replaced by an amide group, according to any of the respective embodiments described herein.

In some embodiments of any of the embodiments described herein, at least Glu127 in SEQ ID NO: 1 (or any corresponding glutamic acid or aspartic acid residue in an amino acid sequence homologous to SEQ ID NO: 1) is replaced by an amide group, according to any of the respective embodiments described herein.

In some embodiments of any of the embodiments described herein, at least Glu143 in SEQ ID NO: 1 (or any corresponding glutamic acid or aspartic acid residue in an amino acid sequence homologous to SEQ ID NO: 1) is replaced by an amide group, according to any of the respective embodiments described herein.

In some embodiments of any of the embodiments described herein, at least Glu156 in SEQ ID NO: 1 (or any corresponding glutamic acid or aspartic acid residue in an amino acid sequence homologous to SEQ ID NO: 1) is replaced by an amide group, according to any of the respective embodiments described herein.

In some embodiments of any of the embodiments described herein, at least Glu161 in SEQ ID NO: 1 (or any corresponding glutamic acid or aspartic acid residue in an amino acid sequence homologous to SEQ ID NO: 1) is replaced by an amide group, according to any of the respective embodiments described herein.

In some embodiments of any of the embodiments described herein, at least Glu256 in SEQ ID NO: 1 (or any corresponding glutamic acid or aspartic acid residue in an amino acid sequence homologous to SEQ ID NO: 1) is replaced by an amide group, according to any of the respective embodiments described herein.

In some embodiments of any of the embodiments described herein, at least Asp33 in SEQ ID NO: 1 (or any corresponding glutamic acid or aspartic acid residue in an amino acid sequence homologous to SEQ ID NO: 1) is replaced by an amide group, according to any of the respective embodiments described herein.

In some embodiments of any of the embodiments described herein, at least Asp42 in SEQ ID NO: 1 (or any corresponding glutamic acid or aspartic acid residue in an amino acid sequence homologous to SEQ ID NO: 1) is replaced by an amide group, according to any of the respective embodiments described herein.

In some embodiments of any of the embodiments described herein, at least Asp58 in SEQ ID NO: 1 (or any corresponding glutamic acid or aspartic acid residue in an amino acid sequence homologous to SEQ ID NO: 1) is replaced by an amide group, according to any of the respective embodiments described herein.

In some embodiments of any of the embodiments described herein, at least Asp61 in SEQ ID NO: 1 (or any corresponding glutamic acid or aspartic acid residue in an amino acid sequence homologous to SEQ ID NO: 1) is replaced by an amide group, according to any of the respective embodiments described herein.

In some embodiments of any of the embodiments described herein, at least Asp87 in SEQ ID NO: 1 (or any corresponding glutamic acid or aspartic acid residue in an amino acid sequence homologous to SEQ ID NO: 1) is replaced by an amide group, according to any of the respective embodiments described herein.

In some embodiments of any of the embodiments described herein, at least Asp93 in SEQ ID NO: 1 (or any corresponding glutamic acid or aspartic acid residue in an amino acid sequence homologous to SEQ ID NO: 1) is replaced by an amide group, according to any of the respective embodiments described herein.

In some embodiments of any of the embodiments described herein, at least Asp98 in SEQ ID NO: 1 (or any corresponding glutamic acid or aspartic acid residue in an amino acid sequence homologous to SEQ ID NO: 1) is replaced by an amide group, according to any of the respective embodiments described herein.

In some embodiments of any of the embodiments described herein, at least Asp99 in SEQ ID NO: 1 (or any corresponding glutamic acid or aspartic acid residue in an amino acid sequence homologous to SEQ ID NO: 1) is replaced by an amide group, according to any of the respective embodiments described herein.

In some embodiments of any of the embodiments described herein, at least Asp107 in SEQ ID NO: 1 (or any corresponding glutamic acid or aspartic acid residue in an amino acid sequence homologous to SEQ ID NO: 1) is replaced by an amide group, according to any of the respective embodiments described herein.

In some embodiments of any of the embodiments described herein, at least Asp139 in SEQ ID NO: 1 (or any corresponding glutamic acid or aspartic acid residue in an amino acid sequence homologous to SEQ ID NO: 1) is replaced by an amide group, according to any of the respective embodiments described herein.

In some embodiments of any of the embodiments described herein, at least Asp145 in SEQ ID NO: 1 (or any corresponding glutamic acid or aspartic acid residue in an amino acid sequence homologous to SEQ ID NO: 1) is replaced by an amide group, according to any of the respective embodiments described herein.

In some embodiments of any of the embodiments described herein, at least Asp149 in SEQ ID NO: 1 (or any corresponding glutamic acid or aspartic acid residue in an amino acid sequence homologous to SEQ ID NO: 1) is replaced by an amide group, according to any of the respective embodiments described herein.

In some embodiments of any of the embodiments described herein, at least Asp153 in SEQ ID NO: 1 (or any corresponding glutamic acid or aspartic acid residue in an amino acid sequence homologous to SEQ ID NO: 1) is replaced by an amide group, according to any of the respective embodiments described herein.

In some embodiments of any of the embodiments described herein, at least Asp162 in SEQ ID NO: 1 (or any corresponding glutamic acid or aspartic acid residue in an amino acid sequence homologous to SEQ ID NO: 1) is replaced by an amide group, according to any of the respective embodiments described herein.

In some embodiments of any of the embodiments described herein, at least Asp168 in SEQ ID NO: 1 (or any corresponding glutamic acid or aspartic acid residue in an amino acid sequence homologous to SEQ ID NO: 1) is replaced by an amide group, according to any of the respective embodiments described herein.

In some embodiments of any of the embodiments described herein, at least Asp198 in SEQ ID NO: 1 (or any corresponding glutamic acid or aspartic acid residue in an amino acid sequence homologous to SEQ ID NO: 1) is replaced by an amide group, according to any of the respective embodiments described herein.

In some embodiments of any of the embodiments described herein, at least Asp201 in SEQ ID NO: 1 (or any corresponding glutamic acid or aspartic acid residue in an amino acid sequence homologous to SEQ ID NO: 1) is replaced by an amide group, according to any of the respective embodiments described herein.

In some embodiments of any of the embodiments described herein, at least Asp212 in SEQ ID NO: 1 (or any corresponding glutamic acid or aspartic acid residue in an amino acid sequence homologous to SEQ ID NO: 1) is replaced by an amide group, according to any of the respective embodiments described herein.

In some embodiments of any of the embodiments described herein, at least Asp228 in SEQ ID NO: 1 (or any corresponding glutamic acid or aspartic acid residue in an amino acid sequence homologous to SEQ ID NO: 1) is replaced by an amide group, according to any of the respective embodiments described herein.

In some embodiments of any of the embodiments described herein, at least Asp243 in SEQ ID NO: 1 (or any corresponding glutamic acid or aspartic acid residue in an amino acid sequence homologous to SEQ ID NO: 1) is replaced by an amide group, according to any of the respective embodiments described herein.

In some embodiments of any of the embodiments described herein, at least Asp251 in SEQ ID NO: 1 (or any corresponding glutamic acid or aspartic acid residue in an amino acid sequence homologous to SEQ ID NO: 1) is replaced by an amide group, according to any of the respective embodiments described herein.

DNase I:

Except where modified DNase I is explicitly referred to, the following section described the DNase I which is homologous to the modified DNase I described herein except for the non-cellularly modified amino acid residues as described herein, according to any one of the embodiments described herein. That is, the DNase I described herein refers to the non-modified protein in the absence of any non-cellularly modified amino acid residue according to any of the respective embodiments described herein.

The skilled person will understand the structure of a modified DNase I protein according to embodiments of the invention by considering the non-modified DNase I according to any one of the embodiments described in this section in combination with a modification thereof according to any one of the respective embodiments described herein.

As used herein the terms "DNase I" and "DNase I protein" refer to a deoxyribonuclease I (EC 3.1.21.1) polypeptide. DNase I is classified as an endonuclease, which cleaves DNA to produce 5'-phosphodinucluotide and 5'-phosphooligonucleotide end products, with a preference for double stranded DNA substrates and alkaline pH optimum.

DNase I acts on single-stranded DNA, double-stranded DNA, and chromatin.

The DNase I according to some embodiment of the present teachings (i.e., non-modified) is inhibited by actin.

The DNase I according to some embodiment of the present teachings (i.e., non-modified) is not inhibited by actin.

Herein, the phrase "inhibited by actin" refers to a reduction of at least 20% in a DNA hydrolytic activity (e.g., of a DNase enzyme) in the presence of 50 µg/ml human non-muscle actin (relative to the activity in the absence of actin).

In some embodiments of any of the embodiments described herein relating to a non-modified DNase I which is inhibited by actin, a DNA hydrolytic activity of the DNase I is reduced by at least 30% in the presence of 50 µg/ml human non-muscle actin. In some embodiments, the DNA hydrolytic activity of the DNase is reduced by at least 40% in the presence of 50 µg/ml human non-muscle actin. In some embodiments, the DNA hydrolytic activity of the DNase is reduced by at least 50% in the presence of 50 µg/ml human non-muscle actin. In some embodiments, the DNA hydrolytic activity of the DNase is reduced by at least 60% in the presence of 50 µg/ml human non-muscle actin. In some embodiments, the DNA hydrolytic activity of the DNase is reduced by at least 70% in the presence of 50 µg/ml human non-muscle actin. In some embodiments, the DNA hydrolytic activity of the DNase is reduced by at least 80% in the presence of 50 µg/ml human non-muscle actin. In exemplary embodiments, the DNA hydrolytic activity of the DNase is reduced by at least 90% in the presence of 50 µg/ml human non-muscle actin (e.g., as exemplified in FIG. 37).

Contemplated herein are DNase I enzymes of the E.C. 3.1.21.1 class.

According to a specific embodiment, the DNase I is human DNase I as set forth in SEQ ID NO: 1.

Also contemplated are homologs (i.e., functional equivalents) and orthologs (e.g., mouse NM_010061.5 NO_034191.3) of the human DNase I having the DNase I activity.

Such homologues can be, for example, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to SEQ ID NO: 1 or homologous (identity+homology), as determined using the BestFit software of the Wisconsin sequence analysis package, utilizing the Smith and Waterman algorithm, where gap weight equals 50, length weight equals 3, average match equals 10 and average mismatch equals −9.

Embodiments of the invention encompasses nucleic acid sequences described hereinabove; fragments thereof, sequences hybridizable therewith, sequences homologous thereto, sequences orthologous thereto, sequences encoding similar polypeptides with different codon usage, altered sequences characterized by mutations, such as deletion, insertion or substitution of one or more nucleotides, either naturally occurring or man induced, either randomly or in a targeted fashion, all of which are collectively termed "substantial homologs").

The phrase "substantially homologous" when used to describe the amino acid sequence of a DNase I protein which is modified to provide the modified DNase I, also refers herein to an amino acid sequence having at least 80% homology, optionally at least 90% homology, optionally at least 95% homology, optionally at least 98% homology, and optionally at least 99% homology to another amino acid sequence of a DNase I protein as described in detail herein.

Other members of the DNase I family of endonucleases are DNase X, DNase lambda, DNASIL2 and tear lipocalin in humans. DNase I also encompasses, inter alia, alkaline DNase, bovine pancreatic (bp) DNase, DNase A, DNA phosphatase and DNA endonuclease, for example, in Bos taurus.

The non-modified DNase I can be a purified DNase I which is extracted from a cell/tissue in which it is naturally expressed.

Alternatively or additionally, the DNase I is recombinantly produced.

For recombinant expression, the nucleic acid sequence encoding DNase is ligated into a nucleic acid expression vector under the transcriptional regulation of a cis-acting regulatory element e.g., a promoter.

Other than containing the necessary elements for the transcription and translation of the inserted coding sequence, the expression construct of some embodiments of the invention can also include sequences engineered to enhance stability, production, purification, yield or toxicity of the expressed peptide. A variety of prokaryotic or eukaryotic cells can be used as host-expression systems to express the DNase I of some embodiments of the invention. These include, but are not limited to, microorganisms, such as bacteria transformed with a recombinant bacteriophage DNA, plasmid DNA or cosmid DNA expression vector containing the coding sequence; yeast transformed with recombinant yeast expression vectors containing the coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the coding sequence. Mammalian expression systems can also be used to express the polypeptides of some embodiments of the invention.

Examples of bacterial constructs include the pET series of E. coli expression vectors [Studier et al. (1990) Methods in Enzymol. 185:60-89).

In yeast, a number of vectors containing constitutive or inducible promoters can be used, as disclosed in U.S. Pat. No. 5,932,447. Alternatively, vectors can be used which promote integration of foreign DNA sequences into the yeast chromosome.

In cases where plant expression vectors are used, the expression of the coding sequence can be driven by a number of promoters. For example, viral promoters such as the 35S RNA and 19S RNA promoters of CaMV [Brisson et al. (1984) Nature 310:511-514], or the coat protein promoter to TMV [Takamatsu et al. (1987) EMBO J. 6:307-311] can be used. Alternatively, plant promoters such as the small subunit of RUBISCO [Coruzzi et al. (1984) EMBO J. 3:1671-1680 and Brogli et al., (1984) Science 224:838-843] or heat shock promoters, e.g., soybean hsp17.5-E or hsp17.3-B [Gurley et al. (1986) Mol. Cell. Biol. 6:559-565] can be used. These constructs can be introduced into plant cells using Ti plasmid, Ri plasmid, plant viral vectors, direct DNA transformation, microinjection, electroporation and other techniques well known to the skilled artisan. See, for example, Weissbach & Weissbach, 1988, Methods for Plant Molecular Biology, Academic Press, NY, Section VIII, pp 421-463.

According to a specific embodiment, the DNase I is produced in a plant cell suspension culture as described in WO2013/114374, and is also referred to as PRX-110, which is hereby incorporated by reference in its entirety.

Accordingly, at least a portion of the human DNase I protein has an N-terminal glycine residue (SEQ ID NO: 2). In some embodiments, the human DNase I protein comprises a mixture of DNase I as set forth in SEQ ID NO: 2 and DNase I as set forth in SEQ ID NO: 1.

Such a protein is expressed from a nucleic acid construct which comprises a nucleic acid sequence encoding human DNase I translationally fused at the N-terminus thereof to an Arabidopsis ABPI endoplasmic reticulum targeting signal peptide encoded by a nucleic acid sequence as set forth in SEQ ID NO: 3.

As used herein, the term "Arabidopsis ABPI endoplasmic reticulum targeting signal peptide" refers to the leader peptide sequence of the Arabidopsis thaliana auxin binding protein, which is capable of directing the expressed protein to the endoplasmic reticulum within the plant cell. In one embodiment, the Arabidopsis ABPI endoplasmic reticulum targeting signal peptide is a 33 amino acid polypeptide as set forth in SEQ ID NO: 8.

Thus, according to some embodiments, the human DNase I protein contiguously linked at the N-terminal to an Arabidopsis ABPI endoplasmic reticulum targeting signal peptide and the human DNase I protein has an amino acid sequence as set forth in SEQ ID NO: 9.

The human DNase I protein may optionally be encoded by a nucleic acid sequence as set forth in SEQ ID NO: 6. The Arabidopsis ABPI endoplasmic reticulum targeting signal peptide may optionally be encoded by a nucleic acid sequence as set forth in SEQ ID NO: 3. A human DNase I protein contiguously linked at the N-terminus to an Arabidopsis ABPI endoplasmic reticulum targeting signal peptide may optionally be encoded by a nucleic acid sequence as set forth in SEQ ID NO: 7.

Further presented herein are a native nucleic acid sequence (SEQ ID NO: 4) encoding a native human DNase I protein (SEQ ID NO: 5; GenBank: NM_005223, sequence (a)) which includes the native signal leader peptide.

Other expression systems such as insects and mammalian host cell systems which are well known in the art and are further described herein below can also be used by some embodiments of the invention.

According to some embodiments of any of the embodiments described herein relating to a human DNase I, the DNase I is mature human DNase I. In some embodiments, the DNase I is dornase alfa DNase I (e.g., Pulmozyme®).

According to some embodiments of any of the embodiments described herein, the human DNase I comprises an amino acid sequence as set forth in SEQ ID NO: 1.

It will be appreciated that a DNase I protein having an amino acid sequence homologous (e.g., at least 80% homologous, as described herein) to the human DNase I amino acid sequence of SEQ ID NO: 1 may optionally maintain characteristic structure and/or function of the human DNase I. One non-limiting example of an amino acid sequence homologous to an amino acid sequence of a human DNase I protein is SEQ ID NO: 2, which is closely similar to SEQ ID NO: 1.

In some embodiments of any of the embodiments described herein, the DNase I protein is a variant human DNase I protein, optionally a naturally occurring (in at least some humans) variant of human DNase I. Variant human DNase proteins, having altered catalytic and/or other biochemical and structural properties, such as altered actin affinity, cofactor requirements, pH optimum, increased shelf life in storage and the like, enhanced recombinant expression or fusion proteins have been disclosed. Suitable modified DNase I polypeptides include, but are not limited to DNase polypeptides disclosed in U.S. Pat. Nos. 6,348,343, 6,391,607, 7,407,785 and 7,297,526, and in International Patent Application Publications WO 96/26279, WO 2008/039989 and WO 2013/114374, each of which is incorporated by reference in its entirely, especially with respect to DNase polypeptides and methods of preparing them.

In some embodiments, the DNase I is expressed in tobacco (e.g., Nicotiana tabacum cells), which may optionally be in suspension, for example, DNase I expressed in Bright Yellow-2 (BY2) cell culture (e.g., as exemplified herein below, and/or as described in International Patent Application Publication WO 2013/114374).

In some embodiments, Agrobacterium mediated transformation is used to introduce foreign genes into a plant cell genome. This technique is based on the natural capability of the agrobacterium to transform plant cells by transferring a plasmid DNA segment, the transferred DNA (T-DNA), into the host cell genome. Using this approach, a T-DNA molecule, consisting of a foreign gene and its regulatory elements, is randomly introduced into the plant genome. The site of integration, as well as the copy number of the gene insertions is not controlled, thus the transformation process results in a 'pool' of transgenic cells composed of cells with various levels of expression of the transgene. The transgenic 'pool' is subsequently used for clone isolation. Clone isolation results in the establishment of many single cell lines, from which the clone with the highest expression level of the foreign gene is then selected. In some embodiments the Agrobacterium mediated transformation is used to introduce foreign genes into a genome of a tobacco cell, such as, but not limited to Nicotiana tabacum L. cv Bright Yellow (BY-2) cells.

In some embodiments of any of the embodiments described herein, molecular mass of the DNase I (e.g., plant-recombinant human DNase I) polypeptide is similar to the molecular mass, as measured by PAGE and/or mass spectrometry, of recombinant human DNase I expressed in mammalian cells (Pulmozyme® DNase I).

In some embodiments of any of the embodiments described herein, the DNase I (e.g., plant-recombinant human DNase I) polypeptide has a molecular mass of about 30 kDa, as measured by SDS-PAGE, and about 32 kDa, as measured by mass spectrometry.

In some embodiments of any of the embodiments described herein, the non-modified DNase I (e.g., plant-recombinant human DNase I) is glycosylated.

In some embodiments of any of the embodiments described herein, the modified DNase I (e.g., plant-recombinant human DNase I) is glycosylated.

In some embodiments of any of the embodiments described herein, the isoelectric point of the glycosylated DNase I (e.g., plant-recombinant human DNase I) protein is at a higher pH than that of recombinant human DNase I expressed in mammalian cells (Pulmozyme®).

When a range of isoelectric points occurs (e.g., a band is observed upon isoelectric focusing), the "isoelectric point" of a DNase I refers herein to an average isoelectric point.

Without being bound by any particular theory, it is believed that a combination of a higher isoelectric point (suggesting a less negative charge) in comparison to DNase I expressed in mammalian cells (as exemplified herein with plant recombinant DNase I) and a reduction in negative charge associated with modification of negatively carboxylic acid groups and/or introduction of positively charged amine groups (according to any of the embodiments described herein relating to non-cellular modification), may enhance affinity of the DNase to negatively charged DNA, thereby reducing the Michaelis constant.

In some embodiments of any of the embodiments described herein, a heterogeneity in the electrophoretic mobility of the glycosylated DNase I (e.g., plant-recombinant human DNase I) protein is greater than that of recombinant human DNase I expressed in mammalian cells (Pulmozyme®). For example, an electrophoresis band of the glycosylated DNase I may be broader than that of recombinant human DNase I expressed in mammalian cells.

In some embodiments of any of the embodiments described herein, the DNase I (e.g., plant-recombinant human DNase I) is a glycosylated protein, comprising a polypeptide moiety having a molecular mass of about 29 kDa.

In some embodiments of any of the embodiments described herein, the modified and/or non-modified DNase I is a purified protein, optionally characterized by a purity (e.g., of DNase I in a composition described herein) of at least 85%, at least 87%, at least 90%, at least 91%, at least 91.5%, at least 92%, at least 92.5%, at least 93%, at least 93.1%, at least 93.2%, at least 93.3%, at least 93.4%, at least 93.5%, at least 93.6%, at least 93.7%, at least 93.8%, at least 93.9%, at least 94%, at least 94.5%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, in a range of at least 95.0-99.8% or 100% purity. In some embodiments, purity of the modified and/or non-modified DNase I protein is measured by HPLC.

The purity described hereinabove refers to low levels (or absence) of impurities. Ingredients deliberately added to a composition comprising modified and/or non-modified DNase I (e.g., any ingredients of a composition such as described herein) are not considered herein as impurities which affect the purity of the DNase I protein.

In some embodiments, the DNase I is a recombinant DNase I, optionally a plant-recombinant human DNase I, and the purity described hereinabove refers to low levels (or absence) of impurities derived from the medium into which the DNase I protein is secreted and/or from the host cell (e.g., plant host cell), such as, but not limited to nucleic acids and polynucleotides, amino acids, oligopeptides and polypeptides, glycans and other carbohydrates, lipids and the like. In some embodiments the host-cell derived impurities comprise biologically active molecules, such as enzymes.

In some embodiments of any one of the embodiments described herein, the DNase I protein (e.g., plant-recombinant DNase I) is glycosylated, such that a plurality of DNase I polypeptide molecules has an average of at least 0.2, optionally at least 0.5, optionally at least one, optionally at least two, optionally at least three or optionally at least four or more exposed mannose residues per polypeptide molecule.

Herein, an "exposed" residue refers to a monosaccharide residue attached to a non-reducing end of a glycan by only one covalent bond.

In some embodiments of any one of the embodiments described herein, the DNase I protein (e.g., plant-recombinant DNase I) is glycosylated, such that a plurality of DNase I polypeptide molecules has an average of at least one, and optionally at least two, core xylose residues per polypeptide molecule.

In some embodiments of any one of the embodiments described herein, the DNase I protein (e.g., plant-recombinant DNase I) is glycosylated, such that a plurality of DNase I polypeptide molecules has an average of at least 0.2, optionally at least 0.5, optionally at least one, and optionally about two, core α-(1,3) fucose residues per polypeptide molecule.

In some embodiments of any one of the embodiments described herein, the DNase I protein (e.g., plant-recombinant DNase I) is glycosylated, such that a plurality of DNase polypeptide molecules has an average of at least one core xylose residue and at least one α-(1,3) fucose residue per polypeptide molecule.

In some embodiments of any one of the embodiments described herein, the DNase I protein (e.g., plant-recombinant DNase I) is glycosylated, such that a plurality of DNase polypeptide molecules has an average of at least one exposed mannose residue, at least one core xylose residue and at least one α-(1,3) fucose residue per polypeptide molecule.

In some embodiments of any one of the embodiments described herein, the DNase I protein (e.g., plant-recombinant DNase I) is glycosylated, such that a plurality of DNase polypeptide molecules has an average of at least one, optionally at least two, optionally at least 3, and optionally at least 4 terminal N-acetyl glucosamine substitutions per polypeptide molecule on the outer (distal from the polypeptide) mannose residues.

In some embodiments of any one of the embodiments described herein, the DNase I protein (e.g., plant-recombinant DNase I) is devoid of sialic acid residues.

Herein, "devoid of sialic acid residues" means that less than 1% of glycans contain a sialic acid residue, optionally less than 0.1%, and optionally less than 0.01%.

Some or all of the abovementioned characteristics regarding glycosylation may be obtained in plant-recombinant DNase I (according to any of the respective embodiments described herein), which may optionally exhibit high mannose glycosylation (e.g., exposed mannose sugar residues and/or more than 3 mannose residues per glycan) and plant specific glycan residues.

Preparation:

According an aspect of some embodiments of the invention, there is provided a process for preparing the modified DNase I protein according to any of the respective embodiments described herein. The process comprises reacting the DNase I protein according to any of the respective embodiments described herein with an amine-containing compound in the presence of a coupling agent.

Suitable coupling agents for reacting a carboxylic acid and amine to form an amide are known in the art, for example, coupling agent described by F. Albericio, S. A. Kates, Solid-Phase Synthesis: A Practical Guide, S. A. Kates, F. Albericio Eds; Marcel Dekker, New York, N.Y., 2000, pp. 273-328 and F. Albericio et al., Org. Prep. Proc. Int., 33, 202 (2001)]. Examples of coupling agents include, without limitation, carbodiimides, and benzotriazole derivatives such as phosphonium and aminium/uronium salts of hydroxybenzotriazole derivatives (e.g., 2-(7-aza-1H-benzotriazole-1-yl)-1,1,3,3-tetramethyluronium hexafluorophosphate (HATU), benzotriazol-1-yl-N-oxy-tris(pyrrolidino) phosphonium hexafluorophosphate (PyB OP), 7-azabenzotriazol-1-yl-N-oxy-tris(pyrrolidino)phosphonium hexafluorophosphate (PyAOP)).

In some embodiments, the coupling agent is a carbodiimide.

Without being bound by any particular theory, it is believed that the carbodiimide reacts first with carboxylic acid groups of the DNase I protein to form an intermediate with activated carboxylic acid groups, and the amine-containing compound reacts with the intermediate, thereby forming modified DNase I with amide groups replacing carboxylic acid groups.

Herein, the term "carbodiimide" refers to a compound having the formula R'N=C=NR", wherein R' and R" are as defined herein.

In some embodiments of any of the embodiments described herein, the carbodiimide is selected from the group consisting of EDC (1-ethyl-3-((3-dimethylaminopropyl)carbodiimide), CMC (N-cyclohexyl-N'-(2-morpholinoethyl)carbodiimide metho-p-toluenesulfonate) and DIC (diisopropylcarbodiimide). In some embodiments, the carbodiimide is EDC and/or CMC. In some embodiments, the carbodiimide is EDC. In some embodiments, the carbodiimide is CMC.

In some embodiments of any of the embodiments described herein, the carbodiimide is water-soluble. EDC is an exemplary water-soluble carbodiimide.

Herein, the phrase "amine-containing compound" refers to any compound which comprises one or more amine groups (as defined herein).

In some embodiments of any of the embodiments described herein, the amine-containing compound comprises a primary amine or secondary amine group, such that the compound has the formula HNR'R", wherein R' and R" are as defined herein.

In some embodiments of any of the embodiments described herein, the amine-containing compound has the general formula $H_2NR'$, wherein R' is selected from the group consisting of alkyl, alkenyl and alkynyl, each being non-substituted or substituted with one or more substituents selected from the group consisting of hydroxy and amino, according to any the respective embodiments described herein.

Examples of amine-containing compounds include non-substituted monoamines such as butylamine and other non-substituted alkylamines; substituted monoamines, such as ethanolamine and Tris (i.e., tris(hydroxymethyl)aminomethane); diamines such as ethylene diamine, hexamethylene diamine and other alkylene diamines; and ammonia (or salts thereof, such as ammonium chloride).

In some embodiments of any of the embodiments described herein, the amine-containing compound is not ammonia (or a salt thereof).

In some embodiments of any of the embodiments described herein, reacting the DNase I, coupling agent (optionally a carbodiimide) and amine-containing compound is performed in an aqueous liquid. In some embodiments, a pH of the aqueous liquid is in a range of 6 or less. In some embodiments, the pH is in a range of from 3.5 to 6. In some embodiments, the pH is in a range of from 3.5 to 5.5. In some embodiments, the pH is in a range of from 4.5 to 5.5. In some embodiments, the pH is 5.

In some embodiments of any of the embodiments described herein, the aqueous liquid is a buffer solution, for example, a buffer solution suitable for providing a pH according to any of the respective embodiments. Suitable buffers include solutions of phosphate, Tris and MES (2-(N-morpholino)ethanesulfonic acid), optionally at concentrations of about 0.1 M. In some embodiments, the aqueous liquid is a solution comprising MES.

In some embodiments of any of the embodiments described herein, reacting the DNase I, coupling agent (optionally a carbodiimide) and amine-containing compound is performed for at least 1 hour; in some embodiments, for at least 2 hours; and in some embodiments, for at least 3 hours. In some embodiments, the reacting is performed for about 2.5 hours.

In some embodiments of any of the embodiments described herein, the reaction is terminated by removing the amine-containing compound, thereby separating between the amine-containing compound and the DNase I. In some embodiments, terminating the reaction further comprises removing the coupling agent (e.g., carbodiimide). Removal of an amine-containing compound and/or coupling agent may be performed by replacing a medium in which the reaction is performed. Dialysis (e.g., as described in the Examples section herein) is an example of a suitable technique for removing an amine-containing compound and/or coupling agent.

In some embodiments of any of the embodiments described herein, the concentration of DNase I being reacted is in a range of from 0.1 to 10 mg/ml. In some embodiments, the concentration is in a range of from 0.3 to 3 mg/ml. In some embodiments, the concentration is in a range of from 0.5 to 2 mg/ml. In some embodiments, the concentration is in a range of from 0.75 to 1.5 mg/ml. In some embodiments, the concentration is about 1 mg/ml.

The temperature at which the reaction is performed is preferably selected so as to avoid precipitation of DNase I. In some embodiments, the temperature is less than 50° C., optionally less than 40° C.

In some embodiments of any of the embodiments described herein, reacting the DNase I and carbodiimide is performed using at least 10 molar equivalents of carbodiimide, that is, at least 10 molecules of carbodiimide per DNase I molecule. In some embodiments, from 10 to 200 molar equivalents of carbodiimide are used. In some embodiments, from 100 to 200 molar equivalents of carbodiimide are used. In some embodiments, from 10 to 100 molar equivalents of carbodiimide are used. In some embodiments, from 10 to 40 molar equivalents of carbodiimide are used. In some embodiments, from 30 to 70 molar equivalents of carbodiimide are used. In some embodiments, from 50 to 80 molar equivalents of carbodiimide are used. In some embodiments, about 60 or about 70 molar equivalents of carbodiimide are used. In some such embodiments, the concentration of DNase I being reacted is in a range of from 0.1 to 10 mg/ml, according to any of the respective embodiments described herein.

In some embodiments of any of the embodiments described herein, reacting the DNase I and carbodiimide is performed using at least 15 molar equivalents of carbodiimide. In some embodiments, from 15 to 100 molar equivalents of carbodiimide are used. In some embodiments, from 15 to 40 molar equivalents of carbodiimide are used. In some such embodiments, the concentration of DNase I being reacted is in a range of from 0.1 to 10 mg/ml, according to any of the respective embodiments described herein.

Without being bound by any particular theory, it is believed that the molar ratios of carbodiimide to DNase I described herein are suitable providing desired amidation, which may be impeded if the amount of carbodiimide is low, while reducing a degree of dimerization of DNase I, which is associated with relatively high carbodiimide amounts.

In some embodiments of any of the embodiments described herein, reacting the DNase I, amine-containing compound and coupling agent (e.g., carbodiimide) is performed in a presence of a calcium ion concentration in a range of from 0 to 100 mM. In some embodiments, the calcium ion concentration is from 0 to 50 mM. In some embodiments, the calcium ion concentration is from 0 to 25 mM. In some embodiments, the calcium ion concentration is from 0 to 10 mM. In some embodiments, the calcium ion concentration is from 0 to 5 mM. In some embodiments, the calcium ion concentration is from 0 to 2 mM. In some embodiments, the calcium ion concentration is from 0 to 1 mM.

In some embodiments of any of the embodiments described herein, reacting the DNase I, amine-containing compound and coupling agent (e.g., carbodiimide) is performed in a presence of a calcium ion concentration of at least 1 mM. In some embodiments, the calcium ion concentration is from 1 to 100 mM. In some embodiments, the calcium ion concentration is from 1 to 50 mM. In some embodiments, the calcium ion concentration is from 1 to 25 mM. In some embodiments, the calcium ion concentration is from 1 to 10 mM. In some embodiments, the calcium ion concentration is from 1 to 5 mM. In some embodiments, the calcium ion concentration is from 1 to 2 mM.

In some embodiments of any of the embodiments described herein, reacting the DNase I, amine-containing compound and coupling agent (e.g., carbodiimide) is performed in a presence of a calcium ion concentration of at least 5 mM. In some embodiments, the calcium ion concentration is from 5 to 100 mM. In some embodiments, the calcium ion concentration is from 5 to 50 mM. In some embodiments, the calcium ion concentration is from 5 to 25 mM. In some embodiments, the calcium ion concentration is from 5 to 10 mM.

In some embodiments of any of the embodiments described herein, reacting the DNase I, amine-containing compound and coupling agent (e.g., carbodiimide) is performed in a presence of a calcium ion concentration of at least 50 mM. In some embodiments, the calcium ion concentration is from 50 to 100 mM.

Without being bound by any particular theory, it is believed that relatively low calcium concentration may be useful for obtaining a higher reaction conversion, whereas a relatively high calcium concentration may be useful for reducing dimerization of DNase I.

Pharmaceutical Composition:

The modified DNase I protein according to any one of the respective embodiments described herein can be used to produce a pharmaceutical composition.

The pharmaceutical composition can be used for treatment or prevention of any condition or disease by any route of administration.

According to another aspect of the present invention there is provided a pharmaceutical composition which includes, as an active ingredient thereof, a modified DNase I protein (according to any of the respective embodiments described herein) and a pharmaceutical acceptable carrier.

As used herein a "pharmaceutical composition" refers to a preparation of one or more of the active ingredients described herein with other chemical components such as pharmaceutically acceptable carriers and excipients. The purpose of a pharmaceutical composition is to facilitate administration of a compound to an organism.

Herein the term "active ingredient" refers to the modified DNase I protein (according to any of the respective embodiments described herein) accountable for the biological effect.

Hereinafter, the phrase "pharmaceutically acceptable carrier" refers to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

In some embodiments of any of the embodiments described herein, a concentration of the modified DNase I in the composition is at least 0.2 mg/ml. In some embodiments, a concentration of the modified DNase I in the composition is at least 0.5 mg/ml. In some embodiments, a concentration of the modified DNase I in the composition is at least 1 mg/ml. In some embodiments, a concentration of the modified DNase I in the composition is at least 2 mg/ml. In some embodiments, a concentration of the modified DNase I in the composition is at least 5 mg/ml.

In some embodiments of any of the embodiments described herein, a concentration of the modified DNase I in the composition is in a range of from 0.2 to 20 mg/ml. In some embodiments, a concentration of the modified DNase I in the composition is in a range of from 0.5 to 20 mg/ml. In some embodiments, a concentration of the modified DNase I in the composition is in a range of from 1 to 20 mg/ml. In some embodiments, a concentration of the modified DNase I in the composition is in a range of from 2 to 10 mg/ml. In some embodiments, a concentration of the modified DNase I in the composition is about 5 mg/ml.

In some embodiments of any of the embodiments described herein, the pharmaceutical composition further comprises a calcium salt in an amount effective for enhancing a stability of the modified DNase I against heat stress (e.g., exposure to a temperature above 40° C. for 2 hours). In some embodiments, the calcium salt comprises (and optionally consists essentially of) calcium chloride ($CaCl_2$).

In some embodiments of any of the embodiments described herein, a concentration of calcium ions in the composition is at least 2 mM. In some embodiments, a concentration of calcium ions in the composition is at least 5 mM. In some embodiments, a concentration of calcium ions in the composition is at least about 10 mM, optionally about 10 mM.

In some embodiments of any of the embodiments described herein, a concentration of calcium ions in the composition is in a range of from 2 mM to 20 mM. In some embodiments, a concentration of calcium ions in the composition is in a range of from 5 mM to 15 mM. In some embodiments, a concentration of calcium ions in the composition is about 10 mM. In some embodiments, the calcium chloride ions are in a form of calcium chloride (e.g., about 10 mM calcium chloride).

In some embodiments of any of the embodiments described herein, the pharmaceutical composition further comprises a polysorbate in an amount effective for enhancing a stability of the modified DNase I against shear stress. In some embodiments, the polysorbate comprises (and optionally consists essentially of) polysorbate 80.

In some embodiments of any of the embodiments described herein, a concentration of polysorbate (e.g., polysorbate 80) in the composition is at least 0.001 weight percent. In some embodiments, polysorbate (e.g., polysorbate 80) in the composition is at least 0.003 weight percent. In some embodiments, polysorbate (e.g., polysorbate 80) in the composition is at least about 0.01 weight percent, optionally about 0.01 weight percent.

In some embodiments of any of the embodiments described herein, a concentration of polysorbate (e.g., polysorbate 80) in the composition is in a range of from 0.001 to 0.1 weight percent. In some embodiments, a concentration of polysorbate (e.g., polysorbate 80) in the composition is in a range of from 0.003 to 0.03 weight percent. In some embodiments, a concentration of polysorbate in the composition is about 0.01 weight percent. In some embodiments, a concentration of polysorbate 80 in the composition is about 0.01 weight percent.

The pharmaceutically acceptable carrier (e.g., an aqueous carrier) may optionally comprise a solute (optionally NaCl) in a concentration which results in an isotonic solution.

An exemplary formulation comprises about 10 mM $CaCl_2$, about 0.01 weight percent polysorbate 80, about 140 mM NaCl, and about 5 mg/ml of the modified DNase I protein.

In some embodiments of any of the embodiments described herein, the pharmaceutical composition further comprises an additional active ingredient, for example, an agent which reduces actin inhibition of DNase I activity, such as one or more inorganic salt selected from the group consisting of potassium, magnesium, calcium, zinc, lithium, manganese, cadmium, nickel, cobalt, ammonium, polyamine and macrocyclic polyammonium salts; and/or polyaspartic acid and/or the actin severing protein gelsolin (e.g., as described by Bucki et al. [*J Cystic Fibrosis* 2015, 14:587-593]). Agents suitable for combination with the modified DNase I, for therapeutic applications such as treatment of pulmonary conditions (e.g., cystic fibrosis) are described in detail in U.S. Pat. No. 7,432,308, which is incorporated herein by reference in its entirety (especially with respect to teachings related to agents suitable for combination with DNase I, and for therapeutic applications of DNase I).

In some embodiments, combination of the modified DNase I with the additional active ingredient results in improvement, and optionally synergistic improvement, in reduction of a viscosity (e.g., as represented by a reduction in a shear loss modulus and/or a shear storage modulus) of sputum.

In some embodiments, the additional active ingredient is a magnesium salt, such as magnesium chloride or magnesium sulfate.

In some embodiments of any of the embodiments described herein, the pharmaceutical composition further comprises, or is administered along with, an additional pharmaceutical agent, the additional pharmaceutical agent including, but not limited to, one or more agents used to treat any one or more of the conditions listed herein, such as antibiotics e.g. including anti-pseudomonal and/or anti-staphylococcal therapy (e.g., tobramycin, flucloxacillin), bronchodilators, anti-inflammatory agents, mucolytics (e.g. n-acetyl-cysteine), actin binding or actin severing proteins (e.g., gelsolin), protease inhibitors, or gene therapy product, e.g., comprising the cystic fibrosis transmembrane conductance regulator (CFTR) gene [Riordan et al., *Science* 245: 1066-1073 (1989)]. Additional pharmaceutical agents can be administered prior to, along with, subsequent to or in any other temporal combination with the pharmaceutical composition of embodiments of the invention.

Further addition ingredients which may optionally be included in the composition include, for example, any of the following ingredients, or compounds of a similar nature: a binder such as microcrystalline cellulose, gum tragacanth or gelatin; an excipient such as starch or lactose, a disintegrating agent such as alginic acid, Primogel™, or corn starch; a lubricant such as magnesium stearate or Sterotes™; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier. In addition, dosage unit forms can contain various other materials which modify the physical form of the dosage unit, for example, coatings of sugar, shellac, or other enteric agents.

Regimens for combination of the pharmaceutical composition of the invention with additional agents can be formulated according to parameters such as specific conditions or diseases, health status of the subject, methods and dose of administration, and the like. Determination of such combination regimen can be done, for example, by professionals such as attending physicians, hospital staff, and also according to predetermined protocols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

In some embodiments of any of the embodiments described herein, the pharmaceutical composition is formulated for pulmonary administration to a subject.

The compositions for use in the methods and compositions of the invention may be in a variety of forms according to the mode of inhalation and/or therapeutic application.

In some embodiments of any of the embodiments described, the pharmaceutical composition is formulated so as to be suitable for inhalation by a subject. Examples of pharmaceutical compositions which are suitable for inhalation include, but are not limited to, a propellant-containing aerosol, and a propellant-free inhalable solution or suspension. Such pharmaceutical compositions may optionally be formulated for administration utilizing a devices described herein. In some embodiments, the composition is a propellant-free inhalable solution comprising the modified DNase, which is suitable for being administered to the subject, for example, via a nebulizer. Other suitable preparations include, but are not limited to, mist, vapor, or spray preparations so long as the particles comprising the protein composition are delivered in a size range consistent with that described for the delivery device, e.g., a dry powder form of the pharmaceutical composition. In some embodiments, the composition is formulated for delivery via a nebulizer.

Where a liquid solution or suspension is used in a delivery device, a nebulizer, a metered dose inhaler, or other suitable delivery device delivers, in a single or multiple fractional dose, by pulmonary inhalation, a pharmaceutically effective amount of the composition to the subject's lungs as droplets, e.g., having the same particle size range described herein. Methods for preparing and using formulations suitable for use as liquid or suspension are known in the art, for example, the oil-based matrix taught in International Patent Application Publication WO 2011/004476.

Where the liquid pharmaceutical composition is lyophilized prior to use in the delivery methods of the invention, the lyophilized composition may be milled to obtain the finely divided dry powder consisting of particles within the desired size range described herein. Where spray-drying is used to obtain a dry powder form of the liquid pharmaceutical composition, the process is carried out under conditions that result in a substantially amorphous finely divided dry powder consisting of particles within the desired size range noted above. Similarly, if the starting pharmaceutical composition is already in a lyophilized form, the composition can be milled to obtain the dry powder form for subsequent preparation as an aerosol or other preparation suitable for pulmonary inhalation. Where the starting pharmaceutical composition is in its spray-dried form, the composition has preferably been prepared such that it is already in a dry powder form having the appropriate particle size for dispensing as an aqueous or non-aqueous solution or suspension in accordance with the pulmonary administration methods of the invention. For methods of preparing dry powder forms of pharmaceutical compositions, see, for example, International Patent Application Publications WO 96/32149, WO 97/41833 and WO 98/29096, and U.S. Pat. Nos. 5,976,574, 5,985,248, and 6,001,336, herein incorporated by reference.

The resulting dry powder form of the composition is then optionally placed within an appropriate delivery device for subsequent preparation as an aerosol or other suitable preparation that is delivered to the subject via pulmonary inhalation.

Where the dry powder form of the pharmaceutical composition is to be prepared and dispensed as an aqueous or non-aqueous solution or suspension, a metered-dose inhaler, or other appropriate delivery device is optionally used.

The dry powder form of the pharmaceutical composition according to some embodiments of the invention may optionally be reconstituted to an aqueous solution for subsequent delivery as an aqueous solution aerosol using a nebulizer, a metered dose inhaler, or other suitable delivery device. In the case of a nebulizer, the aqueous solution held within a fluid reservoir is converted into an aqueous spray, only a small portion of which leaves the nebulizer for delivery to the subject at any given time.

The remaining spray drains back into a fluid reservoir within the nebulizer, where it is aerosolized again into an aqueous spray. This process is repeated until the fluid reservoir is completely dispensed or until administration of the aerosolized spray is terminated. Examples of nebulizers are described herein.

The stabilized lyophilized or spray-dried compositions may be formulated using a buffering agent, which maintains the pH of the pharmaceutical composition within an acceptable range when in a liquid phase, such as during the formulation process or following reconstitution of the dried form of the composition. In some embodiments the pH is in the range of about pH 4.0 to about pH 8.5, about pH 4.5 to about pH 7.5, about pH 5.0 to about pH 6.5, about pH 5.6 to about pH 6.3, and about pH 5.7 to about pH 6.2. Suitable pH's include about 4.0, about 4.5, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.2, about 8.4, about 8.6, about 8.8, about 9.0, in the range of 3.5-9.0, 4.0-8.0, 4.5-7.5, 5.0-6.0, 5.0-7.5, 5.5-7.0 and 6.0-7.0.

In one particular embodiment, the pH is about 7.0 to 8.2. Suitable buffering agents include, but are not limited to, citrate buffer, phosphate buffer, succinate buffer, more particularly a sodium citrate/citric acid. Alternatively imidazole or histidine or other base/acid that maintains pH in the range of about pH 4.0 to about 8.5 can be used. Buffers are chosen such that they are compatible with the drying process and do not affect the quality, purity, potency, and stability of the protein during processing and upon storage.

The pharmaceutical compositions of the invention may optionally include a "therapeutically effective amount" or a "prophylactically effective amount" of a modified DNase I protein according to any of the respective embodiments described herein. A "therapeutically effective amount" refers to an amount effective, at dosages and for periods of time necessary, to achieve the desired therapeutic result. A therapeutically effective amount of the modified DNase I may vary according to factors such as the disease state, age, sex, and weight of the individual, and the ability of the modified DNase I to elicit a desired response in the individual. A therapeutically effective amount is also one in which any toxic or detrimental effects of the modified DNase I are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

In some embodiments of any of the embodiments described herein, the pharmaceutical composition of the invention comprises a unit dose of about 0.01 mg to 10 mg of modified DNase I. Alternatively, the pharmaceutical composition of the invention comprises a unit dose of about 0.1 mg to 5 mg; about 1 mg to 5 mg (e.g., about 1.25 mg, about 2.5 mg, about 5 mg); about 2.5 mg to 5 mg, about 2.0 to 4.5 mg, about 2.2 to 4.0 mg, about 2.0 to 3.0 mg, about 2.2 to 3.0 mg, about 2.3 to 3.0 mg, about 2.4 to 2.8 mg, about 2.4 to 2.6 mg; or about 2.5 mg of the modified DNase I or enzymatically active portion thereof. In another embodiment, the pharmaceutical composition comprises a unit dose over 10 mg.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Pharmaceutical compositions typically must be sterile and stable under the conditions of manufacture and storage. The composition can be formulated as a solution, microemulsion, dispersion, liposome, or other ordered structure suitable to high drug concentration. Sterile inhalable solutions can be prepared by incorporating the active compound (e.g., modified DNase I according to any of the respective embodiments described herein) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. The proper fluidity of a solution can be maintained, for example, by the use of a coating such as lecithin, by the maintenance of the required particle size in the case of dispersion and by the use of surfactants. Prolonged action of inhalable compositions can be brought about by including in the composition an agent that delays absorption, for example, monostearate salts and gelatin.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more pharmaceutically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art, for example, the surfactants described hereinabove.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose; and/or pharmaceutically acceptable polymers such as polyvinyl pyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes.

Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use, as detailed hereinabove.

The pharmaceutical composition of some embodiments of the invention may also be formulated in rectal compositions such as suppositories or retention enemas, using, e.g., conventional suppository bases such as cocoa butter or other glycerides.

The pharmaceutical composition may optionally be administered in a local rather than systemic manner, for example, via injection of the pharmaceutical composition directly into a tissue region of a patient or other subject in need thereof.

Herein, the term "tissue" refers to part of an organism consisting of cells designed to perform a function or functions. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue.

For treatment and/or prevention of respiratory and/or pulmonary disorders, the modified DNase I and/or pharmaceutical composition of the invention can be administered directly into the airways by pulmonary administration, for example, as detailed herein.

Pharmaceutical compositions suitable for use in context of some embodiments of the invention include compositions wherein the active ingredients are contained in an amount effective to achieve the intended purpose. More specifically, a therapeutically effective amount means an amount of active ingredients (modified DNase I according to any of the respective embodiments described herein) effective to prevent, alleviate or ameliorate symptoms of a disorder (e.g., cystic fibrosis) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays, and in animal models. For example, a dose can be formulated in animal models and/or in sputum samples (e.g., according to procedures described herein) to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in humans.

The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually, for example, to provide levels of the active ingredient in cells, serum, mucus and/or sputum which are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed herein.

Uses of Modified DNase I:

In some embodiments, the modified DNase I and/or pharmaceutical composition according to any of the respective embodiments described herein is for use in reducing a viscosity of a biological fluid and/or secretion containing DNA.

According to an aspect of some embodiments of the invention, there is provided a method of reducing a viscosity of a biological fluid and/or secretion containing DNA, the method comprising contacting the fluid and/or secretion with the modified DNase I and/or pharmaceutical composition according to any of the respective embodiments described herein. In some embodiments, the method is effected ex vivo. In some embodiments, the method is effected in vivo, in a subject in need thereof.

According to an aspect of some embodiments of the invention, there is provided a use of the modified DNase I and/or pharmaceutical composition according to any of the respective embodiments described herein in the manufacture of a medicament for reducing a viscosity of a biological fluid and/or secretion containing DNA.

In some embodiments, the modified DNase I and/or pharmaceutical composition according to any of the respective embodiments described herein is for use in reducing a DNA content in a biological fluid and/or secretion containing DNA.

According to an aspect of some embodiments of the invention, there is provided a method of reducing a DNA content in a biological fluid and/or secretion containing DNA, the method comprising contacting the fluid and/or secretion with the modified DNase I and/or pharmaceutical composition according to any of the respective embodiments described herein. In some embodiments, the method is effected ex vivo. In some embodiments, the method is effected in vivo, in a subject in need thereof.

According to an aspect of some embodiments of the invention, there is provided a use of the modified DNase I and/or pharmaceutical composition according to any of the respective embodiments described herein in the manufacture of a medicament for reducing a DNA content in a biological fluid and/or secretion containing DNA.

In some embodiments of any of the embodiments described herein relating to reducing a viscosity of a fluid and/or secretion containing DNA, the fluid and/or secretion is selected from the group consisting of sputum, mucus and sperm. In some embodiments, the secretion is mucus. In some embodiments, the secretion is sputum.

Herein, the term "sputum" refers to mucus of the lower airways, and encompasses both mucus coughed up as well as mucus still in the lower airways (also referred to in the art as "phlegm").

In some embodiments of any of the embodiments described herein relating to reducing a viscosity of a fluid and/or secretion containing DNA, the reduction in viscosity is characterized by a reduction in the oscillatory stress which must be applied to the fluid and/or secretion (e.g., sputum) such that the viscous modulus surpasses the elastic modulus (e.g., indicating that liquid-like behavior surpasses solid-like behavior), for example, as determined using procedures described herein.

In some embodiments of any of the embodiments described herein relating to reducing a viscosity of, and/or thinning a fluid and/or secretion containing DNA, the fluid and/or secretion is associated with a disease or condition resulting in increased amounts of DNA in the fluid and/or secretion, as compared to the DNA content of similar fluid and/or secretion from a healthy individual.

Excess DNA accumulated in secretions, fluids or tissues has been associated with a number of pathological and disease-related conditions, not only in pulmonary conditions, but also in conditions such as sepsis, infertility and metastatic spread of cancer. The modified DNase I of the present invention, administered so as to reach the site of excess extracellular DNA, can effectively lyse such extracellular DNA and thereby reduce the severity of, alleviate the symptoms of, treat, prevent or cure such a condition. Thus, according to some embodiments of the present invention, the disease or condition is associated with excess extracellular DNA in a fluid, secretion or tissue of said subject, and administering the modified DNase I, optionally as part of a pharmaceutical composition described herein, results in lysis of the extracellular DNA.

In some embodiments of any of the embodiments described herein, the modified DNase I and/or pharmaceutical composition described herein is for effecting lysis of DNA in any composition, for example an aqueous or semi-aqueous composition.

According to an aspect of some embodiments of the invention, there is provided a method of effecting lysis of DNA in a composition comprising DNA, for example an aqueous or semi-aqueous composition, the method comprising contacting the composition with the modified DNase I and/or pharmaceutical composition according to any of the respective embodiments described herein. In some embodiments, the method is effected ex vivo. In some embodiments, the method is effected in vivo, in a subject in need thereof.

According to an aspect of some embodiments of the invention, there is provided a use of the modified DNase I and/or pharmaceutical composition according to any of the respective embodiments described herein in the manufacture of a medicament for effecting lysis of DNA in a biological fluid and/or secretion containing DNA.

In some embodiments of any of the embodiments described herein relating to lysis of DNA in a composition, the composition is a biological fluid and/or secretion containing DNA, optionally a mucosal secretion, such as but not limited to mucus, sputum, sperm, or other secretions, in which lysis of DNA, reduction of the DNA content, and/or subsequent reduction of rheological properties is desirable. Such increased rheological properties of secretions are optionally the result of viral or microbial growth and cytotoxic response of the host's cellular immunity.

In some embodiments of any of the embodiments described herein, the modified DNase I (e.g., modified human DNase I) is biologically active, having catalytic activity, enzyme kinetics and specific activity comparable or superior to that of mammalian cell-expressed recombinant human DNase I, and effective in reducing rheological properties of cystic fibrosis (CF) sputum.

It will be appreciated that modified DNase I can be used to effect lysis of DNA and/or reduce the DNA content of biological fluids other than secretions, for example, blood, plasma, lymph, cerebrospinal fluid and the like, or in the local environment of an internal organ or tissue of an organism, for example, animal and/or human subject. In some embodiments, administration of modified DNase I to the organism results in increased endonuclease activity in blood, for example, in circulating blood, or in a tissue of the organism.

In some embodiments, the modified DNase I and/or pharmaceutical composition according to any of the respective embodiments described herein is for use in treating a disease or condition treatable by DNase I activity in a subject in need thereof.

According to an aspect of some embodiments of the invention, there is provided a method of treating a disease or condition treatable by DNase I activity subject in need thereof, the method comprising administering to the subject a therapeutically effective amount of the modified DNase I and/or pharmaceutical composition according to any of the respective embodiments described herein.

According to an aspect of some embodiments of the invention, there is provided a use of the modified DNase I and/or pharmaceutical composition according to any of the respective embodiments described herein in the manufacture of a medicament for treating a disease or condition treatable by DNase I activity in a subject in need thereof.

As used herein, the phrase "subject in need thereof" refers to a subject diagnosed with or exhibiting one or more of the respective conditions described herein, a subject who has been diagnosed with or exhibited one or more such conditions in the past, or a subject who has been deemed at risk of developing one or more such conditions due to hereditary or environmental factors.

In some embodiments of any of the embodiments described herein relating to a disease or condition treatable by a DNase I activity, the disease or condition is treatable by reducing a viscosity of and/or thinning a biological fluid and/or secretion containing DNA (e.g., according to any of the respective embodiments described herein).

In some embodiments of any of the embodiments described herein relating to a disease or condition treatable by a DNase I activity, the disease or condition is associated with excess extracellular DNA in a fluid, secretion or tissue of a subject.

In some embodiments, the disease or condition is a mucus-related disease or condition.

In some embodiments of any of the embodiments described herein relating to a disease or condition treatable by a DNase I activity, the disease or condition is a respiratory disease or condition, for example, a respiratory disease or condition associated with excess extracellular DNA in a fluid, secretion or tissue of a respiratory tract of a subject. In some embodiments, the respiratory disease or condition is mucus-related.

In some embodiments of any of the embodiments described herein relating to a disease or condition treatable by a DNase I activity, the disease or condition is a pulmonary disease or condition, for example, a pulmonary disease or condition associated with excess extracellular DNA in a fluid, secretion or tissue of a lung of a subject. In some embodiments, the pulmonary disease or condition is mucus-related.

In some embodiments, a subject in need thereof has a respiratory and/or pulmonary condition characterized by clinically abnormal spirometry values. Examples of spirometry parameters which can indicate the need of a subject include, but are not restricted to forced expiration volumes (FEV1), forced vital capacity (FVC), forced expiratory flow (FEF25-75) and the like. In some embodiments, administration of the modified DNase I to the subject results in an improvement in one or more of the spirometric parameters.

Respiratory conditions or diseases which can be treated by administration of modified DNase I protein according to any of the respective embodiments described herein include, without limitation, acute or chronic bronchopulmonary disease, atelectasis (e.g., due to tracheal or bronchial impaction and complications of tracheostomy), bronchitis or tracheobronchitis (e.g., chronic bronchitis, asthmatic bronchitis), cystic fibrosis, pneumonia, allergic diseases (e.g., allergic asthma), non-allergic asthma, tuberculosis, bronchopulmonary fungal infections, systemic lupus erythematosus, Sjogren's syndrome, bronchiectasis (e.g., non-cystic fibrosis bronchiectasis), emphysema, acute and chronic sinusitis, and the common cold.

In some embodiments of any of the embodiments described herein relating to a disease or condition treatable by a DNase I activity, the disease or condition is a suppurative disease or condition. In some embodiments, the disease or condition is a suppurative lung disease. In some embodiments, the disease or condition is a chronic suppurative lung disease (CSLD), e.g., a disease or condition characterized by a chronic wet cough and progressive lung damage.

A CSLD treatable according to embodiments of the invention may optionally be cystic fibrosis or a non-cystic fibrosis CSLD. Examples of a non-cystic fibrosis CSLD include, without limitation, non-cystic fibrosis bronchiectasis, and chronic obstructive pulmonary disorder (COPD) (including chronic bronchitis and emphysema). In some embodiments, the disease or disorder is cystic fibrosis.

In some embodiments of any of the embodiments described herein relating to a disease or condition treatable by a DNase I activity, the disease or condition is an exacerbation episode of a disease described herein, for example, an exacerbation episode of cystic fibrosis and/or an exacerbation episode of COPD.

In some embodiments of any of the embodiments described herein relating to treatment of a pulmonary disease or condition according to any of the respective embodiments described herein, including, without limitation, cystic fibrosis, the treatment is effected by pulmonary administration of the modified DNase I, the effective dosage being in a range of 0.1 to 50 mg DNase I protein (as active ingredient) per dose, 0.1 to 50 mg modified DNase I protein (as active ingredient) per dose, 0.5 to 25 mg modified DNase I protein (as active ingredient) per dose, 1.0 to 20 mg (e.g., about 1.25 mg, about 2.5 mg, about 5 mg) modified DNase I protein (as active ingredient) per dose, 1.5 to 15 mg modified DNase I protein (as active ingredient) per dose, 2.0 to 10 mg modified DNase I protein (as active ingredient) per dose, 2.5 to 7.5 mg modified DNase I protein (as active ingredient) per dose, 2.75 to 5 mg modified DNase I protein (as active ingredient) per dose or from 2.0 to 3.0 mg modified DNase I protein (as active ingredient) per dose. In some embodiments the effective dose of modified DNase I is 2.0-3.0 mg modified DNase I protein (as active ingredient) per dose, 2.1-2.9 mg modified DNase I protein (as active ingredient) per dose, 2.2-2.8 mg modified DNase I protein (as active ingredient) per dose, 2.3-2.7 mg modified DNase I protein (as active ingredient) per dose or 2.4-2.6 mg modified DNase I protein (as active ingredient) per dose. In some embodiments the effective dosage of modified DNase I is administered once daily, once every 2 days, once every 2-5 days, once every 2-10 days or more. In some embodiments the effective dosage of modified DNase I is administered 2, 3, from 2-4, from 2-6, from 2-8 or more times per day. In some embodiments of the invention, 2.5 mg of modified DNase I is administered via pulmonary administration once daily, e.g., for treatment of cystic fibrosis.

In some embodiments of any of the embodiments described herein relating to treatment of a pulmonary disease or condition according to any of the respective embodiments described herein, including, without limitation, cystic fibrosis, the treatment is effected by pulmonary administration of the modified DNase I, the effective dosage being in a range of 0.1 to 50 mg modified DNase I protein (as active ingredient) per day, 0.1 to 50 mg modified DNase I protein (as active ingredient) per day, 0.5 to 25 mg modified DNase I protein (as active ingredient) per day, 1.0 to 20 mg (e.g., about 1.25 mg, about 2.5 mg, about 5 mg) modified DNase I protein (as active ingredient) per day, 1.5 to 15 mg modified DNase I protein (as active ingredient) per day, 2.0 to 10 mg modified DNase I protein (as active ingredient) per day, 2.5 to 7.5 mg modified DNase I protein (as active ingredient) per day, 2.75 to 5 mg modified DNase I protein (as active ingredient) per day or from 2.0 to 3.0 mg (e.g., about 2.5 mg) modified DNase I protein (as active ingredient) per day.

In some embodiments of any of the embodiments described herein relating to a disease or condition treatable by a DNase I activity, the disease or condition is selected from the group consisting of lupus erythematosus (including systemic lupus erythematosus in general and DNase I-related susceptibility to systemic lupus erythematosus in particular), lupus nephritis, Cockayne syndrome, Angelman syndrome, male infertility, metastatic cancer, a viral, bacterial, fungal or protozoan infection sepsis, myocardial infarction, atherosclerosis, diabetes, delayed type hypersensitivity and a uterine disorder.

In some embodiments of any of the embodiments described herein relating to a treatment, the subject to be treated is afflicted by a *Pseudomonas* (e.g., *Pseudomonas aeruginosa*) lung infections, optionally in addition to a pulmonary disease or condition described herein, such as cystic fibrosis.

In some embodiments of any of the embodiments described herein relating to a treatment, the subject to be treated is non-responsive (e.g., as determined by a treating physician) to treatment with a non-modified DNase I, such as dornase alpha. In some embodiments, the non-modified DNase I (e.g., Pulmozyme® dornase alpha) is administered to the subject for at least four months, and a subject who does not exhibit clinically significant improvement following such a treatment is determined as being non-responsive.

In some embodiments of any of the embodiments described herein relating to a treatment, the subject to be treated is a child, i.e., below 18 years in age, optionally aged 12-17 years, and optionally below 12 years in age.

The modified DNase I and/or pharmaceutical composition according to any of the respective embodiments described herein can be used for treatment or prevention of male infertility (see, for example, U.S. Patent No. 20110033438 and U.S. Patent Application Publication No. 2007/0259367), and/or for the treatment or prevention of infectious disease caused by bacteria, virus, fungi and protozoa, treatment or prevention of sepsis (e.g. bacterial sepsis), treatment or prevention of tumors (both primary and metastatic), for prevention or reduction of metastatic growth, treatment and prevention of atherosclerosis, diabetes, delayed-type hypersensitivity reaction, treatment and prevention of diseases caused by somatic cell mutation and for enhancing longevity in an organism (see, for example, U.S. Patent Application Publication No. 2008/0004561). Treatment of male infertility by modified DNase I may be directed towards reducing the amount of DNA in semen samples, as taught, for example, by U.S. Patent Application Publication No. 2007/0259367, via ex vivo providing the semen samples with modified DNase I. In other embodiments, treatment of male infertility, tumors, metastatic transformation and growth, atherosclerosis, uterine and endometrial disorders, sepsis, viral, bacterial, fungal and protozoan infections, delayed type hypersensitivity reaction and diseases caused by somatic cell mutation is directed to reducing the amount of DNA in a subject, in vivo, and the DNase can be administered by any route or method suitable for delivery of the DNase to the desired target within the subject's body.

Techniques for effecting such treatments in vivo include, but are not limited to: oral administration, inhalation, intraperitoneal, intravenous, subcutaneous, intramuscular injection or any other form of systemic administration (see, for example, US20110033438 or US20080004561) of the modified DNase I and/or pharmaceutical composition according to any of the respective embodiments described herein.

In some embodiments of any of the embodiments described herein relating to treatment of a disease or condition according to any of the respective embodiments described herein, the effective dosage is in a range of 0.01 to 200 mg DNase I protein (as active ingredient) per dose, 0.1 to 100 mg modified DNase I protein (as active ingredient) per dose, 0.2 to 80 mg modified DNase I protein (as active ingredient) per dose, 0.2 to 60 mg modified DNase I protein (as active ingredient) per dose, 0.2 to 40 mg modified DNase I protein (as active ingredient) per dose, or 0.5 to 20 mg modified DNase I protein (as active ingredient) per dose. In some embodiments the effective dose of modified DNase I is 0.1 to 1 mg modified DNase I protein (as active ingredient) per dose, 1 to 10 mg modified DNase I protein (as active ingredient) per dose, or 10 to 200 mg modified DNase I protein (as active ingredient) per dose. In some of the aforementioned embodiments, the treatment is effected by systemic administration of the modified DNase I, optionally intraperitoneal, intravenous, subcutaneous, or intramuscular administration. In some embodiments, the disease or condition is lupus.

Any of the effective dosages described herein may optionally be a therapeutically effective amount according to any of the embodiments described herein relating to a therapeutically effective amount.

In some embodiments the effective dosage of modified DNase I is administered once daily, once every 2 days, once every 2-5 days, once every 2-10 days or more. In some embodiments the effective dosage of modified DNase I is administered 2, 3, from 2-4, from 2-6, from 2-8 or more times per day.

In some embodiments of any of the embodiments described herein relating to treatment of disease or condition according to any of the respective embodiments described herein, the effective dosage is in a range of 0.01 to 200 mg modified DNase I protein (as active ingredient) per day, 0.1 to 100 mg modified DNase I protein (as active ingredient) per day, 0.2 to 80 mg modified DNase I protein (as active ingredient) per day, 0.2 to 60 mg modified DNase I protein (as active ingredient) per day, 0.2 to 40 mg modified DNase I protein (as active ingredient) per day, or from 0.5 to 20 mg modified DNase I protein (as active ingredient) per day. In some embodiments the effective dose of modified DNase I is 0.1 to 1 mg modified DNase I protein (as active ingredient) per day, 1 to 10 mg modified DNase I protein (as active ingredient) per day, or 10 to 200 mg modified DNase I protein (as active ingredient) per day. In some of the aforementioned embodiments, the treatment is effected by systemic administration of the modified DNase I, optionally intraperitoneal, intravenous, subcutaneous, or intramuscular administration. In some embodiments, the disease or condition is lupus.

In some embodiments of any of the embodiments described herein relating to treatment of disease or condition according to any of the respective embodiments described herein, the effective dosage is in a range of about 0.01 mg to 10 mg per day of modified DNase I, optionally about 0.1 mg to 5 mg per day, optionally about 1 mg to 5 mg (e.g., about 1.25 mg, about 2.5 mg, about 5 mg) per day, optionally about 2.5 mg to 5 mg per day, optionally about 2.0 to 4.5 mg per day, optionally about 2.2 to 4.0 mg per day, optionally about 2.0 to 3.0 mg per day, optionally about 2.2 to 3.0 mg per day, optionally about 2.3 to 3.0 mg per day, optionally about 2.4 to 2.8 mg per day, optionally about 2.4 to 2.6 mg per day; or about 2.5 mg per day of the modified DNase I or enzymatically active portion thereof. In another embodiment, the effective dosage is over 10 mg per day.

In some embodiments of any of the embodiments described herein, a dosage (e.g., amount of DNase per administered dose, frequency of administrations, duration of treatment and/or total amount of DNase administered per treatment period) of modified DNase I according to embodiments of the invention is lower than a dosage according to an accepted treatment utilizing a non-modified DNase I, such as a dosage of Pulmozyme® DNase (e.g., an FDA-recognized dosage of Pulmozyme® DNase).

The modified DNase I and/or pharmaceutical composition according to any one of the respective embodiments described herein is optionally subjected to safety studies in human subjects, and/or clinical studies in human subjects afflicted by a condition described herein, preferably cystic fibrosis patients. The studies may be conducted in accordance with commonly used protocols or protocols otherwise recognized in the relevant art as being suitable. For example, the safety studies and/or clinical studies are optionally performed using protocols similar to, or essentially identical to protocols previously used to study a DNase I (e.g., dornase alfa).

In some embodiments of any of the embodiments described herein, the modified DNase I is administered in combination with an additional active agent (e.g., an additional active agent and/or ingredient according to any of the embodiments described herein, for example, an agent which reduces actin inhibition of DNase I activity (e.g., according to any one of the respective embodiments described herein), an antibiotic, a bronchodilators, an anti-inflammatory agent, a mucolytic (e.g. n-acetyl-cysteine), an actin binding or actin severing protein (e.g., gelsolin), a protease inhibitor, or a gene therapy product. Additional active agents can be administered prior to, along with, subsequent to or in any other temporal combination with the modified DNase I of embodiments of the invention.

In some embodiments of any of the embodiments described herein relating to a treatment, the treatment is optionally effected for at least one week. In some embodiments, the treatment is effected for at least two weeks. In some embodiments, the treatment is effected for at least four weeks. In some embodiments, the treatment is effected for at least two months. In some embodiments, the treatment is effected for at least six months. In some embodiments, the treatment is effected for at least one year months. In some exemplary embodiments, the treatment is effected for about four weeks. In some of any of the aforementioned embodiments the treatment comprises administration by inhalation (optionally once daily) of 1.25, 2.5 and/or 5.0 mg modified DNase.

Pulmonary Administration:

Pulmonary administration may be accomplished by suitable means known to those in the art. Pulmonary administration of modified DNase typically requires dispensing of the biologically active substance from a delivery device into the oral cavity of a subject during inhalation.

In some embodiments of any of the embodiments described herein relating to pulmonary administration, a pharmaceutical compositions comprising modified DNase I (according to any of the respective embodiments described herein) is administered via inhalation of an aerosol or other suitable preparation that is obtained from an aqueous or non-aqueous solution or suspension form, or a solid or dry powder form of the pharmaceutical composition, depending upon the delivery device used. Such delivery devices are well known in the art and include, but are not limited to, nebulizers, metered dose inhalers, and dry powder inhalers, or any other appropriate delivery mechanisms that allow for dispensing of a pharmaceutical composition as an aqueous or non-aqueous solution or suspension or as a solid or dry powder form.

Methods for delivering modified DNase I to a subject via pulmonary administration, including directed delivery to the central and/or peripheral lung region(s), include, but are not limited to, a dry powder inhaler (DPI), a metered dose inhaler (MDI) device, and a nebulizer.

In some embodiment of any of the embodiments described herein, the modified DNase I is delivered to a subject using a nebulizer or liquid inhaler. Generally, nebulizers use compressed air to deliver medicine as wet aerosol or mist for inhalation, and, therefore, require that the drug be soluble in water. Nebulizer devices can deliver relatively large doses in comparison to MDI (metered dose inhaler) or DPI (dry powder inhaler) devices, and are especially effective for delivery to the deep lung (peripheral lung region). No propellants are required for nebulizers, which includes jet nebulizers (air-jet nebulizers and liquid-jet nebulizers) and ultrasonic nebulizers. Examples of nebulizers include Akita™ (Activaero GmbH) (see, for example, U.S. Pat. No. 7,766,012 and European Patent No. EP1258264), a table top nebulizer inhalation system based on Pari's LC Star that provides full control over patient's breathing pattern and the portable Aeroneb® Go/Pro/Lab nebulizers (AeroGen). The Aeroneb® nebulizer is based on OnQ™ technology, i.e., an electronic micropump surrounded by a vibrational element and adaptable to the needs of a broad range of patients, including children and the elderly; single or multi-patient use.

The portable Aerocurrent™ (AerovertRx corp) may also be used in the methods and compositions of the invention (see International Patent Application Publication WO 2006/006963).

Staccato™ (Alexza Pharma) may also be used in the methods and compositions of the invention (see International Patent Application Publication WO03095012). The key to Staccato™ technology is vaporization of a drug without thermal degradation. AERx® (Aradigm), a hand held battery operated device, may also be used in the methods and compositions of the invention (see International Patent Application Publication WO 98/48873, U.S. Pat. Nos. 5,469,750, 5,509,404, 5,522,385, 5,694,919, 5,735,263, and 5,855,564). Another example of a nebulizer device which may also be used in the methods and compositions of the invention includes Respimat® (Boehringer), a multidose reservoir system. The DNase may also be delivered using the Collegium Nebulizer™ (Collegium Pharma). Another example of a nebulizer device which may also be used in the methods and compositions of the invention includes the Inspiration® 626 (Respironics), a compressor based nebulizer for home care delivering a particle size between 0.5 to 5 microns, Adaptive Aerosol Delivery® technology (Respironics), which delivers precise and reproducible inhaled drug doses.

Adaptive Aerosol Delivery (AAD)® systems incorporate electronics and sensors within the hand-piece to monitor the patient's breathing pattern by detecting pressure changes during inspiration and expiration, allowing the patient to take breaks in therapy without medication waste. Examples of AAD® system nebulizers include the HaloLite® AAD®, ProDose® AAD®, and I-Neb® AAD®. The HaloLite® Adaptive Aerosol Delivery (AAD)® (Respironics) is a pneumatic aerosolization system powered by a portable compressor. (see European Patent No. EP0910421, incorporated by reference herein).

The ProDose AAD® (Respironics) is a pneumatic aerosol system powered by a portable compressor, controlled by "ProDose Disc™" system. (Respironics). (see EP1245244). Promixin® can be delivered via Prodose AAD® for management of *Pseudomonas aeruginosa* lung infections, particularly in cystic fibrosis. Promixin® is supplied as a powder for nebulization that is reconstituted prior to use.

The I-neb AAD® is a handheld, miniaturized AAD® system without the need for a separate compressor ("I-Neb"), based upon a combination of electronic mesh-based aerosolization technology (Omron) and AAD® technology. I-neb AAD® has been used for delivery of Ventavis® (iloprost) (CoTherix/Schering AG).

Another example of a nebulizer which may be used in the methods and compositions of the invention is Aria™ (Chrysalis). Aria is based on a capillary aerosol generation system with MMAD ranging from 0.5-2.0 µm.

In another embodiment, the TouchSpray™ nebulizer (Odem), which uses a perforate membrane, which vibrates at ultrasonic frequencies, in contact with the reservoir fluid, to generate the aerosol cloud (see U.S. Pat. No. 6,659,364) may be used to deliver DNase in accordance with the invention. Additional nebulizers which may be used in the invention include nebulizers which are portable units which maximize aerosol output when the patient inhales and minimize aerosol output when the patient exhales using two one-way valves (see PARI nebulizers (PARI GmbH), which may be designed for specific patient populations, such a patients less than three years of age (PARI BABY™) and nebulizers for older patients (PARI LC PLUS® and PARI LC STAR®).

An additional nebulizer which may be used in the invention is the e-Flow® nebulizer (PARI GmbH) which uses vibrating membrane technology to aerosolize the drug solution, as well as the suspensions or colloidal dispersions (TouchSpray™; ODEM (United Kingdom)), as described in U.S. Pat. No. 6,962,151. Additional nebulizers which may be used in the invention include the Hudson T-Updraft I or II nebulizer (Pulmo-Aide compressor), Marquest Acorn I or II nebulizer (Pulmo-Aide compressor), Durable Sidestream (Portaneb compressor), the Microair® electronic nebulizer (Omron) (see U.S. Pat. No. 6,901,926) and a Mystic™ nebulizer (Ventaira) (see U.S. Pat. No. 6,397,838). The Mystic™ device is breath activated, and has been used with Corus 1030™ (lidocaine HCl), Resmycin® (doxorubicin hydrochloride), Acuair (fluticasone propionate), NCE with ViroPharm, and NCE with Pfizer. Thus, in one embodiment, the invention provides a container for use with a nebulizer device for pulmonary administration of DNase to a subject, the container comprising a propellant-free inhalable solution or suspension comprising the DNase.

The DNase may optionally be administered to a subject via inhalation in accordance with a dosing regimen designed to achieve a therapeutic effect. In some embodiments, a multiple dosing regimen may be used to treat disorders in which DNase I activity is beneficial using the methods described herein. Multiple variable dose methods of treatment can also be used to treat disorders in which DNase I activity is beneficial.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "preventing" refers to keeping a disease, disorder or condition from occurring in a subject who may be at risk for the disease, but has not yet been diagnosed as having the disease.

As used herein, the term "subject" includes mammals, preferably human beings at any age, which suffer from the pathology. Preferably, this term encompasses individuals who are at risk to develop the pathology.

As used herein the phrase "treatment regimen" refers to a treatment plan that specifies the type of treatment, dosage, schedule and/or duration of a treatment provided to a subject in need thereof (e.g., a subject diagnosed with a pathology). The selected treatment regimen can be an aggressive one which is expected to result in the best clinical outcome (e.g., complete cure of the pathology) or a more moderate one which may relief symptoms of the pathology yet results in incomplete cure of the pathology. It will be appreciated that in certain cases the more aggressive treatment regimen may be associated with some discomfort to the subject or adverse side effects (e.g., damage to healthy cells or tissue). The type of treatment can include a surgical intervention (e.g., removal of lesion, diseased cells, tissue, or organ), a cell replacement therapy, an administration of a therapeutic drug (e.g., receptor agonists, antagonists, hormones, chemotherapy agents) in a local or a systemic mode, an exposure to radiation therapy using an external source (e.g., external beam) and/or an internal source (e.g., brachytherapy) and/or any combination thereof. The dosage, schedule and duration of treatment can vary, depending on the severity of pathology and the selected type of treatment, and those of skills in the art are capable of adjusting the type of treatment with the dosage, schedule and duration of treatment.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Materials:

Actin (human non-muscle actin) was obtained from Cytoskeleton, Inc.

Ammonium chloride was obtained from Sigma.

ATP was obtained from Sigma.

Butylamine was obtained from Sigma.

$CaCl_2$ was obtained from Sigma.

CMC (N-cyclohexyl-N'-(2-morpholinoethyl)carbodiimide metho-p-toluenesulfonate) was obtained from Sigma and from Molekula.

Diisopropylcarbodiimide (DIC) was obtained from Sigma.

Di-t-butylcarbodiimide (DTC) was obtained from Sigma.

DMSO was obtained from Sigma.

DNA (from salmon testis) was obtained from Sigma.

EDC (1-ethyl-3-(3-dimethylaminopropyl)carbodiimide) was obtained from Sigma.

Ethanol was obtained from Sigma.

Ethanolamine was obtained from Sigma.

Ethylene diamine was obtained from Sigma.

Hexamethylene diamine was obtained from Sigma.

MES (2-(N-morpholino)ethanesulfonic acid) was obtained from Sigma.

Methyl green was obtained from Sigma.

Tris (tris(hydroxymethyl)aminomethane) was obtained from Sigma.

Plant Recombinant Human DNase I:

Plant recombinant human DNase I was prepared as described in International Patent Application Publication WO 2013/114374, by being expressed in *Nicotiana tabacum* Bright Yellow-2 (BY2) cell culture and harvested from the extracellular media. The DNase I generally contained a mixture of amino acid sequences, in which the majority had SEQ ID NO: 1, and a small fraction had SEQ ID NO: 2.

BY2 suspension culture was co-cultivated, for 48 hours, with the Agrobacterium tumefaciens EHA105 strain carrying the vector harboring the DNase I gene and the neomycin phosphotransferase (NPTII) selection gene.

Subsequently, the cells were kept in media supplemented with 50 mg/l of kanamycin and 250 mg/l cefotaxime. The NPTII gene confers resistance to kanamycin, thus only NPTII positive BY2 cells survive in this selection media. The cefotaxime was used to selectively kill the agrobacterium, the plant cells being resistant to this antibiotic. Once a nicely growing transgenic cell suspension was established, it was used for screening and isolating individual cell lines. To allow for the selection of individual cell lines, aliquots of highly diluted cell suspension were spread on solid BY2 medium. The cells were then grown until small calli developed. Each callus was then re-suspended in liquid culture. Media was then sampled and evaluated for DNase I levels. The lines that secreted relatively high DNase I levels were then further re-analyzed and compared for DNase I levels ending with the final selection of candidate DNase I expressing lines.

Media samples of transformed BY2 cells expressing the human DNase I protein were collected and when required, concentrated ×5 by centrifugal filters (Amicon Ultra, 10K, #UFC501096). DNase I catalytic activity in cell's media was determined by DNA-Methyl Green assay and compared to total DNase I amount, determined by Enzyme-linked immunosorbent assay.

Recombinant human DNase-I protein secreted from the tobacco suspension plant cells was purified by the following steps: at the end of the fermentation the intact tobacco cells were separated from the media by filtration using 100 mesh filter bags. The cells were discarded and the media containing the DNase I was collected for additional filtration with 0.2 μm filter sheets using filter-press apparatus. The DNase in the filtrated media was further purified by two steps of chromatography columns of an anion exchange resin (Poros 50HQ, Applied Biosystems, USA) followed by hydrophobic interaction chromatography of Phenyl 650C resin (Toyopearl, Japan). The purified DNase collected from the last column was 0.2 μm filtrated and stored at 4° C.

Cystic Fibrosis Sputum Collection, Storage and Sample Treatment:

Sputum samples were collected from patients with severe cystic fibrosis (CF) lung disease, who were treated at the Pulmonary and Cystic Fibrosis Unit of the Schneider Children's Medical Center of Israel or the Cystic Fibrosis Center of the Carmel Medical Center (Israel). Sputum was directly expectorated into a sterile, hermetically sealed container, and transported on ice to a facility for rheological characterization. Saliva was removed and each sputum sample was homogenized gently and divided into 200-300 mg aliquots, and stored at −70° C. until analyzed. Frozen samples were thawed at room temperature before analysis. Freezing of the sputum sample followed by a single thawing step has been shown to afford accurate and reproducible analysis of sputum rheology, similar to those of the fresh sample before freezing.

In order to ensure that the sputum is free of exogenous DNase I activity (e.g., Pulmozyme® DNase used for treatment), sputum samples were preferably collected 12-24 hours after the most recent treatment with Pulmozyme® DNase. It has been reported that inhaled aerosol DNase I is cleared from the sputum from patients in as soon as two hours.

Isoelectric Focusing

Isoelectric focusing (IEF) analysis was performed using an XCell SureLock Electrophoresis Cell equipped with a Powerpac power supply (BIO-RAD). Pre-cast Novex® polyacrylamide IEF gels with a pH range of 3-7 or 3-10, anode buffer, cathode buffer and sample buffer were obtained from Invitrogen. pI protein standards were obtained from SERVA. Electrophoresis conditions were as follows: 100 mV for 1 hour, 200 mV for 1 hour, 500 mV for 1.5 hour. Bands are visualized by Bio-Safe™ Coomassie Stain (Bio-Rad) according to the manufacturer's instructions.

SDS-PAGE:

DNase I and DNase variants were analyzed on SDS-PAGE. Detection of proteins was achieved by Coomassie brilliant blue staining (Bio-Rad) according to the manufacturer's instructions.

DNase Activity Assay:

Activity of DNase I and modified DNase I species was assessed by a methyl green enzymatic activity assay, employing DNA from salmon testis complexed with methyl green as a substrate. The dye methyl green intercalates between the stacked bases of double-stranded DNA. Once the long DNA molecules are hydrolyzed into tetranucleotides as a result of DNase I activity, dissociation of methyl green from the DNA occurs, the free methyl green decolorizing in a second, non-enzymatic reaction (likely to result from tautomerization of the dye). DNase I variants were purified by dialysis against a formulation buffer (150 mM NaCl, 1 mM CaCl$_2$, pH 6.1-6.5). Standard curves were prepared by dilution of purified standard (non-modified) plant-recombinant human DNase I in an activity buffer (25 mM HEPES-NaOH, 4 mM CaCl$_2$, 4 mM MgCl$_2$, 0.1% bovine serum albumin, 0.05% TWEEN-20, pH 7.5) at concentrations ranging from 0.3 to 20 ng/ml at 2-fold series dilutions. Samples and controls were prepared in a similar matter. One hundred microliters of standards, controls and samples was added in duplicates to a 96-well plate (NUNC) containing 100 µl of DNA-methyl green substrate and the contents were mixed thoroughly. The plates were then incubated overnight at 37° C. and absorbance was then measured at a wavelength of 620 nm. Absorbance was plotted versus standard concentrations and the data were fit to a 4-parameter logistic model by the nonlinear regression method of Marquardt.

DNase Kinetics Assay:

Kinetics of DNase I and modified DNase I species were determined using a DNA hyperchromicity assay, which measures an increase in the absorbance at 260 nm as DNA is degraded. The enzymatic reaction was carried out in 25 mM HEPES (4-(2-hydroxyethyl)-1-piperazineethanesulfonic acid) buffer, pH 7.5, containing 4 mM CaCl$_2$, 4 mM MgCl$_2$, 0.1% w/v bovine serum albumin (BSA), and 0.05% w/v TWEEN 20, at 30° C. for roughly 40 minutes.

In some experiments, 90 µl of salmon sperm DNA was added to a UV-STAR 96-well microplate (Greiner). After 5 minutes of pre-incubation at 30° C., 10 µl of diluted enzyme were added rapidly to each well, followed by collection of real-time optical density (OD) data (at 260 nm) at one minute intervals for 20 minutes at 30° C. The concentration of salmon sperm DNA was between 23.2 and 289 µg/ml. The final concentration of enzyme in each reaction mixture was 100 ng/ml.

In other experiments, pre-incubation of salmon sperm DNA at 30° C. was increased to 15 minutes, and real-time OD data (at 260 nm) was collected at 40 seconds intervals for 40 minutes at 30° C. The kinetics of non-modified DNase I was assayed using salmon sperm DNA at concentrations ranging from 10 to 240 µg/ml and a final concentration of enzyme in each reaction mixture of 14 ng/ml, while kinetics of EDA modified DNase I species was assayed using salmon sperm DNA at concentrations ranging from 1.6 to 38.8 µg/ml and a final concentration of enzyme in each reaction mixture of 2.5 ng/ml.

The following constants were determined:

Maximum velocity ($V_{max}$)—the velocity (V) indicated the rate of increase in absorbance (OD) per time unit (minute) that was catalyzed by an enzyme.

Michaelis constant ($K_M$)—the characteristic value of the enzyme which was defined by the substrate concentration required to achieve velocity of half of the maximum velocity ($V_{max}/2$). This value represents the dissociation constant (affinity for substrate) of the enzyme-substrate (ES) complex.

Specific activity ($k_{cat}$)—a measure of potency defined as the maximum velocity per ng protein.

Catalytic efficiency ($k_{cat}/K_M$)—ratio of the specific activity to the Michaelis constant.

Plots of initial velocity versus substrate concentration allow the extraction of $K_M$ and $V_{max}$ values using the Michaelis-Menten equation.

The specific activity is the $V_{max}$ per ng of protein ([E]) in the assay ($V_{max}$/ng DNase), and catalytic efficiency was calculated from obtained values for the Michaelis constant and specific activity.

Assay for DNase Inhibition by Actin:

Sputum from cystic fibrosis (CF) patients contains large quantities of DNA (3 to 14 mg/ml) and actin (0.06 to 5 mg/ml) released by necrosing neutrophils after their recruitment into the airways during response to infection. In addition to hydrolysis of DNA, DNase I can depolymerize filamentous actin (F-actin) into monomeric actin (G-actin). Monomeric globular actin (G-actin) is a potent inhibitor (Ki 1 nM) of DNase I enzymatic activity, potentially influencing the effectiveness of inhaled DNase I in lungs of CF patients.

To evaluate the inhibitory effect of G-actin on the activity of DNase I and modified DNase I species, an IC$_{50}$ assay (half maximal inhibitory concentration) was developed, utilizing the above methyl green enzymatic activity assay in the presence of elevated concentrations of human non-muscle actin.

10 µl of human non-muscle actin and 90 µl of 100 ng/ml DNase I were placed in a 96-well plate (NUNC) containing 100 µl of DNA-methyl green substrate, resulting in a final DNase I concentration of 45 ng/ml. Human non-muscle actin was diluted by 2-fold series dilutions in the above-mentioned methyl green assay activity buffer, which further contained 0.1 mM ATP (adenosine triphosphate), to concentrations ranging from 50 to 0.05 µg/ml. Each plate's content was then mixed thoroughly, plates were read at a wavelength of 620 nm, sealed and incubated for 4 hours at 37° C., and then read again at 620 nm. The change in absorbance ($\Delta OD_{620nm}$) was plotted versus actin concentration, and IC$_{50}$ parameters were calculated by a non-linear fit using GraFit software (Erithacus Software, UK).

In some experiments, the change in absorbance was also determined for control samples containing actin at concentrations as described hereinabove, but without DNase. The change in absorbance ($\Delta OD_{620}$) for control samples without DNase were then subtracted from the DNase-containing samples with the respective actin concentration, to remove background signal and thereby obtain a signal which reflects DNase activity and which was expressed as % DNase activity, by defining the DNase activity in the absence of actin as 100% DNase activity.

Assay for DNase Activity in Sputum:

Sputum aliquots were incubated for 30 minutes at a temperature of 37° C. with formulation buffer (150 mM NaCl, 1 mM CaCl$_2$, pH 6.1-6.5) containing either plant recombinant human DNase I (PRX-110), Pulmozyme® DNase or modified DNase I prepared as described herein, at the indicated final concentrations. Control samples were treated with DNase I formulation buffer alone. 4% (volume/weight) of DNase sample or control were added to the sputum sample. Following incubation, rheological properties of sputum samples were immediately measured, as described herein.

Sputum Rheology Measurement:

The physical behavior of mucus and sputum is complex (non-Newtonian), with highly variable properties that are between those of a viscous liquid and an elastic solid. Characterization of the physical properties of mucus largely focused on two properties: (i) viscous modulus, also termed shear loss modulus (G"), which reflects the extent to which the gel resists the tendency to flow, and (ii) elastic modulus, also termed shear storage modulus (G'), which reflects the tendency for the gel to recover its original shape following stress-induced deformation. The loss tangent (G"/G') and the phase angle (δ, equal to the inverse tangent of G"/G') reflect the overall elastic or viscous nature of the sample, wherein a loss tangent or phase angle close to zero indicates strongly elastic (solid-like) behavior, whereas a phase angle of 90° indicates purely viscous (liquid-like) behavior.

Rheological properties of sputum samples were determined using a HAAKE™ RheoStress™ 1 controlled stress rheometer (Thermo Fisher Scientific GmbH). Stress sweep measurements were performed at a temperature of 20° C. using 20 mm sandblasted parallel plate geometry with a gap width of 0.5 mm. Before measurements, sputum samples (200 µl) were loaded onto the rheometer plate and equilibrated for 30 seconds to allow relaxation to the original gel structure. In order to slow down the dehydration of the sputum, a solvent trap was used. A stress sweep was performed from 0.1 to 100 Pa at a constant frequency of 1 Hz, and the elastic modulus (G'), viscous modulus (G") and phase angle (δ) were measured. Rheological parameters were determined using HAAKE™ RheoWin™ 4 software (Thermo Fisher Scientific GmbH). The applied stress in which G" and G" cross over, i.e., the phase angle reaches 45°, is the stress in which the sample begins to act more liquid-like than solid-like. At this point stress values were recorded and compared between DNase I samples. In general, the degree of stress which must be applied to sputum in order to cross over from predominantly elastic, solid-like behavior to predominantly viscous, liquid-like behavior is indicative of how solid-like the sputum initially was. Reduction in the necessary degree of stress indicated disruption of elastic structure of the sputum. Experiments were performed on at least two sputum fractions taken from each sputum sample and the obtained data were averaged.

Measurements of Total DNA Content in Sputum:

Sputum DNA content was determined using a Quant-iT™ high sensitivity DNA assay kit (Invitrogen). Salmon sperm DNA and sputum samples (~50 mg) were diluted 10-fold in a dissolving buffer (25 mM HEPES-NaOH, 0.05% polysorbate (TWEEN 20), 5 mM EGTA, 1% sodium dodecyl sulfate, pH 7.5) and incubated at a temperature of 60° C. for 1 hour. Samples were repeatedly vortexed to allow sputum disintegration. DNA concentration of the diluted salmon sperm sample was then measured using a NanoDrop™ 2000 spectrophotometer (Thermo Fisher Scientific), and a standard curve was plotted by dilution of the salmon sperm sample in the dissolving buffer at concentrations ranging from 4.22 to 270 ng/ml, by 2-fold series dilutions. Similarly, sputum samples were further diluted from 300-fold to 8100-fold by 3-fold series dilution. Assay components were then equilibrated to room temperature, and a working solution was prepared by diluting Quant-iT™ dsDNA HS reagent 1:200 in Quant-iT™ dsDNA HS buffer. 5 µl of standards and samples were added in duplicate to a black 96-well plate (Greiner) and incubated with 100 µl of the working solution. Fluorescence was measured by a fluorometer for wavelengths of 502 nm excitation and 523 nm emission. Fluorescence units were plotted versus standard DNA concentrations and the data were fit to a 4-parameter logistic model by the nonlinear regression method of Marquardt. DNA concentration in sputum was then determined by interpolation.

Evaluation of DNA Fragmentation in Sputum:

DNase-mediated DNA fragmentation in sputum was evaluated using gel electrophoresis. Sputum samples (~50 mg) were diluted 10-fold in a dissolving buffer (25 mM HEPES-NaOH, 0.05% polysorbate (TWEEN 20), 5 mM EGTA, 1% SDS pH 7.5) and incubated at 60° C. for 1 hour. Samples were repeatedly vortexed to allow sputum disintegration. 20µ of each sample was then added to 6 µl of 6×DNA loading dye (Thermo Fisher Scientific) and separated on a 0.8% agarose gel using ethidium bromide to label the DNA and its relative quantity. Lambda DNA/HindIII ladder (Thermo Fisher Scientific) was used as size marker.

Size Exclusion Chromatography (SEC):

The amount of high molecular weight species (HMMS) of DNase I was quantified by native size exclusion chromatography using HPLC performed on a TSK GEL 2000 column using a buffer (pH 7.4) of 10 mM Tris, 100 mM NaCl, and 1 mM EDTA, for 50 minutes. Typical retention times were approximately 11 minutes for HMMS, 14 minutes for the dimer, and 16 minutes for the monomer.

Mass Spectrometry:

The average molecular weight of DNase I protein is measured using a matrix-assisted laser desorption ionization time-of-flight (MALDI-ToF) mass spectrometer, using sinapinic acid as a matrix. The equipment was calibrated using standards and about 2.5 micrograms of DNase I were used for mass analysis. MALDI is a soft ionization technique, allowing the analysis of biopolymers such as proteins, which tend to be fragile and fragment when ionized by more conventional ionization methods.

Modified and non-modified DNase I were analyzed similarly. Samples were mixed with a matrix, followed by spotting on a reusable MALDI plate. The ionization was triggered by a laser beam (normally a nitrogen laser), and m/z values of the singly positively charged monomer were determined using the linear mode method.

Example 1

DNase I with Diamine-Modified Carboxyl Groups

DNase I at a concentration of 1 mg/ml was reacted with a large excess (from 50 to 5,000 molar equivalents) of a diamine at a pH in a range of 5-6. Activation of DNase carboxyl groups was effected using 25-100 molar equivalents of a carbodiimide—EDC (1-ethyl-3-(3-dimethylaminopropyl)carbodiimide), di-isopropylcarbodiimide, or di-t-butylcarbodiimide).

Using the above general procedure, modified DNase was prepared (referred to herein as "Y24") using hexamethylene diamine (HMD) or ethylene diamine (EDA) as the diamine. 227 µl of a solution of DNase (2.2 mg/ml, 0.5 mg) in a formulation buffer with $CaCl_2$ (0.15 mg/ml) and NaCl (8.77 mg/ml) at a pH of 6 was mixed with a 0.1 M MES (2-(N-morpholino)ethanesulfonic acid) buffer having a pH of 5, followed by addition of 7,680 equivalents of EDA (75 µl of 1.7 M EDA) or 9,400 equivalents of HMD (230 µl of 0.7 M) in MES buffer (pH 5) and 25, 50 or 100 equivalents of EDC (52 mM in DMSO), to obtain a final DNase I concentration of 1 mg/ml. The following samples were thereby prepared:

Y24(1):

The DNase solution was added to 193 µl of MES buffer, and 75 µl of the EDA solution, and 25 equivalents of EDC (7 µl of the EDC in DMSO) were added.

Y24 (2):

The DNase solution was added to 185 µl of MES buffer, and 75 µl of the EDA solution, and 50 equivalents of EDC (15 µl of the EDC in DMSO) were added.

Y24(3):

The DNase solution was added to 170 µl of MES buffer, and 75 µl of the EDA solution, and 100 equivalents of EDC (30 µl of the EDC in DMSO) were added.

Y24(4):

The DNase solution was added to 38 µl of MES buffer, and 230 µl of the HMD solution, and 25 equivalents of EDC (7 µl of the EDC in DMSO) were added.

Y24(5):

The DNase solution was added to 30 µl of MES buffer, and 230 µl of the HMD solution, and 50 equivalents of EDC (15 µl of the EDC in DMSO) were added.

Y24(6):

The DNase solution was added to 15 µl of MES buffer, and 230 µl of the HMD solution, and 100 equivalents of EDC (30 µl of the EDC in DMSO) were added.

The reaction mixtures were shaken for 2 hours at room temperature. The reaction mixtures were then dialyzed into formulation buffer using a Vivaspin™ centrifugal concentrator (10,000 Da molecular weight cut-off).

Formation of an amide using a diamine results in replacement of negatively charged carboxyl group with a positively charged amine group (conjugated via an amide bond). Such modifications of electric charge were detected using isoelectric focusing (IEF) in a pH range of 3-10.

As shown in FIG. 1, amidation of DNase I by a diamine (EDA in lanes 1-3, HMD in lanes 4-6) was fully completed when 100 equivalents of EDC were used (lanes 3 and 6), but not when 25 equivalent (lanes 1 and 4) or 50 equivalents (lanes 2 and 5) of EDC were used, as determined by IEF analysis.

In order to assess the effect of DNase I modification by EDA and HMD on enzymatic activity, the DNase activity of modified DNase of samples Y24(2), Y24(3), Y24(5) and Y24(6) (described hereinabove) was evaluated using a methyl green assay as described in the Materials and Methods section hereinabove. The concentration of DNase was determined by the methyl green assay, using the tentative assumption that the DNase modification did not affect activity, and compared to the concentration of DNase as determined by measuring optical density.

As shown in FIG. 2, for most samples of diamine-modified DNase I, the DNase concentration determined by measuring DNase activity and the DNase concentration determined by measuring optical density were similar, thereby indicating that the modifications did not substantially affect activity of the DNase.

The effect of actin on enzymatic activity of the diamine-modified DNase I of samples Y24(2), Y24(3) and Y24(6) (described hereinabove) was then determined, using procedures described in the Materials and Methods section hereinabove. The diamine-modified DNase I was considerably less susceptible to inhibition by actin, in comparison with non-modified DNase I. The $IC_{50}$ for inhibition of non-modified DNase I by actin was about 0.75 µg/ml (0.777±0.025 µg/ml), whereas no $IC_{50}$ value could be measured for either EDA-modified or HMD-modified DNase I, as inhibition was less than 80% even at the highest actin concentration tested (100 µg/ml) and no sigmoidal pattern or plateau behavior was observable in the obtained data.

These results indicate that modified DNase I formed by amidation of DNase carboxyl groups with a diamine exhibits considerable resistance to actin, without any substantial loss of enzymatic activity.

Example 2

DNase I with Alkylamine-Modified Carboxyl Groups

In order to determine the effect of amidation with a simple alkyl monoamine on DNase I activity, DNase I was modified using butylamine and EDC.

Formation of an amide using butylamine results, in a concentration-dependent manner, in replacement of negatively charged carboxyl group with a non-charged amide group, as confirmed using isoelectric focusing (data not shown).

In addition, the modification by butylamine had relatively little effect on the activity of the DNase I, as determined using a methyl green assay and optical density measurements as described in Example 1 (data not shown).

Example 3

DNase I with Ethanolamine-Modified Carboxyl Groups

In order to evaluate the effect of amidation with a hydrophilic monoamine on DNase I activity, DNase I was modified using ethanolamine and EDC.

1 ml of a solution of DNase I (4.9 mg/ml, 4.9 mg) was mixed with 3.3 ml of a 0.1 M MES (2-(N-morpholino) ethanesulfonic acid) buffer having a pH of 5, followed by addition of 100 molar equivalents of EDC (550 µl of 28 mM EDC in DMSO). The reaction mixture was shaken at room temperature for 1 hour, and 200 µl of the reaction mixture was then removed for use as a control sample. To the remaining reaction mixture, 1,000 molar equivalents of ethanolamine (9.2 µl) were then added.

The pH of the reaction mixture was raised to 7.9, and the reaction mixture was then agitated for an additional 3 hours at room temperature. 100 µl of the reaction mixture was removed for use as an additional control sample, and the remaining reaction mixture was then dialyzed into DNase formulation buffer (0.15 M NaCl, 1 mM $CaCl_2$) using a Vivaspin™ centrifugal concentrator (3,000 Da molecular weight cut-off). The obtained ethanolamine-modified DNase is referred to herein as "L172".

Formation of an amide using ethanolamine results in replacement of negatively charged carboxyl group with a non-charged amide group.

As shown in FIG. 3, amidation of DNase I by ethanolamine was confirmed using isoelectric focusing (in a pH range of 3-10).

In order to assess the effect of DNase I modification by ethanolamine on enzymatic activity, the DNase activity of the ethanolamine-modified DNase samples was evaluated using a methyl green assay and optical density measurements as described in Example 1.

As shown in FIG. 4, the concentration of ethanolamine-modified DNase I as determined by measuring DNase activity was similar to the DNase I concentration as by measuring optical density, thereby indicating that the modification by ethanolamine had little or no effect on the activity of the DNase.

The effect of actin on enzymatic activity of the ethanolamine-modified DNase I was then determined, using procedures described in the Materials and Methods section hereinabove.

As shown in FIG. 5, the ethanolamine-modified DNase I was considerably less susceptible to inhibition by actin, in comparison with non-modified DNase I. The $IC_{50}$ for inhibition of non-modified DNase I by actin was approximately 0.75 µg/ml, whereas no $IC_{50}$ value could be measured for ethanolamine-modified DNase I, as inhibition was no more than about 20% even at the highest actin concentration tested (50 µg/m1).

The effect of DNase on the rheology of sputum samples from CF patients upon incubation for 30 minutes was determined according to procedures described in the Materials and Methods section hereinabove.

As shown in FIGS. 6 and 7, ethanolamine-modified DNase I (at a concentration of 0.05 or 0.2 μg/ml) was considerably more effective than non-modified DNase I (PRX-110, FIGS. 6 and 7) and Pulmozyme® DNase (FIG. 7) at reducing the viscosity of sputum from CF patients.

These results indicate that amidation with a monoamine such as ethanolamine considerably enhances the ability of DNase I to degrade DNA in the presence of actin and reduce the viscosity of sputum.

Example 4

DNase I with Ammonia or Tris Monoamine-Modified Carboxyl Groups

In order to further evaluate the effect of amidation with a hydrophilic monoamine on DNase I activity, DNase I was modified using ammonia or Tris (tris(hydroxymethyl)aminomethane), and EDC.

1 ml of a solution of DNase I (4.9 mg/ml, 4.9 mg) was mixed with 3.2 ml of a buffer of 0.1 M of a monoamine, buffer having a pH of 5, followed by addition of 100 molar equivalents of EDC (800 μl of 20 mM EDC in DMSO). The reaction mixture was shaken at room temperature for 1 hour, and 250 μl of the reaction mixture was then removed for use as a control sample. The pH of the remaining reaction mixture was raised to about 8, and the reaction mixture was then agitated for an additional 3 hours at room temperature. 100 μl of the reaction mixture was removed for use as an additional control sample, and the remaining reaction mixture was then dialyzed into DNase formulation buffer (0.15 M NaCl, 1 mM $CaCl_2$) using a Vivaspin™ centrifugal concentrator (3,000 Da molecular weight cut-off).

Using the above general procedures, Tris-modified DNase (referred to herein as "L171(1)") was prepared using a Tris buffer, and ammonia-modified DNase (referred to herein as "L171(2)") was prepared using an ammonium chloride buffer.

Formation of an amide using Tris or ammonia results in replacement of negatively charged carboxyl group with a non-charged amide group.

As shown in FIG. 8, amidation of DNase I by both Tris and ammonia ethanolamine was confirmed using isoelectric focusing (in a pH range of 3-10).

As further shown therein, amidation was more extensive in the control group in which the pH was not adjusted from about 5 to about 8 after 1 hour, thereby indicating that amidation of additional carboxylate groups on the DNase continued to occur at pH 5.

In order to assess the effect of DNase I modification by Tris or ammonia on enzymatic activity, the DNase activity of the modified DNase samples was evaluated using a methyl green assay and optical density measurements as described in Example 1.

As shown in FIG. 9, the concentration of ethanolamine-modified DNase I as determined by measuring DNase activity was similar to the DNase I concentration as by measuring optical density, thereby indicating that the modification by Tris or ammonia had little or no effect on the activity of the DNase.

The effect of actin on enzymatic activity of the modified DNase I was then determined, using procedures described in the Materials and Methods section hereinabove.

As shown in FIG. 10, the Tris-modified DNase I and the ammonia-modified DNase I were each considerably less susceptible to inhibition by actin, in comparison with non-modified DNase I. The $IC_{50}$ for inhibition of non-modified DNase I by actin was approximately 0.75 μg/ml, whereas no $IC_{50}$ value could be measured for either the Tris-modified DNase I or the ammonia-modified DNase I ethanolamine-modified DNase I, as inhibition was less than about 20% even at the highest actin concentration tested (50 μg/ml).

These results indicate that amidation with any of various monoamines considerably enhances the ability of DNase I to degrade DNA in the presence of actin.

The kinetics of the DNase activity of the actin inhibition resistant DNase I (referred to herein as "AIR DNase") obtained by modification with Tris was further analyzed in comparison to non-modified plant-recombinant human DNase I, by measuring the rate of DNA hydrolysis (as determined according to hyperchromicity) at different concentrations of DNA between 23.2 and 289 μg/ml, as described in the Materials and Methods section.

As shown in FIG. 11, the Tris (monoamine)-modified AIR DNase exhibited similar kinetics as non-modified DNase I. The $K_M$ of the Tris-modified AIR DNase was 53.1±8.2 μg/ml, whereas the $K_M$ of the non-modified DNase I was 82.0±6.1 μg/ml. The $V_{max}$ of the AIR DNase was 0.0249±0.0012 optical density units per minute, whereas the $V_{max}$ of the non-modified DNase was 0.0296±0.0008 optical density units per minute.

These results indicate that the kinetic properties (e.g., $V_{max}$, $K_M$) of AIR DNase are not substantially affected by the modification of DNase I by Tris.

The procedures described hereinabove for L171(1) were modified slightly in various manners in order to investigate factors which affect the modification of DNase I. Preliminary results indicate that termination of the reaction by removing reactants (e.g., by buffer exchange) results in less aggregation than termination by increasing the pH; that pH 5 is a suitable pH for performing the reaction; that the reaction is essentially complete after 2 hours; that DMSO and MES buffer are suitable solvents for the EDC; that room temperature is a suitable temperature for performing the reaction; that reaction with Tris can be performed in MES buffer; and that the presence of calcium slightly inhibits the amidation reaction, but reduces dimerization.

Example 5

Effect of Actin Inhibition Resistant Modified DNase I on Sputum

Sputum samples were incubated with actin inhibition resistant DNase I (AIR DNase), prepared as described in Example 4 for L171(1), and sputum rheology, DNA content and DNA fragmentation were then evaluated, using procedures described in the Materials and Methods section hereinabove. The results were compared to the sputum rheology, DNA content and DNA fragmentation determined in untreated sputum and in sputum incubated with dornase alfa (Pulmozyme®) DNase I.

As shown in FIGS. 12A and 12B, 2 μg/gram sputum of AIR DNase eliminated almost all of the DNA in the sputum, and was considerably more effective than 2 and even 5 μg/gram sputum of dornase alfa DNase I at reducing DNA content of sputum.

As shown in FIG. 13, 2 μg/ml AIR DNase was considerably more effective than 2 and even 5 μg/gram sputum of dornase alfa DNase I at disrupting the elastic structure of sputum.

The effect of AIR DNase on DNA fragmentation and sputum rheological properties was then evaluated in additional sputum samples from various cystic fibrosis patients, as shown in FIGS. 14-16D. For six of the patients, the sample was sufficiently large to compare the effects of AIR DNase with both plant-recombinant human DNase I and dornase alfa DNase I, and the results from such samples are summarized in FIG. 17.

As shown in FIG. 14, 2 µg/gram sputum of AIR DNase was considerably more effective than 2 µg/gram sputum of plant-recombinant human DNase I at reducing the DNA content of sputum, in a large majority of sputum samples.

As shown in FIG. 15, 2 µg/ml of AIR DNase eliminated almost all of the DNA in sputum samples from 3 different patients, and was considerably more effective than dornase alfa DNase I at reducing the DNA content of sputum from each of the patients.

As shown in FIGS. 16A-16D, AIR DNase was generally considerably more effective at disrupting the elastic structure of sputum than the same concentration of dornase alfa DNase I, at concentrations of 20, 2, 0.2 and 0.05 µg/gram sputum.

Similarly, as shown in FIG. 17, AIR DNase was on average considerably more effective at disrupting the elastic structure of sputum than either plant recombinant human DNase I (PRX-110) or dornase alfa DNase I.

These results indicate that the resistance to actin inhibition of AIR DNase is associated with enhanced DNA fragmentation and enhanced disruption of sputum elastic structure.

Example 6

Effect of Different Carbodiimides on Modification of DNase I Carboxyl Groups

Carboxyl group modification of DNase I by Tris was performed as described hereinabove, except that DIC (diisopropylcarbodiimide), DTC (di-t-butylcarbodiimide) or CMC (N-cyclohexyl-N'-(2-morpholinoethyl)carbodiimide metho-p-toluenesulfonate) were used instead of EDC.

The final reaction mixtures contained 1 mg/ml DNase I, 25 or 50 molar equivalents of DIC or CMC, or 50 or 100 molar equivalents of DTC, 100 molar equivalents of Tris, and 100 mM MES as buffer (pH 5); and the reaction was continued for 2.5 hours at room temperature.

As shown in FIG. 18, the use of CMC resulted in a greater change in isoelectric point than did DTC and DIC upon modification of DNase I.

As shown in FIG. 19, the use of CMC also resulted in reduced amounts of species other than monomeric DNase I (low molecular weight species as well as high molecular weight species), in comparison with use of DIC, as determined by SDS-PAGE.

These results indicate that CMC is more effective than DIC and DTC at amidating DNase I carboxylic acids.

In addition, CMC from two suppliers (Sigma and Molekula) were used and the results were compared. No significant difference was observed when using CMC from different suppliers.

Example 7

Effect of Buffer on Modification of DNase I Carboxyl Groups

Carboxyl group modification of DNase I by Tris was performed as described in Example 6 using CMC (N-cyclohexyl-N'-(2-morpholinoethyl)carbodiimide metho-p-toluenesulfonate) and MES buffer at different MES concentrations, in order to assess the effect of the buffer concentration on the amidation reaction.

The final reaction mixtures contained 2 mg/ml DNase I, 75 molar equivalents of CMC, 100 molar equivalents of Tris, and 20, 60, 100 or 200 mM MES as buffer (pH 5); and the reaction was continued for 2.5 hours at room temperature.

The buffer concentration did not appear to have any significant effect on the obtained product, in the tested range of concentrations, as determined by isoelectric focusing, gel electrophoresis (SDS-PAGE), size exclusion chromatography, and assays of enzymatic activity (using methyl green) and actin inhibition.

These results indicate that low buffer concentrations, such as 20 and 15 mM MES buffer, are suitable for use in modification of DNase I.

In addition, carboxyl group modification of DNase I by Tris was performed using CMC as described hereinabove, at a pH of 4, 4.5, 5, 5.5 or 6, in order to assess the effect of pH on the amidation reaction.

The final reaction mixtures contained 1 mg/ml DNase I, 35 molar equivalents of CMC, 100 molar equivalents of Tris, and 100 mM MES as buffer at the indicated pH values; and the reaction was continued for 2.5 hours at room temperature.

As shown in FIG. 20, amidation at a pH in a range of 4.5-5.5 resulted in a greater change in isoelectric point than did amidation at a pH of 4 or 6.

As shown in FIG. 21, no amidation at any of the tested pH conditions resulted in a significant change in molecular weight of the DNase I, indicating that neither high molecular weight species (such as dimers, multimers or aggregates or low molecular weight species (such as breakdown products) were formed in substantial amounts.

These results indicate that a pH value above 4 but less than 6 is particularly effective for amidation reactions.

Example 8

Effect of Reaction Temperature on Modification of DNase I Carboxyl Groups

Carboxyl group modification of DNase I by ethylene diamine (EDA) was performed as described hereinabove using CMC (N-cyclohexyl-N'-(2-morpholinoethyl)carbodiimide metho-p-toluenesulfonate) at different reaction temperatures, in order to assess the effect of reaction temperature on the amidation reaction.

4 mg of DNase (5.4 mg/ml, 740 µl) was diluted with 300 µl MES buffer (100 mM, pH 5) and 300 µl water. 33.2 mg (2,000 equivalents) of ethylene diamine dihydrochloride in 600 µl water was added, and the reaction mixture was divided into 4 aliquots which were shaken at different temperatures.

The final reaction mixtures contained 2 mg/ml DNase I, 60 molar equivalents of CMC, 2,000 molar equivalents of EDA, 2 mM $CaCl_2$ and 15 mM MES as buffer (pH 5); and the reaction was continued for 2.5 hours at 12° C., 16° C., 20° C. or 25° C.

The reactions were terminated by purification on a mini-trap column; the protein was diluted with 150 mM NaCl and 1 mM $CaCl_2$.

As shown in FIG. 22, no non-modified DNase was observed after reaction at 20-25° C.

Example 9

Effect of Reaction Time on Modification of DNase I Carboxyl Groups

Carboxyl group modification of DNase I by ethylene diamine (EDA) was performed as described in Example 8, using different reaction times, in order to assess the effect of reaction time on the amidation reaction.

The final reaction mixtures contained 2 mg/ml DNase I, 60 molar equivalents of CMC, 2,000 molar equivalents of EDA, 2 mM $CaCl_2$, and 15 mM MES as buffer (pH 5); and the reaction was continued for 1, 1.5, 1.75, 2 or 2.5 hours at room temperature.

As shown in FIG. 23 the reaction was completed after about 2 hours, there being no significant difference in the isoelectric points of products obtained by reaction for 2 hours and for 2.5 hours.

Example 10

Effect of Amine Excess on Modification of DNase I Carboxyl Groups

Carboxyl group modification of DNase I by ethylene diamine (EDA) was performed as described in Example 8, using different concentrations of EDA, in order to assess the effect of the concentration of the amine reactant on the amidation reaction.

The final reaction mixtures contained 2 mg/ml DNase I, 75 molar equivalents of CMC, 100, 500, 1000, 2000, 4000 or 6,000 molar equivalents of EDA, and 15 mM MES as buffer (pH 5); and the reaction was continued for 2.5 hours at room temperature. The obtained modified DNase I was characterized by size exclusion chromatography and isoelectric focusing, according to procedures described herein.

As shown in Table 1 below and in FIG. 24, higher proportions of EDA resulted in lower levels of high molecular weight and dimer species, as determined by size exclusion chromatography. As further shown therein, the aforementioned effect of EDA proportions was strongest at relative EDA concentrations of 100 to 2,000 equivalents EDA, with no considerable difference appearing in the range of 2,000 to 6,000 EDA equivalents.

Similarly, as shown in FIG. 24, relative EDA concentrations of 500 equivalents or more of EDA resulted in a greater degree of amidation than did 100 equivalents of EDA, as determined by isoelectric focusing.

These results indicate that a use of more than 1,000 equivalents of EDA for modifying DNase I is advantageous in that proportions of dimers and high molecular weight species are reduced (and amidation efficiency is increased), but that a use of 4,000 equivalents of EDA is not particularly advantageous as it may require removal of larger amounts of EDA than required for a use of 2,000 equivalents EDA, without providing any considerable advantage in the nature of the modified DNase I.

TABLE 1

Amounts of modified DNase I monomer, dimer and high molecular weight species (HMW) upon reaction with 100-6,000 equivalents of ethylene diamine (EDA)

| | EDA equivalents | Relative Amounts % | | |
| --- | --- | --- | --- | --- |
| | | HMW | Dimer | Monomer |
| 1 | 100 | 0.37 | 1.44 | 98.19 |
| 2 | 500 | 0.14 | 0.76 | 99.1 |
| 3 | 1000 | 0.08 | 0.47 | 99.45 |
| 4 | 2000 | 0.05 | 0.33 | 99.62 |
| 5 | 4000 | 0.03 | 0.18 | 99.79 |
| 6 | 6000 | 0.07 | 0.1 | 99.83 |

Example 11

Effect of Carbodiimide and Calcium Concentration on Modification of DNase I Carboxyl Groups Carboxyl group modification of DNase I by ethylene diamine (EDA) was performed as described in Example 8, using different concentrations of CMC, in order to assess the effect of the concentration of carbodiimide reagent on the amidation reaction. The reaction was further performed in the presence or absence of 2 mM calcium ions, in order to assess the effect of calcium ions on the amidation reaction.

The final reaction mixtures contained 2 mg/ml DNase I, 35, 45, 55 or 65 molar equivalents of CMC, 2,000 molar equivalents of EDA, 0 or 2 mM calcium ions, and 15 mM MES as buffer (pH 5); and the reaction was continued for 2.5 hours at room temperature. The obtained modified DNase I was characterized by size exclusion chromatography and isoelectric focusing, according to procedures described herein.

As shown in FIG. 25, the amount of CMC used was correlated to the degree to which the isoelectric point of DNase I changed upon amidation, indicating that greater amounts of CMC resulted in amidation of more carboxylic acid sites on the DNase I.

This result suggests that relatively high amounts of CMC, such as 65 equivalents of CMC, advantageously enhance the degree of modification of DNase I and may thereby enhance a resistance to inhibition by actin.

As further shown in FIG. 26, the nature of the modified DNase I was not significantly affected by the presence or absence of calcium ions, as determined by isoelectric focusing.

This result suggests that 2 mM calcium may be included in amidation reactions in order to enhance protein stability, without having any significant undesirable effect.

Example 12

Exemplary Actin Inhibition Resistant DNase I Prepared by Modification with a Diamine Carboxyl group modification of DNase I by ethylene diamine (EDA) was performed as described in Example 8, using 60 molar equivalents of CMC and 2,000 molar equivalents of EDA, at a temperature in a range of 20-25° C.

The susceptibility of EDA-modified DNase I obtained by modification with EDA to inhibition by actin was compared to that of non-modified Pulmozyme® DNase I.

As shown in FIG. 26, the EDA-modified DNase I was considerably less susceptible to inhibition by actin, in comparison with Pulmozyme® DNase I. The $IC_{50}$ for inhibition of Pulmozyme® DNase I by actin was 0.23 μg/ml, and the activity of Pulmozyme® DNase I was completely abolished at actin concentrations above 10 μg/ml, whereas inhibition of EDA-modified DNase I was no more than about 13% even at the highest actin concentration tested (50 μg/ml), and less than 10% at actin concentrations of about 2 μg/ml or less. The ~30% baseline depicted in FIG. 26 for Pulmozyme® DNase I at high actin concentrations does not represent actual DNase activity and is a result of calculating activity from OD without subtraction of blank OD values.

Example 13

Effect of Carbodiimide Excess on Actin Resistance of Modified DNase I

Carboxyl group modification of DNase I by Tris was performed as described in Example 6, using different concentrations of DIC and EDC, in order to assess the effect of the concentration of carbodiimide reagent on the enzymatic properties of the obtained modified DNase I.

The final reaction mixtures contained 1 mg/ml DNase I, 25 or 50 molar equivalents of DIC or EDC, and 0.1 M Tris (pH 5); and the reaction was continued for 2.5 hours at room temperature. The obtained modified DNase I was characterized by isoelectric focusing and by assaying inhibition of DNase by actin, according to procedures described herein.

As shown in FIG. 27, the isoelectric point of DNase I changed to a greater degree upon amidation with 50 equivalents of carbodiimide (DIC or EDC) as compared to 25 equivalents of carbodiimide, indicating that greater amounts of carbodiimide resulted in amidation of more carboxylic acid sites on the DNase I, confirming the results obtained with CMC, described in Example 11. As further shown therein, the use of EDC resulted in a greater degree of amidation than did the use of a corresponding amount of DIC.

As shown in FIG. 28, the resistance of DNase I activity to inhibition by actin was greater upon amidation with 50 equivalents of carbodiimide (DIC or EDC) as compared to 25 equivalents of carbodiimide. As further shown therein, the use of EDC resulted in a greater degree of resistance to actin than did the use of a corresponding amount of DIC. As further shown therein, the $IC_{50}$ for actin inhibition of non-modified plant recombinant human DNase I was 0.46 μg/ml, whereas the $IC_{50}$ of each of the modified DNase I species could not be calculated because considerable activity remained even at the highest actin concentration tested (50 μg/ml).

These results indicate that the degree of actin resistance is correlated to the number of carboxylic acid sites in the DNase I which are modified by amidation, and that this is dependent upon the reaction conditions, including the amount and type of carbodiimide reagent used.

Carboxyl group modification of DNase I by Tris was further performed using the following reaction mixtures and conditions:

1) reaction mixture containing about 1 mg/ml DNase I, 100 molar equivalents of EDC, and 0.1 M Tris (pH 5); wherein the reaction was continued for 1 hour at room temperature;

2) final reaction mixture containing about 1 mg/ml DNase I, 25 molar equivalents of EDC (which was added drop-wise), 100 molar equivalents of Tris, and 100 mM MES buffer (pH 5); wherein the reaction was continued for 2.5 hours at room temperature, and ultra-filtrated using a solution of 1 mM $CaCl_2$ and 150 mM NaCl; and 3) final reaction mixture containing about 1 mg/ml DNase, 35 molar equivalents of CMC, 100 molar equivalents of Tris (which was added drop-wise), and 100 mM MES buffer (pH 5); wherein the reaction was continued for 2.5 hours at room temperature, and ultra-filtrated using a solution of 1 mM $CaCl_2$ and 150 mM NaCl.

The obtained modified DNase I was characterized by isoelectric focusing, by assaying inhibition of DNase by actin, and by determining effects of modified DNase I on sputum rheology, according to procedures described herein.

As shown in FIGS. 29-31C, the degree of amidation in each modified DNase I sample as indicated by increase in the isoelectric point (FIG. 29) was correlated to the degree of resistance to inhibition by actin (FIG. 30) and to the degree of disruption of the elastic structure of sputum samples (FIGS. 31A-31C), with the abovementioned DNase I modified with 100 molar equivalents of EDC and 0.1 M Tris exhibiting the greatest degree of amidation, resistance to actin and disruption of sputum structure.

As further shown in FIG. 30, the $IC_{50}$ for actin inhibition of non-modified plant recombinant human DNase I was 0.89 μg/ml, whereas the $IC_{50}$ of each of the modified DNase I species could not be calculated because considerable activity remained even at the highest actin concentration tested (50 μg/ml).

Carboxyl group modification of DNase I by Tris was further performed using Pulmozyme® DNase I instead of plant recombinant human DNase I.

The final reaction mixture contained 1 mg/ml DNase I, 25 molar equivalents of EDC, 100 molar equivalents of Tris, and 100 mM MES as buffer (pH 5). The reaction was continued for 2.5 hours at room temperature, and ultra-filtrated using a solution of 1 mM $CaCl_2$ and 150 mM NaCl. The obtained modified DNase I was characterized by isoelectric focusing and by assaying inhibition of DNase by actin, according to procedures described herein.

As shown in FIG. 32, the isoelectric point of the Pulmozyme® DNase I increased upon reaction with Tris and EDC, indicating that amidation of the mammalian recombinant DNase I occurred.

As shown in FIG. 33, the $IC_{50}$ for actin inhibition of Pulmozyme® DNase I was 0.19 μg/ml, whereas the $IC_{50}$ of the modified Pulmozyme® DNase I could not be calculated because considerable activity remained even at the highest actin concentration tested (50 μg/ml).

The above results confirm that modification of DNase I from various sources by amidation described herein results in actin inhibition resistant (AIR) DNase, and that the degree of resistance is correlated to the degree of amidation of the DNase I.

Example 14

Larger Scale Preparation of Actin Inhibition Resistant Modified DNase I (AIR DNase)

Actin inhibition resistant modified DNase I (AIR DNase) was prepared on a larger scale (10-40 grams protein), based on the procedures described hereinabove for modifying DNase using ethylene diamine (EDA). Plant recombinant human DNase I was added to the reaction solution. The coupling agent CMC (N-cyclohexyl-N'-(2-morpholinoethyl) carbodiimide metho-p-toluenesulfonate) was dissolved in water and added to a reaction solution comprising plant recombinant human DNase I and ethylene diamine (EDA).

The reaction was performed using an excess of EDA (at a molar ratio of 2000:1 EDA:DNase I) and an excess of CMC (at a molar ratio of 60:1 CMC:DNase I), and was performed at a temperature in a range of 20-25° C. for 2 hours. The properties of the obtained AIR DNase were compared with those of non-modified plant recombinant human DNase I and/or Pulmozyme® DNase I, using techniques described hereinabove.

As shown in FIG. 34, Pulmozyme® DNase I was more negatively charged than the AIR DNase I and non-modified plant recombinant human DNase I, as determined by isoelectric focusing. This result indicates a presence of characteristic mammalian negatively charged glycans, such as sialic acid and mannose-6-phosphate, in mammalian recombinant Pulmozyme® DNase I. In addition, AIR DNase I was less negatively charged than non-modified plant recombinant human DNase I, due to the modification of the protein, which decreases the number of negatively charged groups and introduced positively charged groups.

As further shown in FIG. 34, Pulmozyme® DNase I exhibits a more heterogeneous isoelectric pH than does non-modified plant recombinant human DNase I.

This result indicates that Pulmozyme® DNase I comprises species with different glycosylation patterns on the protein, characterized by different amounts of charged saccharides (e.g., negatively charged sialic acids and mannose-6-phosphate), whereas of plant recombinant human DNase does not exhibit such differences in glycosylation pattern, which is consistent with the presence in plant recombinant human DNase of non-ionic glycans, as is characteristic of plant glycosylation.

As shown in FIGS. 35 and 36, the molecular weight of non-modified plant recombinant human DNase I was approximately 32,200 Da (FIG. 35), whereas the molecular weight of AIR DNase was approximately 32,700 Da (FIG. 36), as determined by MALDI-ToF mass spectroscopy. These results indicate that the modification of the DNase I increased the molecular weight, indicating that EDA molecules were conjugated to the protein.

The theoretically predicted molecular weight of the non-modified plant recombinant human DNase I, based on a 261 amino acids sequence (without glycosylation), is 29,311 Da. Thus, the above results further indicate that that the molecular weight of the glycans was about 2,900 Da.

The resistance of AIR DNase obtained by modification with EDA to inhibition by actin was confirmed and compared to the activity of non-modified plant recombinant human DNase I and Pulmozyme® DNase I in the presence of actin.

As shown in FIG. 37, the AIR DNase exhibited resistance to inhibition by actin even at the highest actin concentration tested (50 μg/ml), whereas plant recombinant human DNase I as inhibited by actin with an $IC_{50}$ of 0.47 μg/ml, and Pulmozyme® DNase I was inhibited by actin with an $IC_{50}$ of 0.2 μg/ml.

In order to evaluate the potency and enzyme kinetics of AIR DNase obtained by modification with EDA, the maximum velocity ($V_{max}$), Michaelis constant ($K_M$) and specific activity of AIR DNase ($k_{cat}$), non-modified plant recombinant human DNase I and Pulmozyme® DNase I were determined according to procedures described in the Materials and Methods section, using DNA concentrations ranging from 1.5 to 240 μg/ml.

As shown in FIGS. 38A and 38B and in Table 2 below, plant recombinant human DNase I exhibits greater DNase activity than Pulmozyme® DNase I, both in terms of a greater specific activity ($k_{cat}$), indicating greater enzymatic potency, and in terms of a lower Michaelis constant ($K_M$), indicating greater affinity to DNA.

Without being bound by any particular theory, it is believed that the lower Michaelis constant of plant recombinant human DNase I is associated with the weaker negative charge than that of mammalian recombinant DNase I (e.g., as shown in FIG. 34), which allows for greater affinity with negatively charged DNA.

As further shown in FIGS. 38A and 38B and in Table 2, the specific activity ($k_{cat}$) of EDA-modified AIR DNase was similar to that of non-modified plant recombinant human DNase I, indicating that modification of the DNase I with EDA did not substantially affect specific activity, whereas the Michaelis constant of AIR DNase was almost 7-fold lower than that of non-modified plant recombinant human DNase I (and that of Pulmozyme® DNase I), and the ratio $k_{cat}/K_M$ of AIR DNase was almost 7-fold greater than that of non-modified plant recombinant human DNase I (and that of Pulmozyme® DNase I). This result indicates that the modification of DNase I with a diamine greatly enhanced the catalytic efficiency of the DNase I and the affinity of the DNase I to DNA, which enhances enzymatic activity considerably at relatively low DNA concentrations.

TABLE 2

Specific activity ($k_{cat}$), Michaelis constant ($K_m$) and catalytic efficiency ($k_{cat}/K_M$) of AIR DNase and non-modified plant recombinant human DNase I and Pulmozyme ® DNase I

| | $k_{cat}$ (milli-OD units per minute per ng DNase) | $K_m$ (μg/ml) | $k_{cat}/K_m$ (same units for $k_{cat}$ and $K_m$ as on left) |
|---|---|---|---|
| AIR DNase (plant recombinant human DNase I modified with EDA) | 1.8 | 4.0 | 0.45 |
| Plant recombinant human DNase I | 1.9 | 27.2 | 0.070 |
| Pulmozyme ® DNase I | 1.4 | 56.8 | 0.025 |

The effect of the EDA-modified AIR DNase on sputum rheology, DNA content and DNA fragmentation in sputum samples from cystic fibrosis patients was determined using the procedures described hereinabove.

FIGS. 39A-39C and 40A-40C show the efficacy of AIR DNase at disrupting the elastic structure of sputum (FIGS. 39A and 40A), and reducing DNA content (FIGS. 39B and 40B) and fragmenting DNA (FIGS. 39C and 40C) of sputum from each of two exemplary cystic fibrosis patients, at a concentration of 0.2 or 2 µg per gram sputum. As further shown therein, the disruption of the elastic structure of sputum, reduction of DNA content of sputum, and sputum DNA fragmentation by AIR DNase was dose dependent.

As shown in FIGS. 41A-41C, AIR DNase was considerably more effective than Pulmozyme® DNase I at disrupting the elastic structure of sputum (FIG. 41A) and reducing DNA content (FIG. 41B) and fragmenting DNA (FIG. 41C) of sputum from an exemplary cystic fibrosis patient (at a concentration of 2 µg per gram sputum). The data was obtained using the same sputum sample as FIGS. 39A-39C.

As shown in Table 3, of the 10 CF patients which responded to at least one treatment, 6 of the 10 patients responded to AIR DNase more strongly than to Pulmozyme® DNase I, and 9 of the 10 patients responded to AIR DNase at least as well as to Pulmozyme® DNase I.

TABLE 3

Types of response of sputum from 14 cystic fibrosis (CF) patients to ex vivo treatment with each of AIR DNase and Pulmozyme ® DNase I

| Response of sputum to DNase | | No. of CF patient |
|---|---|---|
| AIR DNase | Pulmozyme ® DNase | (total = 14) |
| Strong | None | 3 |
| Strong | Weak | 3 |
| Strong | Strong | 3 |
| None | None | 4 |
| Weak | Strong | 1 |

Representative data from each of the types of patient ex vivo responses summarized in Table 3 is presented in FIGS. 42A-46.

FIGS. 42A and 42B show the efficacy of AIR DNase and Pulmozyme® DNase I, at a concentration of 2 µg DNase per gram sputum, at disrupting the elastic structure of sputum from two of the three cystic fibrosis patients whose sputum exhibited a strong response to AIR DNase but no significant response to Pulmozyme® DNase I.

FIGS. 43A and 43B show the efficacy of AIR DNase and Pulmozyme® DNase I, at a concentration of 2 µg DNase per gram sputum, at disrupting the elastic structure of sputum from two of the three cystic fibrosis patients whose sputum exhibited a strong response to AIR DNase but only a weaker response to Pulmozyme® DNase I.

FIGS. 44A and 44B show the efficacy of AIR DNase and Pulmozyme® DNase I, at a concentration of 2 µg DNase per gram sputum, at disrupting the elastic structure of sputum from two of the three cystic fibrosis patients whose sputum exhibited a strong response to each of AIR DNase and Pulmozyme® DNase I.

FIGS. 45A and 45B show the efficacy of AIR DNase and Pulmozyme® DNase I, at a concentration of 2 µg DNase per gram sputum, at disrupting the elastic structure of sputum from two of the four non-responder cystic fibrosis patients whose sputum did not exhibit a significant response to either AIR DNase or Pulmozyme® DNase I.

FIG. 46 shows the efficacy of AIR DNase and Pulmozyme® DNase I, at a concentration of 2 µg DNase per gram sputum, at disrupting the elastic structure of sputum from the only cystic fibrosis patient (among 14 tested patients) whose sputum exhibited a stronger response to Pulmozyme® DNase I than to AIR DNase.

These above results indicate that the AIR DNase prepared by large scale modification of DNase I with EDA is effective and more potent than Pulmozyme® DNase I in sputum of cystic fibrosis patients.

Example 15

Exemplary Formulation for Actin Inhibition Resistant Modified DNase I (AIR DNase)

The formulation of 150 mM NaCl and 1 mM $CaCl_2$ which was used for enhancing the stability of non-modified DNase I was modified in order to be particularly suitable for modified DNase I (AIR DNase) prepared as described hereinabove (e.g., in Example 14).

In order to evaluate effects of formulations on stability of AIR DNase, DNase solutions were subjected to heat stress in the form of temperatures above 40° C. for 2 hours, and shear stress applied by shaking the solution with a Tissue-Lyser™ device. Aggregate formation was monitored by light transmission at a wavelength of 600 nm.

$CaCl_2$ enhanced the heat stability of AIR DNase in a concentration-dependent manner.

Polysorbate 80 significantly enhanced the stability of AIR DNase towards shear stress. Moreover, no interference between $CaCl_2$ and polysorbate 80 was observed.

Furthermore, $CaCl_2$ and polysorbate 80 have been found to be acceptable for use in pulmonary-delivered drug products (e.g., $CaCl_2$ in Pulmozyme® DNase I formulation, and polysorbate 80 in Pulmicort™ asthma medicament).

Based on these results, an exemplary formulation containing 10 mM $CaCl_2$, 0.01% polysorbate 80, 140 mM NaCl and 5 mg/ml AIR DNase was prepared, the concentration of NaCl being selected in order to maintain an isotonic solution in combination with the 10 mM $CaCl_2$. The pH of the formulation was in a range of 5 to 6.

Example 16

Glycan Structures of Exemplary Actin Inhibition Resistant Modified DNase I (AIR DNase)

Human DNase I has two potential glycosylation sites (N18 and N106 in SEQ ID NO: 1; N19 and N107 in SEQ ID NO: 2) which can be occupied. The glycan structures of actin inhibition resistant modified plant recombinant human DNase I (AIR DNase) prepared as described hereinabove were characterized according to procedures described in International Patent Application Publication WO 2013/114374.

As shown in FIG. 47, the oligosaccharides at the glycosylation sites have typical plant glycan structures, all of which contain a β(1-2) linked xylose attached to the bisecting mannose, and most of which contain an α(1-3) linked fucose attached to the proximal N-acetylglucosamine (GlcNAc).

In particular, the main glycans (each having 33-60% distribution) contained a core structure ($Man_3GlcNAc_2$) with the addition of both a β(1-2) linked xylose and an α(1-3) linked fucose, with an additional substitution of either one or two β(1-2) linked GlcNAcs attached to the non-reducing mannose sugars.

As discussed hereinabove, the molecular weight of the glycans was about 2,900 Da. This molecular weight corresponds to approximately two glycans per protein, indicating that the protein is generally glycosylated at both N18/19 and N106/107.

Example 17

Modified Pulmozyme® DNase I with Diamine-Modified Carboxyl Groups

Carboxyl group modification of Pulmozyme® DNase I by ethylene diamine (EDA) was performed using CMC as described in Examples 8 and 14 (using Pulmozyme® DNase I instead of plant recombinant human DNase I). 500 μg of Pulmozyme® DNase I and 2000 molar equivalents of ethylene diamine were reacted in the presence of 60 or 80 molar equivalents of CMC, 15 mM MES and 2 mM $CaCL_2$, at a pH of 5, for 2 hours at 25° C. The use of 80 molar equivalents of CMC (rather than 60 equivalents as described hereinabove) was tested in view of the presence of additional carboxylic acids in Pulmozyme® DNase I (in the sialic acid residues thereof).

The susceptibility of EDA-modified Pulmozyme® DNase I obtained by modification with EDA to inhibition by actin was compared to that of non-modified Pulmozyme® DNase I.

As shown in FIG. 48, Pulmozyme® DNase I underwent amidation by ethylene diamine, with the extent of amidation being greater in the presence of 80 equivalents CMC than in the presence of 60 equivalents of CMC.

As shown in FIG. 49, Pulmozyme® DNase I modified with ethylene diamine exhibited considerable resistance to actin inhibition, as compared to non-modified Pulmozyme® DNase I, with modified Pulmozyme® DNase I prepared using 80 equivalents of CMC being more resistant to actin inhibition than modified Pulmozyme® DNase I prepared using 60 equivalents of CMC.

These results confirm that resistance to actin inhibition can be obtained via modification of DNases from different sources, including plant-produced and mammalian-produced DNase.

Example 18

Toxicology Studies of Exemplary Actin Inhibition Resistant Modified DNase I (AIR DNase)

To evaluate the safety of AIR DNase (e.g., prepared by modification with EDA as described hereinabove), a GLP-compliant 28-day inhalation toxicity study of AIR DNase was carried out in Sprague-Dawley rats. In the 28-day study in rats, no AIR DNase-related mortalities or effects on body weight, food consumption, ophthalmoscopy, hematology, clinical chemistry, or urinalysis were observed. Overall, comparison of findings in rats treated with DNase prior to chemical modification to those in rats treated with AIR DNase revealed a similar safety profile. The data collected in this study allow a safety bridge to be made for AIR DNase. The highest inhaled safe doses of AIR DNase achieved in rats were equivalent to 12 times a dose of 5 mg/day in humans.

To further evaluate the safety of AIR DNase, an additional inhalation toxicity study (~1 month) is optionally performed in another animal species, e.g., 1 month chronic toxicology studies are performed in two species cynomolgus monkeys, by inhalation in multiple doses relevant to support clinical development studies.

Example 19

Safety and Pharmacokinetics Studies of Exemplary Actin Inhibition Resistant Modified DNase I (AIR DNase)

To further evaluate the safety of AIR DNase (e.g., prepared by modification with EDA as described hereinabove), a randomized, double-blind placebo-controlled Phase I study is performed in healthy adult humans, in order to assess the safety and tolerability of single and/or multiple ascending inhaled doses of AIR DNase, by evaluating number and severity of treatment-emergent adverse events (e.g., dysphonia, dyspnea, pharyngitis, laryngitis, or rhinitis (all non-infectious); conjunctivitis, dyspepsia, rash and urticarial, and chest pain (pleuritic/non-cardiac) and/or pyrexia (general)). In addition, the pharmacokinetics of single ascending inhaled doses of AIR DNase, the trough of AIR DNase plasma concentrations following multiple ascending inhaled doses, and/or whether anti-AIR DNase antibodies are produced following treatment, are optionally assessed.

AIR DNase is prepared as a 2 ml sterile, non-pyrogenic, frozen solution for inhalation, containing 5 mg/ml AIR DNase, 140 mM sodium chloride, 10 mM calcium chloride, and 0.01% (w/v) Polysorbate 80. Placebos are a corresponding formulation without DNase. Formulations are administered by inhalation using a nebulizer system.

In one stage of the study, subjects are assigned to receive a single inhaled dose of 1.25, 2.5 or 5.0 mg AIR DNase (or a matching placebo). Blood samples are drawn for pharmacokinetic assessment of AIR DNase before AIR DNase administration and 0.25, 0.5, 0.75, 1, 1.5, 2, 4 and 8 hours after administration, and the following pharmacokinetic parameters are calculated based on the determined AIR DNase plasma concentrations: AUC(last), $AUC_{0-\infty}$, $C_{max}$, $t_{max}$, elimination rate constant ($k_{el}$), elimination half-life ($t^{1/2}$), and clearance (CL).

In another stage of the study, subjects are assigned to receive multiple inhaled doses of 1.25, 2.5 or 5.0 mg AIR DNase (or a matching placebo), daily on five consecutive days. Blood samples for determining trough AIR DNase plasma concentrations are drawn daily prior to AIR DNase administration.

Safety assessments are based on changes from baseline of vital signs, physical examination, 12-lead ECG parameters, spirometry, pulse oximetry, and safety laboratory assessments (hematology, chemistry, and urinalysis).

Example 20

Efficacy Assessment of Exemplary Actin Inhibition Resistant Modified DNase I (AIR DNase)

To evaluate the efficacy of AIR DNase (e.g., prepared by modification with EDA as described hereinabove) as well as safety, tolerability and pharmacokinetics, a double-blind placebo-controlled Phase II and/or III study, optionally a Phase IIa study, is performed in cystic fibrosis patients who were previously treated with Pulmozyme® DNase for at least 4 months, and who discontinued treatment with Pulmozyme® DNase (e.g., with a washout period of about 2 weeks).

AIR DNase is prepared as described hereinabove, e.g., as a 2 ml sterile, non-pyrogenic, frozen solution for inhalation, containing 5 mg/ml AIR DNase, 140 mM sodium chloride, 10 mM calcium chloride, and 0.01% (w/v) Polysorbate 80. Placebos are a corresponding formulation without DNase. Formulations are administered by inhalation using a nebulizer system.

AIR DNase is administered by inhalation once or twice daily at doses of 1.25, 2.5 and/or 5.0 mg AIR DNase (or a matching placebo), preferably once daily at a dose of 2.5 mg AIR DNase, optionally for about 4 weeks.

Efficacy is evaluated by monitoring pulmonary function by spirometry, and comparing the results with the predicted standard values of the E.R.S. E.G.K.S. 1993 (European Respiratory Society and European Community for Coal and Steel) ["Standardized lung function testing. Official statement of the European Respiratory Society", *Eur Respir J Suppl* 1993, 16:1-100]. Values are given for females and males separately as a function of age and height. Parameters of pulmonary function which are determined (e.g., as a change from baseline) include, e.g., forced expiratory volume in 1 second (FEV1), forced vital capacity (FVC), ratio of FEV1:FVC (FER, or Tiffeneau-Pinelli index), forced expiratory flow (FEF) 25-75%, and peak expiratory flow (PEF). Additional parameters for evaluating pulmonary function which are optionally monitored include lung clearance index, number of respiratory tract infections, and/or days of hospitalization of each patient. Pharmacokinetics of inhaled AIR DNase is determined by monitoring AIR DNase individual plasma levels following administration. The following parameters are optionally also evaluated: sputum rheology (optionally using rheometry procedures described hereinabove), sputum DNA fragment size, AIR DNase level and/or activity (optionally using procedures described hereinabove), sputum pro-inflammatory markers, bacterial burden in sputum as determined by quantitative bacterial culture, and presence of anti-drug antibodies.

In patients who discontinue Pulmozyme® DNase shortly before the AIR DNase treatment, comparison of status of the subjects before and after AIR DNase treatment can be performed, as well as evaluation of the efficacies of Pulmozyme® DNase treatment and AIR DNase treatment.

Children (younger than 12 years old), users of tobacco/nicotine-containing products in the past 6 months, subjects with an FVC of less than 40% or FEV1 of no more than 40% or of at least 90% or predicted normal (for age, gender and height according to E.R.S. E.G.K.S. 1993 tables), and subjects lacking medical stability in the past month or a stabled inhaled regiment of antibiotics and steroids for at least four months, are preferably excluded from the study.

Safety assessments are optionally based on vital signs, physical examination, ECG parameters, spirometry, pulse oximetry, treatment-induced antibodies to AIR DNase, and/or safety laboratory assessments (hematology, serum chemistry, and urinalysis).

Children (younger than 12 years old) are optionally subjected to a different study or studies, with a different dose and/or regimen (e.g., lower overall dosage), for example, as described hereinabove.

Example 21

Effect of Exemplary Actin Inhibition Resistant Modified DNase I (AIR DNase) on Sputum of Patients with Different Types of Suppurative Lung Disease In order to further evaluate the efficacy of AIR DNase (e.g., prepared by modification with EDA as described hereinabove) in suppurative lung diseases in addition to cystic fibrosis, the ability of AIR DNase to reduce viscosity of sputum isolated from patients with different types of suppurative lung disease, including non-cystic fibrosis-related suppurative lung disease, is evaluated in an ex vivo study.

Patients (preferably in an age range of 18-100 years) with a suppurative lung disease, such as non-cystic fibrosis bronchiectasis or chronic obstructive pulmonary disease (COPD) are selected. Patients exhibiting a presence of HIV, HBsAg, hepatitis C and/or active tuberculosis are optionally excluded. The number of patients is optionally in a range of about 50 to about 100.

After obtaining a sputum sample from a patient (optionally more than one sample can be taken from each patient), the sputum is assessed for DNA level, DNA fragmentation and sputum rheology parameters, before and after ex vivo treatment with AIR DNase (using procedures such as described hereinabove), in order to ascertain that the AIR DNase is effective at reducing sputum viscosity. A portion of the sputum is optionally analyzed for the presence of bacteria. Sputum samples may optionally be stored at 4° C. or −80° C.

Example 22

Efficacy Assessment of Exemplary Actin Inhibition Resistant Modified DNase I (AIR DNase) in Patients with Different Types of Suppurative Lung Disease To evaluate the efficacy of AIR DNase (e.g., prepared by modification with EDA as described hereinabove) administered by inhalation, and optionally also safety, tolerability and pharmacokinetics, a double-blind placebo-controlled Phase II and/or III study, optionally a Phase IIa study, is performed in patients with different types of suppurative lung disease, including non-cystic fibrosis-related suppurative lung disease.

AIR DNase is optionally prepared and administered by inhalation according to procedures described in Example 20.

Safety assessment and/or evaluation of efficacy (e.g., effects on pulmonary function), pharmacokinetics of inhaled AIR DNase, sputum rheology, presence of anti-drug antibodies, and/or DNA fragment size, AIR DNase level and/or activity, pro-inflammatory markers, and/or bacterial burden in sputum are optionally performed as described in Example 20.

Children (younger than 12 years old), users of tobacco/nicotine-containing products in the past 6 months, subjects with an FVC of less than 40% or FEV1 of no more than 40% or of at least 90% or predicted normal (for age, gender and height according to E.R.S. E.G.K.S. 1993 tables), and subjects lacking medical stability in the past month or a stabled inhaled regiment of antibiotics and steroids for at least four months, are preferably excluded from the study.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A modified DNase I protein comprising an amino acid sequence of a DNase I protein, in which at least five carboxylic acid groups are replaced by amide groups, wherein the modified DNase I protein is characterized by a catalytic efficiency with respect to DNA hydrolytic activity in the absence of actin which is greater than a catalytic efficiency of a non-modified DNase I protein with respect to DNA hydrolytic activity in the absence of actin, wherein the modified DNase I protein differs from said non-modified DNase I protein only in said at least five carboxylic acid groups being replaced by said amide group, and wherein the modified DNase I protein is further characterized by at least one property selected from the group consisting of:
   a) a DNA hydrolytic activity in the presence of 5 μg/ml human non-muscle actin which is at least 50% of a DNA hydrolytic activity of the modified DNase I protein in the absence of human non-muscle actin, at a modified DNase I concentration of 45 ng/ml;
   b) a DNA hydrolytic activity in the presence of 50 μg/ml human non-muscle actin which is at least 20% of a DNA hydrolytic activity of the modified DNase I protein in the absence of human non-muscle actin, at a DNase I concentration of 45 ng/ml;
   c) a DNA hydrolytic activity in the presence of 5 μg/ml human non-muscle actin which is at least 150% of a DNA hydrolytic activity of a non-modified DNase I protein in the presence of 5 μg/ml human non-muscle actin, at a DNase I concentration of 45 ng/ml;
   d) a DNA hydrolytic activity in the presence of 50 μg/ml human non-muscle actin which is at least 150% of a DNA hydrolytic activity of a non-modified DNase I protein in the presence of 50 μg/ml human non-muscle actin, at a DNase I concentration of 45 ng/ml; and
   e) an $IC_{50}$ with respect to DNA hydrolytic activity in the presence of human non-muscle actin which is at least twice an $IC_{50}$ of a non-modified DNase I protein with respect to DNA hydrolytic activity in the presence of human non-muscle actin.

2. The modified DNase I protein of claim 1, being characterized by a DNA hydrolytic activity in the presence of 5 μg/ml human non-muscle actin which is at least 200% of a DNA hydrolytic activity of a non-modified DNase I protein in the presence of 5 μg/ml human non-muscle actin, at a DNase I concentration of 45 ng/ml.

3. The modified DNase I protein of claim 1, being characterized by a DNA hydrolytic activity in the presence of 50 μg/ml human non-muscle actin which is at least 200% of a DNA hydrolytic activity of a non-modified DNase I protein in the presence of 50 μg/ml human non-muscle actin, at a DNase I concentration of 45 ng/ml.

4. The modified DNase I protein of claim 1, being characterized by an $IC_{50}$ with respect to DNA hydrolytic activity in the presence of human non-muscle actin which is at least 3-fold an $IC_{50}$ of a non-modified DNase I protein with respect to DNA hydrolytic activity in the presence of human non-muscle actin.

5. The modified DNase I protein of claim 1, wherein said at least five carboxylic acid groups of the DNase I protein are each replaced by an amide group of the formula:

—C(=O)—NR'R''

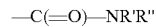

wherein each of R' and R'' is independently selected from the group consisting of hydrogen, and a saturated or unsaturated, substituted or non-substituted hydrocarbon moiety, optionally interrupted by one or more heteroatoms, said hydrocarbon moiety comprising from 1 to 20 carbon atoms, and wherein at least one of R' and R'' is said saturated or unsaturated, substituted or non-substituted hydrocarbon moiety.

6. A pharmaceutical composition comprising, as an active ingredient, the modified DNase I protein of claim 1 and a pharmaceutically acceptable carrier.

7. A method of treating a disease or condition associated with excess extracellular DNA in a fluid, secretion or tissue of a subject in need thereof, the method comprising administering to the subject a therapeutically effective amount of the modified DNase I protein of claim 1, thereby treating the disease or condition.

8. A method of treating a disease or condition selected from the group consisting of bronchitis, cystic fibrosis, non-cystic fibrosis bronchiectasis, chronic obstructive pulmonary disease (COPD), lupus erythematosus, lupus nephritis, Cockayne syndrome, Angelman syndrome, male infertility, metastatic cancer, a viral, bacterial, fungal or protozoan infection sepsis, myocardial infarction, atherosclerosis, diabetes, delayed type hypersensitivity and a uterine disorder, the method comprising administering to a subject in need thereof a therapeutically effective amount of the modified DNase I protein of claim 1, thereby treating the disease or condition.

9. A modified DNase I protein comprising an amino acid sequence of a DNase I protein in which at least five carboxylic acid groups in said DNase I protein are each replaced by an amide group of the formula:

—C(=O)—NR'R''

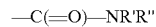

wherein each of R' and R'' is independently selected from the group consisting of hydrogen, and a saturated or unsaturated, substituted or non-substituted hydrocarbon moiety, optionally interrupted by one or more heteroatoms, said hydrocarbon moiety comprising from 1 to 20 carbon atoms, and wherein at least one of R' and R" is said saturated or unsaturated, substituted or non-substituted hydrocarbon moiety, the modified DNase I protein being characterized by an $IC_{50}$ with respect to DNA hydrolytic activity in the presence of human non-muscle actin which is at least twice an $IC_{50}$ of said non-modified DNase I protein with respect to DNA hydrolytic activity in the presence of human non-muscle actin, wherein the modified DNase I protein differs from said non-modified DNase I protein only in said at least two carboxylic acid groups being replaced by said amide group.

10. The modified DNase I protein of claim 9, wherein said amide group has the general formula:

—C(=O)—NH—R' wherein R' is selected from the group consisting of alkyl, alkenyl and alkynyl, each being non-substituted or substituted with one or more substituents selected from the group consisting of hydroxy and amino.

11. The modified DNase I protein of claim 9, wherein said at least five carboxylic acid groups are each independently within a side chain of an amino acid residue selected from the group consisting of a glutamic acid residue, an aspartic acid residue, an N-methyl-glutamic acid residue, an N-methylaspartic acid residue, an α-methylglutamic acid residue, an α-methylaspartic acid residue, a γ-carboxyglutamic acid residue, an N-(carboxymethyl)glycine residue, an N-(2-carboxyethyl)glycine residue and an α-aminoadipic acid residue.

12. The modified DNase I protein of claim 9, being characterized by a Michaelis constant with respect to DNA hydrolytic activity which is lower than a Michaelis constant of a non-modified DNase I protein with respect to DNA hydrolytic activity.

13. The modified DNase I protein of claim 9, being characterized by a Michaelis constant with respect to DNA hydrolytic activity which is no more than 20 μg/ml DNA.

14. The modified DNase I protein of claim 9, being characterized by a specific activity with respect to DNA hydrolytic activity which is at least 70% of a specific activity of a non-modified DNase I protein with respect to DNA hydrolytic activity.

15. A process for preparing the modified DNase I protein of claim 9, the process comprising reacting said DNase I protein with an amine-containing compound of the formula:

HNR'R"

in the presence of a coupling agent,
wherein each of R' and R" is independently selected from the group consisting of hydrogen, and said saturated or unsaturated, substituted or non-substituted hydrocarbon moiety, optionally interrupted by one or more heteroatoms, and wherein at least one of R' and R" is said saturated or unsaturated, substituted or non-substituted hydrocarbon moiety.

16. A pharmaceutical composition comprising, as an active ingredient, the modified DNase I protein of claim 9 and a pharmaceutically acceptable carrier.

17. The pharmaceutical composition of claim 16, further comprising a calcium salt, wherein a concentration of calcium in the composition is in a range of from 5 to 15 mM of calcium.

18. A method of treating a disease or condition associated with excess extracellular DNA in a fluid, secretion or tissue of a subject in need thereof, the method comprising administering to the subject a therapeutically effective amount of the modified DNase I protein of claim 9, thereby treating the disease or condition.

19. A method of treating a disease or condition selected from the group consisting of bronchitis, cystic fibrosis, non-cystic fibrosis bronchiectasis, chronic obstructive pulmonary disease (COPD), lupus erythematosus, lupus nephritis, Cockayne syndrome, Angelman syndrome, male infertility, metastatic cancer, a viral, bacterial, fungal or protozoan infection sepsis, myocardial infarction, atherosclerosis, diabetes, delayed type hypersensitivity and a uterine disorder, the method comprising administering to a subject in need thereof a therapeutically effective amount of the modified DNase I protein of claim 9, thereby treating the disease or condition.

* * * * *

```
                          SEQUENCE LISTING

<160> NUMBER OF SEQ ID NOS: 9

<210> SEQ ID NO 1
<211> LENGTH: 260
<212> TYPE: PRT
<213> ORGANISM: Homo sapiens

<400> SEQUENCE: 1

Leu Lys Ile Ala Ala Phe Asn Ile Gln Thr Phe Gly Glu Thr Lys Met
1               5                   10                  15

Ser Asn Ala Thr Leu Val Ser Tyr Ile Val Gln Ile Leu Ser Arg Tyr
            20                  25                  30

Asp Ile Ala Leu Val Gln Glu Val Arg Asp Ser His Leu Thr Ala Val
        35                  40                  45

Gly Lys Leu Leu Asp Asn Leu Asn Gln Asp Ala Pro Asp Thr Tyr His
    50                  55                  60

Tyr Val Val Ser Glu Pro Leu Gly Arg Asn Ser Tyr Lys Glu Arg Tyr
65                  70                  75                  80

Leu Phe Val Tyr Arg Pro Asp Gln Val Ser Ala Val Asp Ser Tyr Tyr
                85                  90                  95

Tyr Asp Asp Gly Cys Glu Pro Cys Gly Asn Asp Thr Phe Asn Arg Glu
            100                 105                 110

Pro Ala Ile Val Arg Phe Phe Ser Arg Phe Thr Glu Val Arg Glu Phe
        115                 120                 125

Ala Ile Val Pro Leu His Ala Ala Pro Gly Asp Ala Val Ala Glu Ile
    130                 135                 140

Asp Ala Leu Tyr Asp Val Tyr Leu Asp Val Gln Glu Lys Trp Gly Leu
145                 150                 155                 160

Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
            180                 185                 190

Gln Trp Leu Ile Pro Asp Ser Ala Asp Thr Thr Ala Thr Pro Thr His
        195                 200                 205

Cys Ala Tyr Asp Arg Ile Val Val Ala Gly Met Leu Leu Arg Gly Ala
    210                 215                 220

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
                245                 250                 255

Val Met Leu Lys
            260

<210> SEQ ID NO 2
<211> LENGTH: 261
<212> TYPE: PRT
<213> ORGANISM: Artificial sequence
<220> FEATURE:
<223> OTHER INFORMATION: Putative amino acid sequence of the purified,
      plant expressed rhDNase I

<400> SEQUENCE: 2
```

```
Gly Leu Lys Ile Ala Ala Phe Asn Ile Gln Thr Phe Gly Glu Thr Lys
1               5                   10                  15

Met Ser Asn Ala Thr Leu Val Ser Tyr Ile Val Gln Ile Leu Ser Arg
            20                  25                  30

Tyr Asp Ile Ala Leu Val Gln Glu Val Arg Asp Ser His Leu Thr Ala
        35                  40                  45

Val Gly Lys Leu Leu Asp Asn Leu Asn Gln Asp Ala Pro Asp Thr Tyr
    50                  55                  60

His Tyr Val Val Ser Glu Pro Leu Gly Arg Asn Ser Tyr Lys Glu Arg
65                  70                  75                  80

Tyr Leu Phe Val Tyr Arg Pro Asp Gln Val Ser Ala Val Asp Ser Tyr
                85                  90                  95

Tyr Tyr Asp Asp Gly Cys Glu Pro Cys Gly Asn Asp Thr Phe Asn Arg
            100                 105                 110

Glu Pro Ala Ile Val Arg Phe Phe Ser Arg Phe Thr Glu Val Arg Glu
        115                 120                 125

Phe Ala Ile Val Pro Leu His Ala Ala Pro Gly Asp Ala Val Ala Glu
    130                 135                 140

Ile Asp Ala Leu Tyr Asp Val Tyr Leu Asp Val Gln Glu Lys Trp Gly
145                 150                 155                 160

Leu Glu Asp Val Met Leu Met Gly Asp Phe Asn Ala Gly Cys Ser Tyr
                165                 170                 175

Val Arg Pro Ser Gln Trp Ser Ser Ile Arg Leu Trp Thr Ser Pro Thr
            180                 185                 190

Phe Gln Trp Leu Ile Pro Asp Ser Ala Asp Thr Thr Ala Thr Pro Thr
        195                 200                 205

His Cys Ala Tyr Asp Arg Ile Val Val Ala Gly Met Leu Leu Arg Gly
    210                 215                 220

Ala Val Val Pro Asp Ser Ala Leu Pro Phe Asn Phe Gln Ala Ala Tyr
225                 230                 235                 240

Gly Leu Ser Asp Gln Leu Ala Gln Ala Ile Ser Asp His Tyr Pro Val
                245                 250                 255

Glu Val Met Leu Lys
            260

<210> SEQ ID NO 3
<211> LENGTH: 99
<212> TYPE: DNA
<213> ORGANISM: Artificial sequence
<220> FEATURE:
<223> OTHER INFORMATION: Coding sequence of polypeptide of ABPI leader
      signal

<400> SEQUENCE: 3
atgattgtgc tttctgtggg atctgcttct tcttctccaa ttgtggtggt gttctctgtg    60
gctcttcttc ttttctactt ctctgagact tctcttggc                            99

<210> SEQ ID NO 4
<211> LENGTH: 849
<212> TYPE: DNA
<213> ORGANISM: Homo sapiens

<400> SEQUENCE: 4
atgaggggca tgaagctgct gggggcgctg ctggcactgg cggccctact gcaggggcc     60 gtgtccctga agatcgcagc cttcaacatc cagacatttg gggagaccaa gatgtccaat   120
gccaccctcg tcagctacat tgtgcagatc ctgagccgct atgacatcgc cctggtccag   180
```

| | |
|---|---|
| gaggtcagag acagccacct gactgccgtg gggaagctgc tggacaacct caatcaggat | 240 |
| gcaccagaca cctatcacta cgtggtcagt gagccactgg gacggaacag ctataaggag | 300 |
| cgctacctgt tcgtgtacag gcctgaccag gtgtctgcgg tggacagcta ctactacgat | 360 |
| gatggctgcg agcccgcgg gaacgacacc ttcaaccgag agccagccat tgtcaggttc | 420 |
| ttctcccggt tcacagaggt cagggagttt gccattgttc ccctgcatgc ggccccgggg | 480 |
| gacgcagtag ccgagatcga cgctctctat gacgtctacc tggatgtcca agagaaatgg | 540 |
| ggcttggagg acgtcatgtt gatgggcgac ttcaatgcgg gctgcagcta tgtgagaccc | 600 |
| tcccagtggt catccatccg cctgtggaca agccccacct tccagtggct gatccccgac | 660 |
| agcgctgaca ccacagctac acccacgcac tgtgcctatg acaggatcgt ggttgcaggg | 720 |
| atgctgctcc gaggcgccgt tgttcccgac tcggctcttc cctttaactt ccaggctgcc | 780 |
| tatggcctga gtgaccaact ggcccaagcc atcagtgacc actatccagt ggaggtgatg | 840 |
| ctgaagtga | 849 |

<210> SEQ ID NO 5
<211> LENGTH: 282
<212> TYPE: PRT
<213> ORGANISM: Homo sapiens

<400> SEQUENCE: 5

Met Arg Gly Met Lys Leu Leu Gly Ala Leu Ala Leu Ala Ala Leu
1               5                   10                  15

Leu Gln Gly Ala Val Ser Leu Lys Ile Ala Ala Phe Asn Ile Gln Thr
            20                  25                  30

Phe Gly Glu Thr Lys Met Ser Asn Ala Thr Leu Val Ser Tyr Ile Val
        35                  40                  45

Gln Ile Leu Ser Arg Tyr Asp Ile Ala Leu Val Gln Glu Val Arg Asp
    50                  55                  60

Ser His Leu Thr Ala Val Gly Lys Leu Leu Asp Asn Leu Asn Gln Asp
65                  70                  75                  80

Ala Pro Asp Thr Tyr His Tyr Val Val Ser Glu Pro Leu Gly Arg Asn
                85                  90                  95

Ser Tyr Lys Glu Arg Tyr Leu Phe Val Tyr Arg Pro Asp Gln Val Ser
            100                 105                 110

Ala Val Asp Ser Tyr Tyr Tyr Asp Asp Gly Cys Glu Pro Cys Gly Asn
        115                 120                 125

Asp Thr Phe Asn Arg Glu Pro Ala Ile Val Arg Phe Phe Ser Arg Phe
    130                 135                 140

Thr Glu Val Arg Glu Phe Ala Ile Val Pro Leu His Ala Ala Pro Gly
145                 150                 155                 160

Asp Ala Val Ala Glu Ile Asp Ala Leu Tyr Asp Val Tyr Leu Asp Val
                165                 170                 175

Gln Glu Lys Trp Gly Leu Glu Asp Val Met Leu Met Gly Asp Phe Asn
            180                 185                 190

Ala Gly Cys Ser Tyr Val Arg Pro Ser Gln Trp Ser Ser Ile Arg Leu
        195                 200                 205

Trp Thr Ser Pro Thr Phe Gln Trp Leu Ile Pro Asp Ser Ala Asp Thr
    210                 215                 220

Thr Ala Thr Pro Thr His Cys Ala Tyr Asp Arg Ile Val Val Ala Gly
225                 230                 235                 240

Met Leu Leu Arg Gly Ala Val Val Pro Asp Ser Ala Leu Pro Phe Asn

```
                    245                 250                 255
Phe Gln Ala Ala Tyr Gly Leu Ser Asp Gln Leu Ala Gln Ala Ile Ser
                260                 265                 270

Asp His Tyr Pro Val Glu Val Met Leu Lys
            275                 280
```

<210> SEQ ID NO 6
<211> LENGTH: 786
<212> TYPE: DNA
<213> ORGANISM: Artificial sequence
<220> FEATURE:
<223> OTHER INFORMATION: Coding sequence of the recombinant DNase I
      without the leader sequence

<400> SEQUENCE: 6

```
cttaaaatcg ctgctttcaa catccaaact ttcggagaga ctaagatgtc taacgctact      60
cttgtgtcct acatcgttca gattctctcc agatacgata ttgctcttgt tcaggaagtt    120
agggattctc accttactgc tgtgggaaag cttcttgata acctcaatca ggatgctcca    180
gatacttacc actacgttgt gtctgaacca cttggaagaa actcctacaa agagcgttac    240
ctctttgttt accgtccaga tcaagtttct gctgtggatt cctactacta cgatgatgga    300
tgtgagccat gcggaaacga tactttcaat agagagccag ctatcgttcg ttttttcagt    360
aggttcactg aagttcgtga gtttgctatt gtgccacttc atgctgctcc aggtgatgct    420
gttgctgaga ttgatgctct ctacgatgtg taccttgatg ttcaagagaa gtggggattg    480
gaggatgtta tgctcatggg agatttcaat gctggatgct cttatgttag gccatctcag    540
tggtcatcta ttaggctttg gacttcccca actttccaat ggcttatccc agattccgct    600
gatacaactg ctactccaac tcattgtgct tacgatagga ttgtggtggc tggaatgctt    660
cttagaggtg ctgttgttcc agattctgct ctcccattca atttccaagc tgcttacgga    720
ctttctgatc aacttgctca ggctatttct gatcactacc cagttgaggt gatgttgaag    780
tgatga                                                                786
```

<210> SEQ ID NO 7
<211> LENGTH: 885
<212> TYPE: DNA
<213> ORGANISM: Artificial sequence
<220> FEATURE:
<223> OTHER INFORMATION: Coding sequence of rhDNase I (ABPI+DNase I)

<400> SEQUENCE: 7

```
atgattgtgc tttctgtggg atctgcttct tcttctccaa ttgtggtggt gttctctgtg      60
gctcttcttc ttttctactt ctctgagact tctcttggcc ttaaaatcgc tgctttcaac    120
atccaaactt tcggagagac taagatgtct aacgctactc ttgtgtccta catcgttcag    180
attctctcca gatacgatat tgctcttgtt caggaagtta gggattctca ccttactgct    240
gtgggaaagc ttcttgataa cctcaatcag gatgctccag atacttacca ctacgttgtg    300
tctgaaccac ttggaagaaa ctcctacaaa gagcgttacc tctttgttta ccgtccagat    360
caagtttctg ctgtggattc ctactactac gatgatggat gtgagccatg cggaaacgat    420
actttcaata gagagccagc tatcgttcgt tttttcagta ggttcactga agttcgtgag    480
tttgctattg tgccacttca tgctgctcca ggtgatgctg ttgctgagat tgatgctctc    540
tacgatgtgt accttgatgt tcaagagaag tggggattgg aggatgttat gctcatggga    600
gatttcaatg ctggatgctc ttatgttagg ccatctcagt ggtcatctat taggctttgg    660
```

```
acttcccccaa ctttccaatg gcttatccca gattccgctg atacaactgc tactccaact    720
cattgtgctt acgataggat tgtggtggct ggaatgcttc ttagaggtgc tgttgttcca    780
gattctgctc tcccattcaa tttccaagct gcttacggac tttctgatca acttgctcag    840
gctatttctg atcactaccc agttgaggtg atgttgaagt gatga                    885
```

```
<210> SEQ ID NO 8
<211> LENGTH: 33
<212> TYPE: PRT
<213> ORGANISM: Artificial sequence
<220> FEATURE:
<223> OTHER INFORMATION: Arabidopsis derived ABPI endoplasmic reticulum
      targeting signal peptide

<400> SEQUENCE: 8
```

```
Met Ile Val Leu Ser Val Gly Ser Ala Ser Ser Pro Ile Val Val
1               5                   10                  15

Val Phe Ser Val Ala Leu Leu Leu Phe Tyr Phe Ser Glu Thr Ser Leu
            20                  25                  30

Gly
```

```
<210> SEQ ID NO 9
<211> LENGTH: 293
<212> TYPE: PRT
<213> ORGANISM: Artificial sequence
<220> FEATURE:
<223> OTHER INFORMATION: Plant recombinant human DNase I

<400> SEQUENCE: 9
```

```
Met Ile Val Leu Ser Val Gly Ser Ala Ser Ser Pro Ile Val Val
1               5                   10                  15

Val Phe Ser Val Ala Leu Leu Leu Phe Tyr Phe Ser Glu Thr Ser Leu
            20                  25                  30

Gly Leu Lys Ile Ala Ala Phe Asn Ile Gln Thr Phe Gly Glu Thr Lys
            35                  40                  45

Met Ser Asn Ala Thr Leu Val Ser Tyr Ile Val Gln Ile Leu Ser Arg
    50                  55                  60

Tyr Asp Ile Ala Leu Val Gln Glu Val Arg Asp Ser His Leu Thr Ala
65                  70                  75                  80

Val Gly Lys Leu Leu Asp Asn Leu Asn Gln Asp Ala Pro Asp Thr Tyr
                85                  90                  95

His Tyr Val Val Ser Glu Pro Leu Gly Arg Asn Ser Tyr Lys Glu Arg
            100                 105                 110

Tyr Leu Phe Val Tyr Arg Pro Asp Gln Val Ser Ala Val Asp Ser Tyr
        115                 120                 125

Tyr Tyr Asp Asp Gly Cys Glu Pro Cys Gly Asn Asp Thr Phe Asn Arg
130                 135                 140

Glu Pro Ala Ile Val Arg Phe Phe Ser Arg Phe Thr Glu Val Arg Glu
145                 150                 155                 160

Phe Ala Ile Val Pro Leu His Ala Ala Pro Gly Asp Ala Val Ala Glu
                165                 170                 175

Ile Asp Ala Leu Tyr Asp Val Tyr Leu Asp Val Gln Glu Lys Trp Gly
            180                 185                 190

Leu Glu Asp Val Met Leu Met Gly Asp Phe Asn Ala Gly Cys Ser Tyr
        195                 200                 205

Val Arg Pro Ser Gln Trp Ser Ser Ile Arg Leu Trp Thr Ser Pro Thr
    210                 215                 220
```

```
Phe Gln Trp Leu Ile Pro Asp Ser Ala Asp Thr Thr Ala Thr Pro Thr
225                 230                 235                 240

His Cys Ala Tyr Asp Arg Ile Val Val Ala Gly Met Leu Leu Arg Gly
                245                 250                 255

Ala Val Val Pro Asp Ser Ala Leu Pro Phe Asn Phe Gln Ala Ala Tyr
                260                 265                 270

Gly Leu Ser Asp Gln Leu Ala Gln Ala Ile Ser Asp His Tyr Pro Val
        275                 280                 285

Glu Val Met Leu Lys
    290
```